(12) United States Patent
Merighi et al.

(10) Patent No.: US 11,028,419 B2
(45) Date of Patent: *Jun. 8, 2021

(54) BIOSYNTHESIS OF HUMAN MILK OLIGOSACCHARIDES IN ENGINEERED BACTERIA

(71) Applicant: Glycosyn LLC, Woburn, MA (US)

(72) Inventors: Massimo Merighi, Somerville, MA (US); John M. McCoy, Reading, MA (US); Matthew Ian Heidtman, Brighton, MA (US)

(73) Assignee: Glycosyn LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/442,127

(22) Filed: Feb. 24, 2017

(65) Prior Publication Data

US 2017/0226547 A1 Aug. 10, 2017

Related U.S. Application Data

(60) Continuation of application No. 14/033,664, filed on Sep. 23, 2013, now Pat. No. 9,587,241, which is a division of application No. 13/398,526, filed on Feb. 16, 2012, now Pat. No. 9,453,230.

(60) Provisional application No. 61/443,470, filed on Feb. 16, 2011.

(51) Int. Cl.

| C12P 19/18 | (2006.01) |
|---|---|
| C12P 19/00 | (2006.01) |
| C12N 9/00 | (2006.01) |
| C12N 9/10 | (2006.01) |
| C12N 9/38 | (2006.01) |
| C12P 19/26 | (2006.01) |
| C07H 3/06 | (2006.01) |
| C07H 13/04 | (2006.01) |
| C12N 15/70 | (2006.01) |
| C12N 9/14 | (2006.01) |

(52) U.S. Cl.
CPC ............... *C12P 19/00* (2013.01); *C07H 3/06* (2013.01); *C07H 13/04* (2013.01); *C12N 9/00* (2013.01); *C12N 9/1051* (2013.01); *C12N 9/14* (2013.01); *C12N 9/2471* (2013.01); *C12N 15/70* (2013.01); *C12P 19/18* (2013.01); *C12P 19/26* (2013.01); *C12Y 204/01* (2013.01); *C12Y 204/01065* (2013.01); *C12Y 302/01023* (2013.01); *C12Y 306/03018* (2013.01); *Y02P 20/52* (2015.11)

(58) Field of Classification Search
CPC ....................................................... C12P 19/18
See application file for complete search history.

(56) References Cited

U.S. PATENT DOCUMENTS

| 5,270,181 | A | 12/1993 | McCoy et al. |
|---|---|---|---|
| 7,268,221 | B2 | 9/2007 | Caimi et al. |
| 7,521,212 | B1 | 4/2009 | Samain et al. |
| 7,820,422 | B2 | 10/2010 | Samain |
| 9,453,230 | B2 | 9/2016 | Merighi et al. |
| 9,587,241 | B2 | 3/2017 | Merighi et al. |
| 9,970,018 | B2 | 5/2018 | Merighi et al. |
| 2008/0145899 | A1 | 6/2008 | Johnson et al. |
| 2017/0268010 | A1 | 9/2017 | Merighi et al. |
| 2018/0251771 | A1 | 9/2018 | Merighi et al. |

FOREIGN PATENT DOCUMENTS

| JP | 2013535962 A | 9/2013 |
|---|---|---|
| JP | 2014504874 A | 2/2014 |
| JP | 2017093453 A | 6/2017 |
| WO | WO-2006034225 A2 | 3/2006 |
| WO | WO-2010070104 A1 | 6/2010 |
| WO | WO-2012007481 A2 | 1/2012 |
| WO | WO-2012097950 A1 | 7/2012 |
| WO | 2012112777 A2 | 8/2012 |
| WO | 2015150328 A1 | 10/2015 |

OTHER PUBLICATIONS

S. Drouillard et al. "Large-Scale Synthesis of H-Antigen Oligosaccharides by Helicobacter pylori alpha 1,2-Fucosyltransferase in Metabolically Engineered *Escherichia coli* Cells", Angew. Chem. Int. Ed. 45: 1778-1780. (Year: 2006).*
A. Lewendon et al. "Structural and Mechanistic Studies of Galactoside Acetyltransferase, the *Escherichia coli* LacA Gene Product", Journal of Biological Chemistry 270(44):26326-26331. (Year: 1995).*
Albermann et al. "Synthesis of the Milk Oligosaccharide 2'-Fucosyllactose Using Recombinant Bacterial Enzymes." *Carbohydr. Res.* 334.2(2001):97-103.
Amonsen et al. "Human Parainfluenza Viruses hPIV1 and hPIV3 Bind Oligosaccharides with a 2-3-Linked Sialic Acids that are Distinct from those Bound by H5 Avian Influenza Virus Hemagglutinin." J. Virol. 81.15(2007):8341-8345.
Bao et al. "Capillary Electrophoresis of Acidic Oligosaccharides from Human Milk." *Electrophoresis.* 29.12(2008):2508-2515.
Bao et al. "Simultaneous Quantification of Sialyloligosaccharides from Human Milk by Capillary Electrophoresis." *Anal. Biochem.* 370(2007):206-214.

(Continued)

*Primary Examiner* — Rebecca E Prouty

(74) *Attorney, Agent, or Firm* — Mintz Levin Cohn Ferris Glovsky and Popeo, P.C.; Ingrid A. Beattie

(57) ABSTRACT

The invention provides compositions and methods for engineering bacteria to produce fucosylated oligosaccharides, and the use thereof in the prevention or treatment of infection.

21 Claims, 24 Drawing Sheets

Specification includes a Sequence Listing.

(56) References Cited

OTHER PUBLICATIONS

Belfort et al. "Characterization of the *Escherichia coli thyA* Gene and its Amplified Thymidylate Synthetase Product." PNAS. 80.7(1983):1858-1861.
Bettler et al. "The Living Factory: In vivo Production of N-Acetyl-lactosamine Containing Carbohydrates in *E. coli*." Glycoconj. J. 16.3(1999):205-212.
Bode et al. "Inhibition of Monocyte, Lymphocyte, and Neutrophil Adhesion to Endothelial Cells by Human Milk Oligosaccharides." Thrombosis Haemostasis. 92.6(2004):1402-1410.
Charlwood et al. "A Detailed Analysis of Neutral and Acidic Carbohydrates in Human Milk." Anal. Biochem. 273.2(1999):261-277.
Chaturvedi et al. "Fucosylated Human Milk Oligosaccharides Vary Between Individuals and Over the Course of Lactation." Glycobiol. 11.5(2001):365-372.
Chaturvedi et al. "Survival of Human Milk Oligosaccharides in the Intestine of Infants." Adv. Exp. Med. Biol. 501(2001):315-323.
Couceiro et al. "Influenza Virus Strains Selectively Recognize Sialyloligosaccharides on Human Respiratory Epithelium; The Role of the Host Cell in Selection of Hemagglutinin Receptor Specificity." Virus Res. 29.2(1993):155-165.
Court et al. "Genetic Engineering Using Homologous Recombination." Annu. Rev. Genet. 36(2002):361-388.
Coyne et al., "Bacteroides fragilis NCTC9343 produces at least three distinct capsular polysaccharides: cloning, characterization, and reassignment of polysaccharide B and C biosynthesis loci," Infect Immun. Nov. 2000; 68(11): 6176-81.
Crout et al. "Glycosidases and Glycosyl Transferases in Glycoside and Oligosaccharide Synthesis." Curr. Opin. Chem. Biol. 2.1(1998):98-111.
Danchin. "Cells need safety valves", Bioessays, 31:769-773 (2009).
De Vries et al. "Fucosyltransferases: Structure/Function Studies." Glycobiol. 11.10(2001):119R-128R.
Dumon et al. "In vivo fucosylation of lacto-N-neotetraose and lacto-N-neohexaose by heterologous expression of Helicobacter pylori alpha-1,3 fucosyltransferase in engineered *Escherichia coli*", Glycoconjugate Journal 18:465-474. (2001).
Dumon et al. "Production of Lewis x Tetrasaccharides by Metabolically Engineered *Escherichia coli*." Chembiochem. 7.2(2006):359-365.
Dumon et al., "Assessment of the two Helicobacter pylori alpha-1,3-fucosyltransferase ortholog genes for the large-scale synthesis of LewisX human milk oligosaccharides by metabolically engineered *Escherichia coli*," Biotechnol Prog. Mar.-Apr. 2004; 20(2): 412-419.
Easton et al. "Human Myeloid a 3-Fucosyltransferase is Involved in the Expression of the Sialyl-Lewisx Determinant, a Ligand for E- and P-Selectin." Blood. 81.11(1993):2978-2986.
Endo et al. "Large-Scale Production of N-Acetyllactosamine Through Bacterial Coupling." Carbohydr. Res. 316.1-4(1999):179-183.
Endo et al. "Large-Scale Production of the Carbohydrate Portion of the Sialyl-Tn Epitope, a-Neup5Ac-(2-*6)-D-GalpNAc, Through Bacterial Coupling." Carbohydr. Res. 330.4(2001):439-443.
Endo et al. "Large-Scale Production of the CMP-NeuAc and Sialylated Oligosaccharides Through Bacterial Coupling." Appl. Microbiol. Biotechnol. 53.3(2000):257-261.
Erney et al. "Human Milk Oligosaccharides: A Novel Method Provides Insight into Human Genetics." Adv. Exp. Med. Biol. 501(2001):285-297.
Fierfort et al. "Genetic Engineering of *Escherichia coli* for the Econominal Production of Sialylated Oligosaccharides." J. Biotechnol. 134.3-4(2008):261-265.
Flowers. "Chemical Synthesis of Oligosaccharides." Meth. Enzymol. 50(1978):93-121.
Garcia et al. "Comparison and Calibration of Different Reporters for Quantitative Analysis of Gene Expression." Biophys. J. 101(2011):535-544.

Ge et al. "Cloning and Heterologous Expression of an a1,3-Fucosyltransferase Gene from the Gastric Pathogen Helicobacter pylori." J. Biol. Chem. 272.34(1997):21357-21363.
GenBank Accession No. YP_211536, Mar. 10, 2005.
GenBank Accession No. AAD407131.1, Jun. 23, 1999.
GenBank Accession No. AAG29920, Nov. 6, 2000.
GenBank Accession No. AAG29921, Nov. 6, 2000.
GenBank Accession No. ADN91474, Sep. 28, 2010.
GenBank Accession No. AF194963, Feb. 20, 2003.
GenBank Accession No. AF285774.2, Nov. 27, 2015.
GenBank Accession No. BAA15899, Nov. 20, 2008.
GenBank Accession No. BAA15900, Nov. 20, 2008.
GenBank Accession No. BAA15913, Nov. 20, 2008.
GenBank Accession No. BAE76573, Nov. 20, 2008.
GenBank Accession No. BAE76575, Nov. 20, 2008.
GenBank Accession No. BAE76576, Nov. 20, 2008.
GenBank Accession No. BAE77265, Nov. 20, 2008.
GenBank Accession No. D00067, Jun. 15, 2010.
GenBank Accession No. E04821, Nov. 4, 2005.
GenBank Accession No. EF452503, Feb. 28, 2008.
GenBank Accession No. HV532291, Dec. 27, 2011.
GenBank Accession No. L20572, Mar. 17, 1994.
GenBank Accession No. M58003, Dec. 6, 1995.
GenBank Accession No. M84410, Apr. 27, 1993.
GenBank Accession No. V00295, Jul. 7, 1995.
GenBank Accession No. V00296, Apr. 18, 2005.
GenBank Accession No. X51872, Jul. 5, 1999.
Gilbert et al. "Biosynthesis of Ganglioside Mimics in Campylobacter jejuni OH4384. Identification of the Glycosyltransferase Genes, Enzymatic Synthesis of Model Compounds, and Characterization of Nanomole Amounts by 600-MHz 1H and 13C NMR Analysis." J. Biol. Chem. 275.6(2000):3896-3906.
Gilbert et al. "Characterization of a Recombinant Neisseria meningitidis a-2,3-Sialyltransferase and its Acceptor Specificity." Eur. J. Biochem. 249.1(1997):187-194.
Gilbert et al. "Cloning of the Lipooligosaccharide a-2,3-Sialyltransferase From the Bacterial Pathogens Neisseria meningitidis and Neisseria gonorrhoeae." J. Biol. Chem. 271.45(1996):28271-28276.
Gottesman et at "Regulation of Capsular Polysaccharide Synthesis in *Escherichia coli* K12." Mol. MicrobioL 5.7(1991):1599-1606.
Gupte et al. "Isolation and Characterization of rcsB Mutations that Affect Colanic Acid Capsule Synthesis in *Escherichia coli* K-12." J. Bacteria. 179.13(1997):4328-4335.
Hamosh. "Bioactive Factors in Human Milk." Pediatr. Clin. North Am. 48.1(2001):69-86.
Han et al. "Biotechnological Product of Human Milk Oligosaccharides." Biotechnol. Adv. 30.6(2012):1268-128.
Jeanneau et al. "Structure-Function Analysis of the Human Sialyltransferase ST3Gal I: Role of N-Glycosylation and a Novel Conserved Sialylmotif." J. Biol. Chem. 279.14(2004):13461-13468.
Johnson. "Synthesis of Oligosaccharides by Bacterial Enzymes." Glycoconj. J. 16.2(1999):141-146.
Koeller et al. "Synthesis of Complex Carbohydrates and Glycoconjugates: Enzyme-Based and Programmable One-Pot Strategies." Chem. Rev. 100.12(2000):4465-4494.
Koizumi et al. "Large-Scale Production of UDP-Galactose and Globotriose by Coupling Metabolically Engineered Bacteria." Nat. Biotechnol. 16.9(1998):847-850.
Kuhlenschmidt et al. "Sialic Acid Dependence and Independence of Group A Rotaviruses." Adv. Exp. Med. Biol. 473(1999):309-317.
Legaigneur et al. "Exploring the Acceptor Substrate Recognition of the Human 13-Galactoside a2,6-Sialyltransferase." J. Biol. Chem. 276.24(2001):21608-21617.
Li et al. "Characterization of a Novel a1,2-Fucosyltransferase of *Escherichia coli* 0128:B12 and Functional Investigation of its Common Motif." Biochem. 47.1(2008):378-387.
Li et al. "Identification of a New a1,2-Fucosyltransferase Involved in 0-Antigen Biosynthesis of *Escherichia coli* 086:B7 and Formation of H-Type 3 Blood Group Antigen." Biochem. 47.44(2008):11590-11597.
Ma et al. "A Single Aromatic Acid at the Carboxyl Terminus of Helicobacter pylori a1,3/4 Fucosyltransferase Determines Substrate Specificity." J. Biol. Chem. 280.44(2005):36848-36856.

(56) References Cited

OTHER PUBLICATIONS

Mandavi et al. "Helicobater pylori SabA Adhesin in Persistent Infection and Chronic Inflammation." Science. 297.5581(2002):573-578.
Martin et al. "Lewis X Biosynthesis in Helicobacter pylori. Molecular Cloning of an a(1,3)-Fucosyltransferase Gene." J. Biol. Chem. 272.34(1997):21349-21356.
Martin-Sosa et al. "Sialyloligosaccharides in Human and Bovine Milk and in Infant Formulas: Variations with the Progression of Lactation." J. Dairy Sci. 86.1(2003):52-59.
Mieschendahl et al. "A Novel Prophage Independent TRP Regulated A PL." Nat. Biotechnol. 4.9(1986):802-808.
Moran. "Relevance of Fucosylation and Lewis Antigen Expression in the Bacterial Gastroduodenal Pathogen Helicobacter pylori." Carbohydr. Res. 343.12(2008)1952-1965.
Morrow et al. "Human Milk Oligosaccharides are Associated with Protection Against Diarrhea in Breast-Fed Infants." J. Pediatr. 145.3(2004):297-303.
Newburg et al. "Innate Protection Conferred by Fucosylated Oligosaccharides of Human Milk Against Diarrhea in Breastfed Infants." Glycobiol. 14.3(2004):253-263.
Newburg et al. "Role of Human-Milk Lactadherin in Protection Against Symptomatic Rotavirus Infection." Lancet. 351. 9110(1998):1160-1164.
Newburg. "Bioactive Components of Human Milk: Evolution, Efficiency, and Protection." Adv. Exp. Med. Biol. 501(2001):3-10.
Newburg. "Human Milk Glycoconjugates that Inhibit Pathogens." Curr. Med. Chem. 6.2(1999):117-127.
Ninonuevo et al. "A Strategy for Annotating the Human Milk Glycome." J. Agric. Food Chem. 54.20(2006):7471-7480.
Palcic. "Biocatalytic Synthesis of Oligosacchrides." Curr. Opin. Biotechnol. 10.6(1999):616-624.
Parkkinen et al. "Isolation of Sialyl Oligosaccharides and Sialyl Oligosaccharide Phosphates from Bovine Colostrum and Human Urine." Meth. EnymoL 138(1987):289-300.
Rasko et al. "Cloning and Characterization of the a(1,3/4) Fucosyltransferase of Helicobacter pylori." J. Biol. Chem. 275. 7(2000):4988-4994.
Ringenberg et al. "Redirection of Sialic Acid Metabolism in Genetically Engineered *Escherichia coli.*" Glycobiol. 11.7(2001):533-539.
Roberfroid et al. "Prebiotic Effects: Metabolic and Health Benefits." Br. J. Nutr. 104.S2(2010):S1-S63.
Ruiz-Palacios et al. "Campylobacterijejuni Binds Intestinal H(0) Antigen (Fuc al, 2Gal (31, 4GlcNAc) and Fucosyloligosaccharides of Human Milk Inhibit its Binding and Infection." J. Biol. Chem. 278.16(2003):14112-14120.
Rydell et al. "Human Noroviruses Recognize Sialyl Lewis x Neoglycoprotein." Glycobiol. 19.3(2009):309-320.
Sanger et al. "Nucleotide Sequence of Bacteriophage A DNA." J. Mol. Biol. 162.4(1982):729-773.
Scharfman et al. "Sialyl-Lex and Suflo-Sialyl-Lex Determinants are Receptors for *P. aeruginosa.*" Glycoconj. J. 17.10(2000):735-740.
Seeberger. "Automated Carbohydrate Synthesis to Drive Chemical Glycomics." Chme. Commun. (Camb). 10(2003):1115-1121.
Shen et al. "Resolution of Structural Isomers of Sialylated Oligosaccharides by Capillary Electrophoresis." J. Chromatogr. A. 921. 2(2001):315-321.
Stevenson et al. "Organization of the *Escherichia coli* K-12 Gene Cluster Responsible for Production of the Extracellular Polysaccharide Colanic Acid." J. Bacteriol. 178.16(1996):4885-4893.
Taniguchi. "Promoter Structure and Transcriptional Regulation of Human 13-Galactoside a2, 3-Sialyltransferase Genes." Curr. Drug Targets. 9.4(2008):310-316.
Thomason et al. "*E. coli* Genome Manipulation by P1 Transduction." Curr. Protoc. Mol. Biol. Chapter 1, Unit 1.17(2007).
Tsai et al. "Influence of the Length of the Lipooligosaccharide a Chain on its Sialylation in the Neisseria meningitidis." Infect. Immun. 70.1(2002):407-411.
UniProt Accession No. P0A9M0 (Feb. 2008).

Wang et al. "Molecular Genetic Basis for the Variable Expression of Lewis Y Antigen in Helicobacter pylori: Analysis of the a (1,2) Fucosyltransferase Gene." Mol. Microbiol. 31.4(1999):1265-1274.
Ward et al. "In vitro Fermentability of Human Milk Oligosaccharides by Several Strains of Bifidobacteria." *Mol. Nutr. Food Res.* 51.11(2007):1398-1405.
Wymer et al. "Enzyme-Catalyzed Synthesis of Carbohydrates." Curr. Opin. Chem. Biol. 4.1(2000):110-119.
Zhang et al. "Helicobacter Hepaticus Hh0072 Gene Encodes a Novel al-3-Fucosyltransferase Belonging to CAZy GT11 Family." Glycobiol. 20.9(2010):1077-1088.
Albertson et al., Construction and use of a new vector/transposon, pLBT::mini-Tn10:lac:kan, to identify environmentally responsive genes in a marine bacterium. FEMS Microbiol Lett. Jul. 1, 1996;140(2-3):287-94.
Atkins et al., Low activity of-galactosidase in frameshift mutants of *Escherichia coli.* Proc Natl Acad Sci U S A. May 1972;69(5):1192-5.
Ebel et al., *Escherichia coli* RcsA, a positive activator of colanic acid capsular polysaccharide synthesis, functions To activate its own expression. J Bacteriol. Jan. 1999;181(2):577-84.
Ring et al., Multiple replacements establish the importance of tyrosine-503 in beta-galactosidase (*Escherichia coli*). Arch Biochem Biophys. Dec. 1990;283(2):342-50.
Xiong et al., Downstream deletion analysis of the lac promoter. J Bacteriol. Aug. 1991;173(15):4570-7.
Bachmann et al. (1972) "Pedigrees of Some Mutant Strains of *Escherichia coli* K-12," Bacteriological Reviews. 36 (4):525-557.
Beckwith (1983) "A Deletion Analysis of the Lac Operator Region in *Escherichia Coli*," Journal of Molecular Biology. 8:427-430.
Chaturvedi et al. (1997) "Milk oligosaccharide profiles by reversed-phase HPLC of their perbenzoylated derivatives," Anal Biochem. 251:89-97.
Chessa et al. (2009) "*Salmonella enterica* serotype Typhimurium Std fimbriae bind terminal alpha(1,2)fucose residues in the cecal mucosa," Mol Microbiol. 71:864-875.
Chin et al. (2015) "Enhanced Production of 2'-Fucosyllactose in Engineered *Escherichia Coli* BL21star(DE3) by Modulation of Lactose Metabolism and Fucosyltransferase," Journal of Biotechnology. 210:107-115.
Croucher et al. (Mar. 1983) "Bacterial Populations Associated with Different Regions of the Human Colon Wall," Applied and Environmental Microbiology. 45(3):1025-1033.
Duijts et al. (2009) "Breastfeeding protects against infectious diseases during infancy in industrialized countries; A systematic review," Matern Child Nutr. 5:199-210.
Dumon et al. (2004) "Assessment of the Two Helicobacter pylori α-1,3-Fucosyltransferase Ortholog Genes for the Large-Scale Synthesis of LewisX Human Milk Oligosaccharides by Metabolically Engineered *Escherichia coli*," Biotechnology Progress. 20(2):412-419.
Endo et al. (Oct. 1, 2000) "Large-Scale Production of Oligosaccharides Using Engineered Bacteria," Current Opinion in Structural Biology. 10(5):536-541.
Farag et al. (2007) "Helicobacter pylori infection is associated with severe anemia of pregnancy on Pemba Island, Zanzibar," Am J Trop Med Hyg. 76:541-548.
Fox et al. (2006) "Identification of a bifunctional lipopolysaccharide sialyltransferase in Haemophilus influenzae: incorporation of disialic acid," J Biol Chem. 281:40024-40032.
Foxall et al. (1992) "The three members of the selectin receptor family recognize a common carbohydrate epitope, the sialyl Lewis(x) oligosaccharide," J Cell Biol. 117:895-902.
GenBank Accession No. AC_000091.1, "*Escherichia coli* str. K-12 substr. W3110, complete sequence", Jun. 21, 2011, 12 pages. Accessible on the Internet at URL: https://www.ncbi.nlm.nih.gov/nuccore/AC_000091.1?report=genbank.
Gottsch et al. (2003) "Serial analysis of gene expression in the corneal endothelium of Fuchs' dystrophy," Investigative Ophthalmology & Visual Science. 44(2):594-599.
Hoban et al. (1958) "Gradient Elution of Disaccharides on Stearic Acid Treated Charcoal Column," Analytical Chemistry. 30(7):1294-1296.

(56) References Cited

OTHER PUBLICATIONS

Hood et al. (2001) "Identification of a lipopolysaccharide alpha-2,3-sialyltransferase from Haemophilus influenza," Mol Microbiol. 39:341-350.
Huang et al. (2003) "Noroviruses bind to human ABO, Lewis, and secretor histo-blood group antigens: identification of 4 distinct strain-specific patterns," J Infect Dis. 188:19-31.
Jiang et al. (2004) "Human milk contains elements that block binding of noroviruses to human histo-blood group antigens in saliva," J Infect Dis. 190:1850-1859.
Kivi et al. (2006) "Helicobacter pylori occurrence and transmission: a family affair?" Scand J Infect Dis. 38:407-417.
Ko et al. (2005) "Noroviruses as a cause of traveler's diarrhea among students from the United States visiting Mexico," J Clin Microbiol. 43:6126-6129.
Lavallie et al. (1993) "A Thioredoxin Gene Fusion Expression System that Circumvents Inclusion Body Formation in the *E coli* Cytoplasm," Bio/Technology. 11(2):187-193.
Li et al. (2007) "The Hd0053 gene of Haemophilus ducreyi encodes an [alpha] 2, 3-sialyltransferase," Biochemical and Biophysical Research Communications. 361:555-560.
Libster et al. (2009) "Breastfeeding prevents severe disease in full term female infants with acute respiratory infection," Pediatr Infect Dis J. 28:131-134.
Lindesmith et al. (2003) "Human susceptibility and resistance to Norwalk virus infection," Nat Med. 9:548-553.
Lorntz et al. (2006) "Early childhood diarrhea predicts impaired school performance," Pediatr Infect Dis J. 25:513-520.
Marcobal et al. (2010) "Consumption of human milk oligosaccharides by gut-related microbes," J Agric Food Chem. 58:5334-5340.
McCoy et al. (Oct. 1994) "Expression and Purification of Thioredoxin Fusion Proteins," Current Protocols in Molecular Biology. 16.8.1-16.8.14.
Miller (1972) "Assay of B-Galactosidas," Experiments in Molecular Genetics. 48:352-355.
Mitchell (2003) "Identification and Analysis of 'Extended-10' Promoters in *Escherichia Coli*," Nucleic Acids Research. 31(16):4689-4695.
Mohammad et al. (2008) "Prevalence of Helicobacter pylori infection among Egyptian children: impact of social background and effect on growth," Public Health Nutr. 11:230-236.
Morrow et al. (2004) "Human milk oligosaccharide blood group epitopes and innate immune protection against campylobacter and calicivirus diarrhea in breastfed infants," Adv Exp Med Biol. 554:443-446.
Morrow et al. (2005) "Human-milk glycans that inhibit pathogen binding protect breast-feeding infants against infectious diarrhea," J Nutr. 135:1304-1307.
Newburg et al. (2004) "Human milk alpha1,2-linked fucosylated oligosaccharides decrease risk of diarrhea due to stable toxin of *E. coli* in breastfed infants," Adv Exp Med Biol. 554:457-461.
Newburg et al. (2005) "Human milk glycans protect infants against enteric pathogens," Annu Rev Nutr. 25:37-58.
Newburg et al. (2007) "Protection of the neonate by the innate immune system of developing gut and of human milk," Pediatr Res. 61:2-8.
Oriá et al. (2009) "Semantic fluency: a sensitive marker for cognitive impairment in children with heavy diarrhea burdens?" Med Hypotheses. 73:682-686.
Petersson et al. (2006) "Helicobacter pylori SabA adhesin evokes a strong inflammatory response in human neutrophils which is down-regulated by the neutrophil-activating protein," Med Microbiol Immunol. 195:195-206.
Stepans et al. (2006) "Early consumption of human milk oligosaccharides is inversely related to subsequent risk of respiratory and enteric disease in infants," Breastfeed Med. 1:207-215.
Takakura et al. (2007) "Molecular cloning, expression and properties of an alpha/beta-Galactoside alpha2,3-sialyltransferase from Vibrio sp. JT-FAJ-16," J Biochem. 142:403-412.
Thomason et al. (Jan. 2015) "Global Transcriptional Start Site Differential RNA Sequencing Reveals Novel Antisense RNAs in *Escherichia coli*," Journal of Bacterilology. 197(1):18-28.
Tsukamoto et al. (2007) "Purification, cloning, and expression of an alpha/beta-galactoside alpha-2,3-sialyltransferase from a luminous marine bacterium, Photobacterium phosphoreum," J Biol Chem. 282:29794-29802.
Wang et al. (1999) "Novel Helicobacter Pylori $\alpha$1,2-Fucosyltransferase, a Key Enzyme in the Synthesis of Lewis Antigens," Microbiology. 145:3245-3253.
Ward et al. (Jun. 2006) "In Vitro Fermentation of Breast Milk Oligosaccharides by Bifidobacterium infantis and Lactobacillus gasseri," Applied and Environmental Microbiology. 72(6):4497-4499.
Xia et al. (2007) "Pseudomonas aeruginosa mucoid strain 8830 binds glycans containing the sialyl-Lewis x epitope," Glycoconj J. 24:87-95.
Giacomini et al. (1992) "Experimental conditions may affect reproducibility of the beta-galactosidase assay," FEMS Microbiology Letters. pp. 87-90.
Kawano et al. (2005) "Detection of low-level promoter activity within open reading frame sequences of *Escherichia coli*," Nucleic Acids Research. 33(19):6268-6276.
Slein et al. (1967) "Lysis of *Escherichia coli* by Ethylenediaminetetra-acetate and Phospholipases as Measured by beta-Galactosidase Activity," Journal of Bacteriology. 94(4):934-941.
Third-Party Submission under 37 CFR 1.290 Concise Description of Relevance for U.S. Appl. No. 15/980,349 dated Mar. 4, 2019 (106 pages).
Third Party Observation for European Patent Application No. 20120746649 dated Feb. 12, 2020 (8 pages).
Third-Party Submission for European Patent Application No. 12 746 649.8 dated Dec. 2, 2019 (5 pages).
Third-Party Submission for European Patent Application No. 12 746 649.8 dated Nov. 28, 2019 (3 Pages).
Third-Party Submission for European Patent Application No. 12 746 649.8 dated Oct. 4, 2018 (8 pages).
Third-party submission for EP Patent Application No. 12 746 649.8, dated May 27, 2020 (1 page).

\* cited by examiner

FIG. 3 Metabolic engineering for 2'-FL production in *E. coli*

FIG. 5  Pathway engineering for 3'-sialyllactose production in *E. coli*

FIG. 13A

```
LOCUS       W3110_delta_lon::Kan::lacZ_with_RBS    5049 bp    DNA
linear   BCT 19-FEB-2009
DEFINITION  Escherichia coli str. K-12 substr. W3110 strain K-12.
ACCESSION   AC_000091
VERSION     AC_000091.1  GI:89106884
KEYWORDS    .
SOURCE      Escherichia coli str. K-12 substr. W3110 (unknown)
  ORGANISM  Escherichia coli str. K-12 substr. W3110
            Bacteria; Proteobacteria; Gammaproteobacteria;
Enterobacteriales;
            Enterobacteriaceae; Escherichia.
FEATURES             Location/Qualifiers
     gene            1..112
                     /gene="clpX"
     CDS             1..112
                     /gene="clpX"
                     /note="ECK0432:JW0428:b0438"
                     /codon_start=1
                     /transl_table=11
                     /product="ATPase and specificity subunit of ClpX-ClpP
ATP-dependent serine protease"
                     /protein_id="AP_001088.1"
                     /db_xref="GI:89107308"
/translation="MTDKRKDGSGKLLYCSFCGKSQHEVRKLIAGPSVYICDECVDLC
NDIIREEIKEVAPHRERSALPTPHEIRNHLDDYVIGQEQAKKVLAVAVYNHYKRLRNG
DTSNGVELGKSNILLIGPTGSGKTLLAETLARLLDVPFTMADATTLTEAGYVGEDVEN
IIQKLLQKCDYDVQKAQRGIVYIDEIDKISRKSDNPSITRDVSGEGVQQALLKLIEGT
VAAVPPQGGRKHPQQEFLQVDTSKILFICGGAFAGLDKVISHRVETGSGIGFGATVKA
KSDKASEGELLAQVEPEDLIKFGLIPEFIGRLPVVATLNELSEEALIQILKEPKNALT
KQYQALFNLEGVDLEFRDEALDAIAKKAMARKTGARGLRSIVEAALLDTMYDLPSMED
VEKVVIDESVIDGQSKPLLIYGKPEAQQASGE" 
```
(SEQ ID NO: 9)
```
                     /label="clpX (partial gene)"
     host_DNA        1..302
                     /label="E. coli W3110 chromosome"
     source          1..302
                     /organism="Escherichia coli str. K-12 substr. W3110"
                     /mol_type="genomic DNA"
                     /strain="K-12"
                     /sub_strain="W3110"
                     /db_xref="taxon:316407"
     primer          258..302
                     /label="lon-H1 Lambda red homology region"
     gene            300..302
                     /gene="lon"
     CDS             300..302
                     /gene="lon"
                     /note="ECK0433:JW0429:b0439"
                     /codon_start=1
                     /transl_table=11
                     /product="DNA-binding ATP-dependent protease La"
                     /protein_id="AP_001089.1"
                     /db_xref="GI:89107309"
/translation="MNPERSERIEIPVLPLRDVVVYPHMVIPLFVGREKSIRCLEAAM
DHDKKIMLVAQKEASTDEPGVNDLFTVGTVASILQMLKLPDGTVKVLVEGLQRARISA
LSDNGEHFSAKAEYLESPTIDEREQEVLVRTAISQFEGYIKLNKKIPPEVLTSLNSID
DPARLADTIAAHMPLKLADKQSVLEMSDVNERLEYLMAMMESEIDLLQVEKRIRNRVK
KQMEKSQREYYLNEQMKAIQKELGEMDDAPDENEALKRKIDAAKMPKEAKEKAEAELQ
```

FIG. 13B

KLKMMSPMSAEATVVRGYIDWMVQVPWNARSKVKKDLRQAQEILDTDHYGLERVKDRI
LEYLAVQSRVNKIKGPILCLVGPPGVGKTSLGQSIAKATGRKYVRMALGGVRDEAEIR
GHRRTYIGSMPGKLIQKMAKVGVKNPLFLLDEIDKMSSDMRGDPASALLEVLDPEQNV
AFSDHYLEVDYDLSDVMFVATSNSMNIPAPLLDRMEVIRLSGYTEDEKLNIAKRHLLP
KQIERNALKKGELTVDDSAIIGIIRYYTREAGVRGLEREISKLCRKAVKQLLLDKSLK
HIEINGDNLHDYLGVQRFDYGRADNENRVGQVTGLAWTEVGGDLLTIETACVPGKGKL
TYTGSLGEVMQESIQAALTVVRARAEKLGINPDFYEKRDIHVHVPEGATPKDGPSAGI
AMCTALVSCLTGNPVRADVAMTGEITLRGQVLPIGGLKEKLLAAHRGGIKTVLIPFEN
KRDLEEIPDNVIADLDIHPVKRIEEVLTLALQNEPSGMQVVTAK" (SEQ ID NO: 10)

```
                          /label="lon N-terminus (initiator methionine codon
         only remains)"
         repeat_unit      303..330
                          /label="Flp site"
         primer_bind      303..322
                          /label="P4 wanner=P1 Baba and Mori"
         source           complement(303..1605)
                          /organism="Template plasmid pKD13"
                          /mol_type="genomic DNA"
                          /db_xref="taxon:170493"
         misc_feature     complement(303..4704)
                          /note="originates from KanR-lacZRBS-"
                          /label=Insert
         repeat_unit      331..364
                          /label="34 nt Flp site scar"
         repeat_unit      331..342
                          /label="Flp site"
         repeat_unit      complement(353..364)
                          /label="FLP site"
         Region           365..1586
                          /label="excised region upon pCP20 introduction"
         KAN_resistance   732..1526
                          /note="kanamycin resistance"
                          /codon_start=1
                          /transl_table=11
                          /product="Tn5 neomycin phosphotransferase"
                          /protein_id="AAL02037.1"
                          /db_xref="GI:15554336"
/translation="MIEQDGLHAGSPAAWVERLFGYDWAQQTIGCSDAAVFRLSAQGR
PVLFVKTDLSGALNELQDEAARLSWLATTGVPCAAVLDVVTEAGRDWLLLGEVPGQDL
LSSHLAPAEKVSIMADAMRRLHTLDPATCPFDHQAKHRIERARTRMEAGLVDQDDLDE
EHQGLAPAELFARLKARMPDGEDLVVTHGDACLPNIMVENGRFSGFIDCGRLGVADRY
QDIALATRDIAEEELGGEWADRFLVLYGIAAPDSQRIAFYRLLDEFF"(SEQ ID NO: 11)
         repeat_unit      1539..1550
                          /label="Flp site"
         misc_feature     1539..1586
                          /note="natural FRT site"
         repeat_unit      1553..1564
                          /label="Flp site"
         repeat_unit      complement(1575..1586)
                          /label="FLP site"
         primer_bind      complement(1586..1605)
                          /label="P1 Wanner=P2 Baba et al"
         repeat_unit      1587..1605
                          /label="Flp site downstream scar Baba et al"
         Site             join(1615^1616,1610..1617)
                          /note="Name: NotI"
                          /note="Pattern: gcggccgc"
                          /note="cut_0 on positive strand: 3083^3084"
                          /note="cut_0 on negative strand: 3087^3088"
                          /note="inhibited by: 5'; N4-methylcytosine"
                          /note="site_type: other"
```

FIG. 13C

```
               /note="restriction site"
               /label=NotI
  source       1618..4704
               /organism="Escherichia coli W3110"
               /mol_type="genomic DNA"
               /strain="K-12"
               /sub_strain="W3110"
               /db_xref="taxon:316407"
               /note="synonym: Escherichia coli str. K12 substr.
               W3110"
  wild_type_CDS  complement(1618..4692)
               /gene="lacZ"
               /note="ECK0341:JW0335:b0344"
               /codon_start=1
               /transl_table=11
               /product="beta-D-galactosidase"
               /protein_id="BAE76126.1"
               /db_xref="GI:85674486"
/translation="MTMITDSLAVVLQRRDWENPGVTQLNRLAAHPPFASWRNSEEAR
TDRPSQQLRSLNGEWRFAWFPAPEAVPESWLECDLPEADTVVVPSNWQMHGYDAPIYT
NVTYPITVNPPFVPTENPTGCYSLTFNVDESWLQEGQTRIIFDGVNSAFHLWCNGRWV
GYGQDSRLPSEFDLSAFLRAGENRLAVMVLRWSDGSYLEDQDMWRMSGIFRDVSLLHK
PTTQISDFHVATRFNDDFSRAVLEAEVQMCGELRDYLRVTVSLWQGETQVASGTAPFG
GEIIDERGGYADRVTLRLNVENPKLWSAEIPNLYRAVVELHTADGTLIEAEACDVGFR
EVRIENGLLLLNGKPLLIRGVNRHEHHPLHGQVMDEQTMVQDILLMKQNNFNAVRCSH
YPNHPLWYTLCDRYGLYVVDEANIETHGMVPMNRLTDDPRWLPAMSERVTRMVQRDRN
HPSVIIWSLGNESGHGANHDALYRWIKSVDPSRPVQYEGGGADTTATDIICPMYARVD
EDQPFPAVPKWSIKKWLSLPGETRPLILCEYAHAMGNSLGGFAKYWQAFRQYPRLQGG
FVWDWVDQSLIKYDENGNPWSAYGGDFGDTPNDRQFCMNGLVFADRTPHPALTEAKHQ
QQFFQFRLSGQTIEVTSEYLFRHSDNELLHWMVALDGKPLASGEVPLDVAPQGKQLIE
LPELPQPESAGQLWLTVRVVQPNATAWSEAGHISAWQQWRLAENLSVTLPAASHAIPH
LTTSEMDFCIELGNKRWQFNRQSGFLSQMWIGDKKQLLTPLRDQFTRAPLDNDIGVSE
ATRIDPNAWVERWKAAGHYQAEAALLQCTADTLADAVLITTAHAWQHQGKTLFISRKT
YRIDGSGQMAITVDVEVASDTPHPARIGLNCQLAQVAERVNWLGLGPQENYPDRLTAA
CFDRWDLPLSDMYTPYVFPSENGLRCGTRELNYGPHQWRGDFQFNISRYSQQQLMETS
HRHLLHAEEGTWLNIDGFHMGIGGDDSWSPSVSAEFQLSAGRYHYQLVWCQK"(SEQ ID NO: 12)
               /label="wild-type lacZ+ CDS"
  epitope_tag  complement(4671..4704)
               /label="LacFKpnInoRBS cloning primer"
  RBS          complement(4693..4704)
  gene         <4705..4725
               /gene="lon"
  CDS          <4705..4725
               /gene="lon"
               /note="ECK0433:JW0429:b0439"
               /codon_start=1
               /transl_table=11
               /product="DNA-binding ATP-dependent protease La"
               /protein_id="AP_001089.1"
               /db_xref="GI:89107309"
/translation="MNPERSERIEIPVLPLRDVVVYPHMVIPLFVGREKSIRCLEAAM
DHDKKIMLVAQKEASTDEPGVNDLFTVGTVASILQMLKLPDGTVKVLVEGLQRARISA
LSDNGEHFSAKAEYLESPTIDEREQEVLRTAISQFEGYIKLNKKIPPEVLTSLNSID
DPARLADTIAAHMPKLADKQSVLEMSDVNERLEYLMAMMESEIDLLQVEKRIRNRVK
KQMEKSQREYYLNEQMKAIQKELGEMDDAPDENEALKRKIDAAKMPKEAKEKAEAELQ
KLKMMSPMSAEATVVRGYIDWMVQVPWNARSKVKKDLRQAQEILDTHYGLERVKDRI
LEYLAVQSRVNKIKGPILCLVGPPGVGKTSLGQSIAKATGRKYVRMALGGVRDEAEIR
GHRRTYIGSMPGKLIQKMAKVGVKNPLFLLDEIDKMSSDMRGDPASALLEVLDPEQNV
AFSDHYLEVDYDLSDVMFVATSNSMNIPAPLLDRMEVIRLSGYTEDEKLNIAKRHLLP
KQIERNALKKGELTVDDSAIIGIIRYYTREAGVRGLEREISKLCRKAVKQLLLDKSLK
```

FIG. 13D

```
HIEINGDNLHDYLGVQRFDYGRADNENRVGQVTGLAWTEVGGDLLTIETACVPGKGKL
TYTGSLGEVMQESIQAALTVVRARAEKLGINPDFYEKRDIHVHVPEGATPKDGPSAGI
AMCTALVSCLTGNPVRADVAMTGEITLRGQVLPIGGLKEKLLAAHRGGIKTVLIPFEN
KRDLEEIPDNVIADLDIHPVKRIEEVLTLALQNEPSGMQVVTAK" (SEQ ID NO: 13)
                      /label="lon C-terminus (encodes 6 C-terminal
residues)"
     host_DNA         4705..5049
                      /label="E. coli W3110 chromosome"
        source        <4705..>5049
                      /organism="Escherichia coli str. K-12 substr. W3110"
                      /mol_type="genomic DNA"
                      /strain="K-12"
                      /sub_strain="W3110"
                      /db_xref="taxon:316407"
     primer           complement(4705..4749)
                      /label="lon-H2 homology region for lambda red"
        gene          4934..>5049
                      /gene="hupB"
        CDS           4934..>5049
                      /gene="hupB"
                      /note="ECK0434:JW0430:b0440"
beta subunit"         /codon_start=1
                      /transl_table=11
                      /product="HU, DNA-binding transcriptional regulator,
                      /protein_id="AP_001090.1"
                      /db_xref="GI:89107310"
/translation="MNKSQLIDKIAAGADISKAAAGRALDAIIASVTESLKEGDDVAL
VGFGTFAVKERAARTGRNPQTGKEITIAAAKVPSFRAGKALKDAVN"(SEQ ID NO: 14)
                      /label="hupB (partial gene)"
ORIGIN
   1 GTCCATGGAA GACGTCGAAA AAGTGGTTAT CGACGAGTCG GTAATTGATG GTCAAAGCAA
  61 ACCGTTGCTG ATTTATGGCA AGCCGGAAGC GCAACAGGCA TCTGGTGAAT AATTAACCAT
 121 TCCCATACAA TTAGTTAACC AAAAAGGGGG GATTTTATCT CCCCTTTAAT TTTTCCTCTA
 181 TTCTCGGCGT TGAATGTGGG GGAAACATCC CCATATACTG ACGTACATGT TAATAGATGG
 241 CGTGAAGCAC AGTCGTGTCA TCTGATTACC TGGCGGAAAT TAAACTAAGA GAGAGCTCTA
 301 TGATTCCGGG GATCCGTCGA CCTGCAGTTC GAAGTTCCTA TTCTCTAGAA AGTATAGGAA
 361 CTTCAGAGCG CTTTTGAAGC TCACGCTGCC GCAAGCACTC AGGGCGCAAG GGCTGCTAAA
 421 GGAAGCGGAA CACGTAGAAA GCCAGTCCGC AGAAACGTG CTGACCCCGG ATGAATGTCA
 481 GCTACTGGGC TATCTGGACA AGGGAAAACG CAAGCGCAAA GAGAAAGCAG GTAGCTTGCA
 541 GTGGGCTTAC ATGGCGATAG CTAGACTGGG CGGTTTTATG GACAGCAAGC GAACCGGAAT
 601 TGCCAGCTGG GGCGCCCTCT GGTAAGGTTG GGAAGCCCTG CAAAGTAAAC TGGATGGCTT
 661 TCTTGCCGCC AAGGATCTGA TGGCGCAGGG GATCAAGATC TGATCAAGAG ACAGGATGAG
 721 GATCGTTTCG CATGATTGAA CAAGATGGAT TGCACGCAGG TTCTCCGGCC GCTTGGGTGG
 781 AGAGGCTATT CGGCTATGAC TGGGCACAAC AGACAATCGG CTGCTCTGAT GCCGCCGTGT
 841 TCCGGCTGTC AGCGCAGGGG CGCCCGGTTC TTTTTGTCAA GACCGACCTG TCCGGTGCCC
 901 TGAATGAACT GCAGGACGAG GCAGCGCCGC TATCGGTGCT GGCCACGACG GGCGTTCCTT
 961 GCGCAGCTGT GCTCGACGTT GTCACTGAAG CGGGAAGGGA CTGGCTGCTA TTGGGCGAAG
1021 TGCCGGGGCA GGATCTCCTG TCATCTCACC TTGCTCCTGC CGAGAAAGTA TCCATCATGG
1081 CTGATGCAAT GCGGCGGCTG CATACGCTTG ATCCGGCTAC CTGCCCATTC GACCACCAAG
1141 CGAAACATCG CATCGAGCGA GCACGTACTC GGATGGAAGC CGGTCTTGTC GATCAGGATG
1201 ATCTGGACGA AGAGCATCAG GGGCTCGCGC CAGCCGAACT GTTCGCCAGG CTCAAGGCGC
1261 GCATGCCCGA CGGCGAGGAT CTCGTCGTGA CCCATGGCGA TGCCTGCTTG CCAATATCA
1321 TGGTGGAAAA TGGCCGCTTT TCTGGATTCA TCGACTGTGG CCGGCTGGGT GTGGCGGACC
1381 GCTATCAGGA CATAGCGTTG GCTACCCGTG ATATTGCTGA AGAGCTTGGC GGCGAATGGG
1441 CTGACCGCTT CCTCGTGCTT TACGGTATCG CCGCTCCCGA TTCGCAGCGC ATCGCCTTCT
1501 ATCGCCTTCT TGACGAGTTC TTCTAATAAG GGGATCTTGA AGTTCCTATT CCGAAGTTCC
1561 TATTCTCTAG AAAGTATAGG AACTTCGAAG CAGCTCCAGC CTACATAAAG CGGCCGCTTA
1621 TTTTGACAC CAGACCAACT GGTAATGGTA GCGACCGGCG CTCAGCTGGA ATTCGCCGA
1681 TACTGACGGG CTCCAGGAGT CGTCGCCACC AATCCCCATA TGGAAACCGT CGATATTCAG
1741 CCATGTGCCT TCTTCCGCGT GCAGCAGATG GCGATGGCTG GTTTCCATCA GTTGCTGTTG
```

FIG. 13E

```
1801 ACTGTAGCGG CTGATGTTGA ACTGGAAGTC GCCGCGCCAC TGGTGTGGGC CATAATTCAA
1861 TTCGCGCGTC CCGCAGCGCA GACCGTTTTC GCTCGGGAAG ACGTACGGGG TATACATGTC
1921 TGACAATGGC AGATCCCAGC GGTCAAAACA GGCGGCAGTA AGGCGGTCGG GATAGTTTTC
1981 TTGCGGCCCT AATCCGAGCC AGTTTACCCG CTCTGCTACC TGCGCCAGCT GGCAGTTCAG
2041 GCCAATCCGC GCCGGATGCG GTGTATCGCT CGCCACTTCA ACATCAACGG TAATCGCCAT
2101 TTGACCACTA CCATCAATCC GGTAGGTTTT CCGGCTGATA AATAAGGTTT TCCCCTGATG
2161 CTGCCACGCG TGAGCGGTCG TAATCAGCAC CGCATCAGCA AGTGTATCTG CCGTGCACTG
2221 CAACAACGCT GCTTCGGCCT GGTAATGGCC CGCCGCCTTC CAGCGTTCGA CCCAGGCGTT
2281 AGGGTCAATG CGGGTCGCTT CACTTACGCC AATGTCGTTA TCCAGCGGTG CACGGGTGAA
2341 CTGATCGCGC AGCGGCGTCA GCAGTTGTTT TTTATCGCCA ATCCACATCT GTGAAAGAAA
2401 GCCTGACTGG CGGTTAAATT GCCAACGCTT ATTACCAGC TCGATGCAAA AATCCATTTC
2461 GCTGGTGGTC AGATGCGGGA TGGCGTGGGA CGCGGCGGGG AGCGTCACAC TGAGGTTTTC
2521 CGCCAGACGC CACTGCTGCC AGGCGCTGAT GTGCCCGGCT TCTGACCATG CGGTCGCGTT
2581 CGGTTGCACT ACGCGTACTG TGAGCCAGAG TTGCCCGGCG CTCTCCGGCT GCGGTAGTTC
2641 AGGCAGTTCA ATCAACTGTT TACCTTGTGG AGCGACATCC AGAGGCACTT CACCGCTTGC
2701 CAGCGGCTTA CCATCAGCG CCACCATCCA GTGCAGGAGC TCGTTATCGC TATGACGGAA
2761 CAGGTATTCG CTGGTCACTT CGATGGTTTG CCCGGATAAA CGGAACTGGA AAAACTGCTG
2821 CTGGTGTTTT GCTTCCGTCA GCGCTGGATG CGGCGTGCGG TCGGCAAAGA CCAGACCGTT
2881 CATACAGAAC TGGCGATCGT TCGGCGTATC GCCAAAATCA CCGCCGTAAG CCGACCACGG
2941 GTTGCCGTTT TCATCATATT TAATCAGCGA CTGATCCACC CAGTCCCAGA CGAAGCCGCC
3001 CTGTAAACGG GGATACTGAC GAAACGCCTG CCAGTATTTA GCGAAACCGC CAAGACTGTT
3061 ACCCATCGCG TGGGCGTATT CGCAAAGGAT CAGCGGGCGC GTCTCTCCAG GTAGCGAAAG
3121 CCATTTTTTG ATGGACCATT TCGGCACAGC CGGGAAGGGC TGGTCTTCAT CCACGCGCGC
3181 GTACATCGGG CAAATAATAT CGGTGGCCGT GGTGTCGGCT CCGCCGCCTT CATACTGCAC
3241 CGGGCGGGAA GGATCGACAG ATTTGATCCA GCGATACAGC GCGTCGTGAT TAGCGCCGTG
3301 GCCTGATTCA TTCCCAGCG ACCAGATGAT CACACTCGGG TGATTACGAT CGCGCTGCAC
3361 CATTCGCGTT ACGCGTTCGC TCATCGCCGG TAGCCAGCGC GGATCATCGG TCAGACGATT
3421 CATTGGCACC ATGCCGTGGG TTTCAATATT GGCTTCATCC ACCACATACA GGCCGTAGCG
3481 GTCGCACAGC GTGTACCACA GCGGATGGTT CGGATAATGC GAACAGCGCA CGGCGTTAAA
3541 GTTGTTCTGC TTCATCAGCA GGATATCCTG CACCATCGTC TGCTCATCCA TGACCTGACC
3601 ATGCAGAGGA TGATGCTCGT GACGGTTAAC GCCTCGAATC AGCAACGGCT TGCCGTTCAG
3661 CAGCAGCAGA CCATTTTCAA TCCGCACCTC GCGGAAACCG ACATCGCAGG CTTCTGCTTC
3721 AATCAGCGTG CCGTCGGCGG TGTGCAGTTC AACCACCGCA CGATAGAGAT TCGGGATTTC
3781 GGCGCTCCAC AGTTTCGGGT TTTCGACGTT CAGACGTAGT GTGACGCGAT CGGCATAACC
3841 ACCACGCTCA TCGATAATTT CACCGCCGAA AGGCGCGGTG CCGCTGGCGA CCTGCGTTTC
3901 ACCCTGCCAT AAAGAAACTG TTACCCGTAG GTAGTCACGC AACTCGCCGC ACATCTGAAC
3961 TTCAGCCTCC AGTACAGCGC GGCTGAAATC ATCATTAAAG CGAGTGGCAA CATGGAAATC
4021 GCTGATTTGT GTAGTCGGTT TATGCAGCAA CGAGACGTCA CGGAAAATGC CGCTCATCCG
4081 CCACATATCC TGATCTTCCA GATAACTGCC GTCACTCCAG CGCAGCACCA TCACCGCGAG
4141 GCGGTTTTCT CCGGCGCGTA AAAATGCGCT CAGGTCAAAT TCAGACGGCA AACGACTGTC
4201 CTGGCCGTAA CCGACCCAGC GCCCGTTGCA CCACAGATGA AACGCCGAGT TAACGCCATC
4261 AAAAATAATT CGCGTCTGGC CTTCCTGTAG CCAGCTTTCA TCAACATTAA ATGTGAGCGA
4321 GTAACAACCC GTCGGATTCT CCGTGGGAAC AAACGGCGGA TTGACCGTAA TGGGATAGGT
4381 CACGTTGGTG TAGATGGGCG CATCGTAACC GTGCATCTGC CAGTTTGAGG GGACGACGAC
4441 AGTATCGGCC TCAGGAAGAT CGCACTCCAG CCAGCTTTCC GGCACCGCTT CTGGTGCCGG
4501 AAACCAGGCA AAGCGCCATT CGCCATTCAG GCTGCGCAAC TGTTGGGAAG GGCGATCGGT
4561 GCGGGCCTCT TCGCTATTAC GCCAGCTGGC GAAAGGGGA TGTGCTGCAA GGCGATTAAG
4621 TTGGGTAACG CCAGGGTTTT CCCAGTCACG ACGTTGTAAA ACGACGGCCA GTGAATCCGT
4681 AATCATGGTC ATAgtaggtt tcctCAGGTT GTGACTGCAA AATAGTGACC TCGCGCAAAA
4741 TGCACTAATA AAAACAGGGC TGGCAGGCTA ATTCGGGCTT GCCAGCCTTT TTTTGTCTCG
4801 CTAAGTTAGA TGGCGGATCG GGCTTGCCCT TATTAAGGGG TGTTGTAAGG GGATGGCTGG
4861 CCTGATATAA CTGCTGCGCG TTCGTACCTT GAAGGATTCA AGTGCGATAT AAATTATAAA
4921 GAGGAAGAGA AGAGTGAATA AATCTCAATT GATCGACAAG ATTGCTGCAG GGGCTGATAT
4981 CTCTAAAGCT GCGGCTGGCC GTGCGTTAGA TGCTATTATT GCTTCCGTAA CTGAATCTCT
5041 GAAAGAAGG (SEQ ID NO: 15)
```

E.coli strains of the current invention

| | | | | |
|---|---|---|---|---|
| E100 (GI724) | ampC::(P$_{trpB}$λcI+) | lacI$^q$ac P$_{L8}$ | | |
| E183 | ampC::(P$_{trpB}$λcI+) | P$_{lacI}$$^q$(ΔlacI-lacZ)$_{158}$lacY$^+$ | | |
| E205 | ampC::(P$_{trpB}$λcI+) | P$_{lacI}$$^q$(ΔlacI-lacZ)$_{158}$lacY$^+$ | ΔwcaJ | |
| E214 | ampC::(P$_{trpB}$λcI+) | P$_{lacI}$$^q$(ΔlacI-lacZ)$_{158}$lacY$^+$ | ΔwcaJ | thyA$_{748}$::Tn10 |
| E390 | ampC::(P$_{trpB}$λcI+) | P$_{lacI}$$^q$(ΔlacI-lacZ)$_{158}$lacY$^+$ | ΔwcaJ | thyA$_{748}$::Tn10 | Δlon::(kan,lacZ$^+$) |
| E403 | ampC::(P$_{trpB}$λcI+) | P$_{lacI}$$^q$(ΔlacI-lacZ)$_{158}$lacY$^+$ | ΔwcaJ | thyA$_{748}$::Tn10 | Δlon::(kan,lacZ$^+$) | ΔlacA |

FIG. 14

Comparison of expression levels at 37C of futC and wcfW in E.coli strain E390

2'-FL production directed by pG171 (futC-MYC)
or pG180 (wcfW-MYC) in *E.coli* strain E390:
inductions performed at 20C, 30C or 37C cytoplasmic extracts run on TLC

BIOSYNTHESIS OF HUMAN MILK OLIGOSACCHARIDES IN ENGINEERED BACTERIA

RELATED APPLICATIONS

This application is a continuation of U.S. Ser. No. 14/033,664 filed Sep. 23, 2013, now U.S. Pat. No. 9,587,241 issued Mar. 7, 2017, which is a divisional of U.S. Ser. No. 13/398,526 filed Feb. 16, 2012, now U.S. Pat. No. 9,453,230 issued Sep. 27, 2016, and claims the benefit of priority under 35 U.S.C. § 119(e) to U.S. Provisional Application No. 61/443,470, filed Feb. 16, 2011, the entire contents of each of which are incorporated herein by reference.

INCORPORATED-BY-REFERENCE OF SEQUENCE LISTING

The contents of the text file named "37847-505C01US_Sequence_Listing.txt", which was created on Jan. 26, 2017 and is 94 KB in size, are hereby incorporated by reference in their entirety.

FIELD OF THE INVENTION

The invention provides compositions and methods for producing purified oligosaccharides, in particular certain fucosylated and/or sialylated oligosaccharides that are typically found in human milk.

BACKGROUND OF THE INVENTION

Human milk contains a diverse and abundant set of neutral and acidic oligosaccharides (human milk oligosaccharides, HMOS). Many of these molecules are not utilized directly by infants for nutrition, but they nevertheless serve critical roles in the establishment of a healthy gut microbiome, in the prevention of disease, and in immune function. Prior to the invention described herein, the ability to produce HMOS inexpensively at large scale was problematic. For example, HMOS production through chemical synthesis was limited by stereo-specificity issues, precursor availability, product impurities, and high overall cost. As such, there is a pressing need for new strategies to inexpensively manufacture large quantities of HMOS for a variety of commercial applications.

SUMMARY OF THE INVENTION

The invention described herein features efficient and economical methods for producing fucosylated and sialylated oligosaccharides. The method for producing a fucosylated oligosaccharide in a bacterium comprises the following steps: providing a bacterium that comprises a functional β-galactosidase gene, an exogenous fucosyltransferase gene, a GDP-fucose synthesis pathway, and a functional lactose permease gene; culturing the bacterium in the presence of lactose; and retrieving a fucosylated oligosaccharide from the bacterium or from a culture supernatant of the bacterium.

To produce a fucosylated oligosaccharide by biosynthesis, the bacterium utilizes an endogenous or exogenous guanosine diphosphate (GDP)-fucose synthesis pathway. By "GDP-fucose synthesis pathway" is meant a sequence of reactions, usually controlled and catalyzed by enzymes, which results in the synthesis of GDP-fucose. An exemplary GDP-fucose synthesis pathway in *Escherichia coli* is set forth below. In the GDP-fucose synthesis pathway set forth below, the enzymes for GDP-fucose synthesis include: 1) manA=phosphomannose isomerase (PMI), 2) manB=phosphomannomutase (PMM), 3) manC=mannose-1-phosphate guanylyltransferase (GMP), 4) gmd=GDP-mannose-4,6-dehydratase (GMD), 5) fcl=GDP-fucose synthase (GFS), and 6) ΔwcaJ=mutated UDP-glucose lipid carrier transferase.

Glucose→Glc-6-P→Fru-6-P→¹Man-6-P→²Man-1-P→GDP-Man-⁴,⁵GDP-Fuc 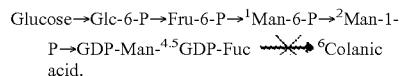 ⁶Colanic acid.

The synthetic pathway from fructose-6-phosphate, a common metabolic intermediate of all organisms, to GDP-fucose consists of 5 enzymatic steps: 1) PMI (phosphomannose isomerase), 2) PMM (phosphomannomutase), 3) GMP (mannose-1-phosphate guanylyltransferase), 4) GMD (GDP-mannose-4,6-dehydratase), and 5) GFS (GDP-fucose synthase). Individual bacterial species possess different inherent capabilities with respect to GDP-fucose synthesis. *Escherichia coli*, for example, contains enzymes competent to perform all five steps, whereas *Bacillus licheniformis* is missing enzymes capable of performing steps 4 and 5 (i.e., GMD and GFS). Any enzymes in the GDP-synthesis pathway that are inherently missing in any particular bacterial species are provided as genes on recombinant DNA constructs, supplied either on a plasmid expression vector or as exogenous genes integrated into the host chromosome.

The invention described herein details the manipulation of genes and pathways within bacteria such as the enterobacterium *Escherichia coli* K12 (*E. coli*) or probiotic bacteria leading to high level synthesis of HMOS. A variety of bacterial species may be used in the oligosaccharide biosynthesis methods, for example *Erwinia herbicola* (*Pantoea agglomerans*), *Citrobacter freundii*, *Pantoea citrea*, *Pectobacterium carotovorum*, or *Xanthomonas campestris*. Bacteria of the genus *Bacillus* may also be used, including *Bacillus subtilis*, *Bacillus licheniformis*, *Bacillus coagulans*, *Bacillus thermophilus*, *Bacillus laterosporus*, *Bacillus megaterium*, *Bacillus mycoides*, *Bacillus pumilus*, *Bacillus lentus*, *Bacillus cereus*, and *Bacillus circulans*. Similarly, bacteria of the genera *Lactobacillus* and *Lactococcus* may be modified using the methods of this invention, including but not limited to *Lactobacillus acidophilus*, *Lactobacillus salivarius*, *Lactobacillus plantarum*, *Lactobacillus helveticus*, *Lactobacillus delbrueckii*, *Lactobacillus rhamnosus*, *Lactobacillus bulgaricus*, *Lactobacillus crispatus*, *Lactobacillus gasseri*, *Lactobacillus casei*, *Lactobacillus reuteri*, *Lactobacillus jensenii*, and *Lactococcus lactis*. *Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum*, *Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*). Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

The bacterium also comprises a functional β-galactosidase gene. The β-galactosidase gene is an endogenous β-galactosidase gene or an exogenous β-galactosidase gene.

For example, the β-galactosidase gene comprises an *E. coli* lacZ gene (e.g., GenBank Accession Number V00296 (GI: 41901), incorporated herein by reference). The bacterium accumulates an increased intracellular lactose pool, and produces a low level of β-galactosidase.

A functional lactose permease gene is also present in the bacterium. The lactose permease gene is an endogenous lactose permease gene or an exogenous lactose permease gene. For example, the lactose permease gene comprises an *E. coli* lacY gene (e.g., GenBank Accession Number V00295 (GI:41897), incorporated herein by reference). Many bacteria possess the inherent ability to transport lactose from the growth medium into the cell, by utilizing a transport protein that is either a homolog of the *E. coli* lactose permease (e.g., as found in *Bacillus licheniformis*), or a transporter that is a member of the ubiquitous PTS sugar transport family (e.g., as found in *Lactobacillus casei* and *Lactobacillus rhamnosus*). For bacteria lacking an inherent ability to transport extracellular lactose into the cell cytoplasm, this ability is conferred by an exogenous lactose transporter gene (e.g., *E. coli* lacY) provided on recombinant DNA constructs, and supplied either on a plasmid expression vector or as exogenous genes integrated into the host chromosome.

The bacterium comprises an exogenous fucosyltransferase gene. For example, the exogenous fucosyltransferase gene encodes α(1,2) fucosyltransferase and/or α(1,3) fucosyltransferase. An exemplary α(1,2) fucosyltransferase gene is the wcfW gene from *Bacteroides fragilis* NCTC 9343 (SEQ ID NO: 4). An exemplary α(1,3) fucosyltransferase gene is the *Helicobacter pylori* 26695 futA gene. One example of the *Helicobacter pylori* futA gene is presented in GenBank Accession Number HV532291 (GI:365791177), incorporated herein by reference.

Alternatively, a method for producing a fucosylated oligosaccharide by biosynthesis comprises the following steps: providing an enteric bacterium that comprises a functional β-galactosidase gene, an exogenous fucosyltransferase gene, a mutation in a colanic acid synthesis gene, and a functional lactose permease gene; culturing the bacterium in the presence of lactose; and retrieving a fucosylated oligosaccharide from the bacterium or from a culture supernatant of the bacterium.

To produce a fucosylated oligosaccharide by biosynthesis, the bacterium comprises a mutation in an endogenous colanic acid (a fucose-containing exopolysaccharide) synthesis gene. By "colanic acid synthesis gene" is meant a gene involved in a sequence of reactions, usually controlled and catalyzed by enzymes that result in the synthesis of colanic acid. Exemplary colanic acid synthesis genes include an rcsA gene (e.g., GenBank Accession Number M58003 (GI: 1103316), incorporated herein by reference), an rcsB gene, (e.g., GenBank Accession Number E04821 (GI:2173017), incorporated herein by reference), a wcaJ gene, (e.g., GenBank Accession Number (amino acid) BAA15900 (GI: 1736749), incorporated herein by reference), a wzxC gene, (e.g., GenBank Accession Number (amino acid) BAA15899 (GI:1736748), incorporated herein by reference), a wcaD gene, (e.g., GenBank Accession Number (amino acid) BAE76573 (GI:85675202), incorporated herein by reference), a wza gene, (e.g., GenBank Accession Number (amino acid) BAE76576 (GI:85675205), incorporated herein by reference), a wzb gene, and (e.g., GenBank Accession Number (amino acid) BAE76575 (GI:85675204), incorporated herein by reference), and a wzc gene (e.g., GenBank Accession Number (amino acid) BAA15913 (GI: 1736763), incorporated herein by reference).

This is achieved through a number of genetic modifications of endogenous *E. coli* genes involved either directly in colanic acid precursor biosynthesis, or in overall control of the colanic acid synthetic regulon. Specifically, the ability of the host *E. coli* strain to synthesize colanic acid, an extracellular capsular polysaccharide, is eliminated by the deletion of the wcaJ gene, encoding the UDP-glucose lipid carrier transferase. In a wcaJ null background, GDP-fucose accumulates in the *E. coli* cytoplasm. Over-expression of a positive regulator protein, RcsA, in the colanic acid synthesis pathway results in an increase in intracellular GDP-fucose levels. Over-expression of an additional positive regulator of colanic acid biosynthesis, namely RcsB, is also utilized, either instead of or in addition to over-expression of RcsA, to increase intracellular GDP-fucose levels. Alternatively, colanic acid biosynthesis is increased following the introduction of a null mutation into the *E. coli* ion gene (e.g., GenBank Accession Number L20572 (GI:304907), incorporated herein by reference). Lon is an adenosine-5'-triphosphate (ATP)-dependant intracellular protease that is responsible for degrading RcsA, mentioned above as a positive transcriptional regulator of colanic acid biosynthesis in *E. coli*. In a ion null background, RcsA is stabilized, RcsA levels increase, the genes responsible for GDP-fucose synthesis in *E. coli* are up-regulated, and intracellular GDP-fucose concentrations are enhanced.

For example, the bacterium further comprises a functional, wild-type *E. coli* lacZ$^+$ gene inserted into an endogenous gene, for example the ion gene in *E. coli*. In this manner, the bacterium may comprise a mutation in a ion gene.

The bacterium also comprises a functional β-galactosidase gene. The β-galactosidase gene is an endogenous β-galactosidase gene or an exogenous β-galactosidase gene. For example, the β-galactosidase gene comprises an *E. coli* lacZ gene. The endogenous lacZ gene of the *E. coli* is deleted or functionally inactivated, but in such a way that expression of the downstream lactose permease (lacY) gene remains intact.

The bacterium comprises an exogenous fucosyltransferase gene. For example, the exogenous fucosyltransferase gene encodes α(1,2) fucosyltransferase and/or α(1,3) fucosyltransferase. An exemplary α(1,2) fucosyltransferase gene is the wcfW gene from *Bacteroides fragilis* NCTC 9343 (SEQ ID NO: 4). An exemplary α(1,3) fucosyltransferase gene is the *Helicobacter pylori* 26695 futA gene. One example of the *Helicobacter pylori* futA gene is presented in GenBank Accession Number HV532291 (GI:365791177), incorporated herein by reference.

A functional lactose permease gene is also present in the bacterium. The lactose permease gene is an endogenous lactose permease gene or an exogenous lactose permease gene. For example, the lactose permease gene comprises an *E. coli* lacY gene.

The bacterium may further comprise an exogenous rcsA and/or rcsB gene (e.g., in an ectopic nucleic acid construct such as a plasmid), and the bacterium optionally further comprises a mutation in a lacA gene (e.g., GenBank Accession Number X51872 (GI:41891), incorporated herein by reference).

Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

The bacteria used herein to produce HMOS are genetically engineered to comprise an increased intracellular guanosine diphosphate (GDP)-fucose pool, an increased intracellular lactose pool (as compared to wild type) and to comprise fucosyl transferase activity. Accordingly, the bacterium contains a mutation in a colanic acid (a fucose-containing exopolysaccharide) synthesis pathway gene, such as a wcaJ gene, resulting in an enhanced intracellular GDP-fucose pool. The bacterium further comprises a functional, wild-type E. coli lacZ$^+$ gene inserted into an endogenous gene, for example the ion gene in E. coli. In this manner, the bacterium may further comprise a mutation in a ion gene. The endogenous lacZ gene of the E. coli is deleted or functionally inactivated, but in such a way that expression of the downstream lactose permease (lacY) gene remains intact. The organism so manipulated maintains the ability to transport lactose from the growth medium, and to develop an intracellular lactose pool for use as an acceptor sugar in oligosaccharide synthesis, while also maintaining a low level of intracellular beta-galactosidase activity useful for a variety of additional purposes. The bacterium may further comprise an exogenous rcsA and/or rcsB gene (e.g., in an ectopic nucleic acid construct such as a plasmid), and the bacterium optionally further comprises a mutation in a lacA gene. Preferably, the bacterium accumulates an increased intracellular lactose pool, and produces a low level of beta-galactosidase.

The bacterium possesses fucosyl transferase activity. For example, the bacterium comprises one or both of an exogenous fucosyltransferase gene encoding an α(1,2) fucosyltransferase and an exogenous fucosyltransferase gene encoding an α(1,3) fucosyltransferase. An exemplary α(1,2) fucosyltransferase gene is the wcfW gene from Bacteroides fragilis NCTC 9343 (SEQ ID NO: 4). Prior to the present invention, this wcfW gene was not known to encode a protein with an α(1,2) fucosyltransferase activity, and further was not suspected to possess the ability to utilize lactose as an acceptor sugar. Other α(1,2) fucosyltransferase genes that use lactose as an acceptor sugar (e.g., the Helicobacter pylori 26695 futC gene or the E. coli O128:B12 wbsJ gene) may readily be substituted for Bacteroides fragilis wcfW. One example of the Helicobacter pylori futC gene is presented in GenBank Accession Number EF452503 (GI: 134142866), incorporated herein by reference.

An exemplary α(1,3) fucosyltransferase gene is the Helicobacter pylori 26695 futA gene, although other α(1,3) fucosyltransferase genes known in the art may be substituted (e.g., α(1,3) fucosyltransferase genes from Helicobacter hepaticus Hh0072, Helicobacter bilis, Campylobacter jejuni, or from Bacteroides species). The invention includes a nucleic acid construct comprising one, two, three or more of the genes described above. For example, the invention includes a nucleic acid construct expressing an exogenous fucosyltransferase gene (encoding α(1,2) fucosyltransferase or α(1,3) fucosyltransferase) transformed into a bacterial host strain comprising a deleted endogenous β-galactosidase (e.g., lacZ) gene, a replacement functional β-galactosidase gene of low activity, a GDP-fucose synthesis pathway, a functional lactose permease gene, and a deleted lactose acetyltransferase gene.

Also within the invention is an isolated E. coli bacterium as described above and characterized as comprising a defective colanic acid synthesis pathway, a reduced level of β-galactosidase (LacZ) activity, and an exogenous fucosyl transferase gene. The invention also includes: a) methods for phenotypic marking of a gene locus in a β-galactosidase negative host cell by utilizing a β-galactosidase (e.g., lacZ) gene insert engineered to produce a low but readily detectable level of β-galactosidase activity, b) methods for readily detecting lytic bacteriophage contamination in fermentation runs through release and detection of cytoplasmic β-galactosidase in the cell culture medium, and c) methods for depleting a bacterial culture of residual lactose at the end of production runs. a), b) and c) are each achieved by utilizing a functional β-galactosidase (e.g., lacZ) gene insert carefully engineered to direct the expression of a low, but detectable level of β-galactosidase activity in an otherwise β-galactosidase negative host cell.

A purified fucosylated oligosaccharide produced by the methods described above is also within the invention. A purified oligosaccharide, e.g., 2'-FL, 3FL, LDFT, is one that is at least 90%, 95%, 98%, 99%, or 100% (w/w) of the desired oligosaccharide by weight.

Purity is assessed by any known method, e.g., thin layer chromatography or other electrophoretic or chromatographic techniques known in the art. The invention includes a method of purifying a fucosylated oligosaccharide produced by the genetically engineered bacterium described above, which method comprises separating the desired fucosylated oligosaccharide (e.g., 2'-FL) from contaminants in a bacterial cell extract or lysate, or bacterial cell culture supernatant. Contaminants include bacterial DNA, protein and cell wall components, and yellow/brown sugar caramels sometimes formed in spontaneous chemical reactions in the culture medium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprising purified 2'-fucosyllactose (2'-FL), 3-fucosyllactose (3FL), lactodifucotetraose (LDFT), or 3'-sialyl-3-fucosyllactose (3'-S3FL) and an excipient is suitable for oral administration. Large quantities of 2'-FL, 3FL, LDFT, or 3'-S3FL are produced in bacterial hosts, e.g., an E. coli bacterium comprising a heterologous α(1,2)fucosyltransferase, a heterologous α(1,3) fucosyltransferase, or a heterologous sialyltransferase, or a combination thereof. An E. coli bacterium comprising an enhanced cytoplasmic pool of each of the following: lactose, GDP-fucose, and CMP-Neu5Ac, is useful in such production systems. In the case of lactose and GDP-fucose, endogenous E. coli metabolic pathways and genes are manipulated in ways that result in the generation of increased cytoplasmic concentrations of lactose and/or GDP-fucose, as compared to levels found in wild type E. coli. For example, the bacteria contain at least 10%, 20%, 50%, 2×, 5×, 10× or more of the levels in a corresponding wild type bacteria that lacks the genetic modifications described above. In the case of CMP-Neu5Ac, endogenous Neu5Ac catabolism genes are inactivated and exogenous CMP-Neu5Ac biosynthesis genes introduced into E. coli resulting in the generation of a cytoplasmic pool of CMP-Neu5Ac not found in the wild type bacterium. A method of producing a pharmaceutical composition comprising a purified HMOS is carried out by culturing the bacterium described above, purifying the HMOS produced by the bacterium, and combining the HMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease.

The invention therefore provides methods for increasing intracellular levels of GDP-fucose in *Escherichia coli* by manipulating the organism's endogenous colanic acid biosynthesis pathway. This is achieved through a number of genetic modifications of endogenous *E. coli* genes involved either directly in colanic acid precursor biosynthesis, or in overall control of the colanic acid synthetic regulon. The invention also provides for increasing the intracellular concentration of lactose in *E. coli*, for cells grown in the presence of lactose, by using manipulations of endogenous *E. coli* genes involved in lactose import, export, and catabolism. In particular, described herein are methods of increasing intracellular lactose levels in *E. coli* genetically engineered to produce a human milk oligosaccharide by incorporating a lacA mutation into the genetically modified *E. coli*. The lacA mutation prevents the formation of intracellular acetyl-lactose, which not only removes this molecule as a contaminant from subsequent purifications, but also eliminates *E. coli*'s ability to export excess lactose from its cytoplasm, thus greatly facilitating purposeful manipulations of the *E. coli* intracellular lactose pool.

Also described herein are bacterial host cells with the ability to accumulate a intracellular lactose pool while simultaneously possessing low, functional levels of cytoplasmic β-galactosidase activity, for example as provided by the introduction of a functional recombinant *E. coli* lacZ gene, or by a β-galactosidase gene from any of a number of other organisms (e.g., the lac4 gene of *Kluyveromyces lactis* (e.g., GenBank Accession Number M84410 (GI: 173304), incorporated herein by reference). Low, functional levels of cytoplasmic β-galactosidase include β-galactosidase activity levels of between 0.05 and 200 units, e.g., between 0.05 and 5 units, between 0.05 and 4 units, between 0.05 and 3 units, or between 0.05 and 2 units (for unit definition see: Miller J H, Laboratory CSH. Experiments in molecular genetics. Cold Spring Harbor Laboratory Cold Spring Harbor, N.Y.; 1972; incorporated herein by reference). This low level of cytoplasmic β-galactosidase activity, while not high enough to significantly diminish the intracellular lactose pool, is nevertheless very useful for tasks such as phenotypic marking of desirable genetic loci during construction of host cell backgrounds, for detection of cell lysis due to undesired bacteriophage contaminations in fermentation processes, or for the facile removal of undesired residual lactose at the end of fermentations.

In one aspect, the human milk oligosaccharide produced by engineered bacteria comprising an exogenous nucleic acid molecule encoding an α(1,2) fucosyltransferase, is 2'-FL (2'-fucosyllactose). Preferably, the α(1,2)fucosyltransferase utilized is the previously completely uncharacterized wcfW gene from *Bacteroides fragilis* NCTC 9343 of the present invention, alternatively the futC gene of *Helicobacter pylori* 26695 or the wbsJ gene of *E. coli* strain O128:B12, or any other α(1,2) fucosyltransferase capable of using lactose as the sugar acceptor substrate may be utilized for 2'-FL synthesis. In another aspect the human milk oligosaccharide produced by engineered bacteria comprising an exogenous nucleic acid molecule encoding an α(1,3) fucosyltransferase, is 3FL (3-fucosyllactose), wherein the bacterial cell comprises an exogenous nucleic acid molecule encoding an exogenous α(1,3) fucosyltransferase. Preferably, the bacterial cell is *E. coli*. The exogenous α(1,3) fucosyltransferase is isolated from, e.g., *Helicobacter pylori, H. hepaticus, H. bilis, C. jejuni*, or a species of *Bacteroides*. In one aspect, the exogenous α(1,3) fucosyltransferase comprises *H. hepaticus* Hh0072, *H. pylori* 11639 FucTa, or *H. pylori* UA948 FucTa (e.g., GenBank Accession Number AF194963 (GI:28436396), incorporated herein by reference). The invention also provides compositions comprising *E. coli* genetically engineered to produce the human milk tetrasaccharide lactodifucotetraose (LDFT). The *E. coli* in this instance comprise an exogenous nucleic acid molecule encoding an α(1,2) fucosyltransferase and an exogenous nucleic acid molecule encoding an α(1,3) fucosyltransferase. In one aspect, the *E. coli* is transformed with a plasmid expressing an α(1,2) fucosyltransferase and/or a plasmid expressing an α(1,3) fucosyltransferase. In another aspect, the *E. coli* is transformed with a plasmid that expresses both an α(1,2) fucosyltransferase and an α(1,3) fucosyltransferase. Alternatively, the *E. coli* is transformed with a chromosomal integrant expressing an α(1,2) fucosyltransferase and a chromosomal integrant expressing an α(1,3) fucosyltransferase. Optionally, the *E. coli* is transformed with plasmid pG177.

Also described herein are compositions comprising a bacterial cell that produces the human milk oligosaccharide 3'-S3FL (3'-sialyl-3-fucosyllactose), wherein the bacterial cell comprises an exogenous sialyl-transferase gene encoding α(2,3)sialyl-transferase and an exogenous fucosyltransferase gene encoding α(1,3) fucosyltransferase. Preferably, the bacterial cell is *E. coli*. The exogenous fucosyltransferase gene is isolated from, e.g., *Helicobacter pylori, H. hepaticus, H. bilis, C. jejuni*, or a species of *Bacteroides*. For example, the exogenous fucosyltransferase gene comprises *H. hepaticus* Hh0072, *H. pylori* 11639 FucTa, or *H. pylori* UA948 FucTa. The exogenous sialyltransferase gene utilized for 3'-S3FL production may be obtained from any one of a number of sources, e.g., those described from *N. meningitidis* and *N. gonorrhoeae*. Preferably, the bacterium comprises a GDP-fucose synthesis pathway.

Additionally, the bacterium contains a deficient sialic acid catabolic pathway. By "sialic acid catabolic pathway" is meant a sequence of reactions, usually controlled and catalyzed by enzymes, which results in the degradation of sialic acid. An exemplary sialic acid catabolic pathway in *Escherichia coli* is described herein. In the sialic acid catabolic pathway described herein, sialic acid (Neu5Ac; N-acetylneuraminic acid) is degraded by the enzymes NanA (N-acetylneuraminic acid lyase) and NanK (N-acetylmannosamine kinase). For example, a deficient sialic acid catabolic pathway is engineered in *Escherichia coli* by way of a null mutation in endogenous nanA (N-acetylneuraminate lyase) (e.g., GenBank Accession Number D00067 (GI: 216588), incorporated herein by reference) and/or nanK (N-acetylmannosamine kinase) genes (e.g., GenBank Accession Number (amino acid) BAE77265 (GI:85676015), incorporated herein by reference). Other components of sialic acid metabolism include: (nanT) sialic acid transporter; (ManNAc-6-P) N-acetylmannosamine -6-phosphate; (GlcNAc-6-P) N-acetylglucosamine-6-phosphate; (GlcN-6-P) Glucosamine-6-phosphate; and (Fruc-6-P) Fructose-6-phosphate.

Moreover, the bacterium (e.g., *E. coli*) also comprises a sialic acid synthetic capability. For example, the bacterium comprises a sialic acid synthetic capability through provision of an exogenous UDP-GlcNAc 2-epimerase (e.g., neuC of *Campylobacter jejuni* or equivalent (e.g., GenBank Accession Number (amino acid) AAG29921 (GI: 11095585), incorporated herein by reference)), a Neu5Ac synthase (e.g., neuB of *C. jejuni* or equivalent, e.g., GenBank Accession Number (amino acid) AAG29920 (GI: 11095584), incorporated herein by reference)), and/or a CMP-Neu5Ac synthetase (e.g., neuA of *C. jejuni* or equivalent, e.g., GenBank Accession Number (amino acid) ADN91474 (GI:307748204), incorporated herein by reference).

Additionally, the bacterium also comprises a functional β-galactosidase gene and a functional lactose permease gene. Bacteria comprising the characteristics described herein are cultured in the presence of lactose, and a 3'-sialyl-3-fucosyllactose is retrieved, either from the bacterium itself or from a culture supernatant of the bacterium.

Also provided are methods for producing a 3'-sialyl-3-fucosyllactose (3'-S3FL) in an enteric bacterium, wherein the enteric bacterium comprises a mutation in an endogenous colanic acid synthesis gene, a functional lacZ gene, a functional lactose permease gene, an exogenous fucosyltransferase gene encoding α(1,3) fucosyltransferase, and an exogenous sialyltransferase gene encoding an α(2,3)sialyl transferase. Additionally, the bacterium contains a deficient sialic acid catabolic pathway. For example, the bacterium comprises a deficient sialic acid catabolic pathway by way of a null mutation in endogenous nanA (N-acetylneuraminate lyase) and/or nanK (N-acetylmannosamine kinase) genes. The bacterium also comprises a sialic acid synthetic capability. For example, the bacterium comprises a sialic acid synthetic capability through provision of an exogenous UDP-GlcNAc 2-epimerase (e.g., neuC of *C. jejuni* or equivalent), a Neu5Ac synthase (e.g., neuB of *C. jejuni* or equivalent), and/or a CMP-Neu5Ac synthetase (e.g., neuA of *C. jejuni* or equivalent). Bacteria comprising the characteristics described herein are cultured in the presence of lactose, and a 3'-sialyl-3-fucosyllactose is retrieved, either from the bacterium itself or from a culture supernatant of the bacterium.

Also provided is a method for phenotypic marking of a gene locus in a host cell, whose native β-galactosidase gene is deleted or inactivated, by utilizing an inserted recombinant β-galactosidase (e.g., lacZ) gene engineered to produce a low, but detectable level of β-galactosidase activity. Similarly, the invention also provides methods for depleting a bacterial culture of residual lactose in a β-galactosidase negative host cell, whose native β-galactosidase gene is deleted or inactivated, by utilizing an inserted recombinant β-galactosidase (e.g., lacZ) gene engineered to produce a low but detectable level of β-galactosidase activity. Finally, also provided is a method for detecting bacterial cell lysis in a culture of a β-galactosidase negative host cell, whose native β-galactosidase gene is deleted or inactivated, by utilizing an inserted recombinant β-galactosidase (e.g., lacZ) gene engineered to produce a low but detectable level of β-galactosidase activity.

Methods of purifying a fucosylated oligosaccharide produced by the methods described herein are carried out by binding the fucosylated oligosaccharide from a bacterial cell lysate or bacterial cell culture supernatant of the bacterium to a carbon column, and eluting the fucosylated oligosaccharide from the column. Purified fucosylated oligosaccharide are produced by the methods described herein.

Optionally, the invention features a vector, e.g., a vector containing a nucleic acid. The vector can further include one or more regulatory elements, e.g., a heterologous promoter. The regulatory elements can be operably linked to a protein gene, fusion protein gene, or a series of genes linked in an operon in order to express the fusion protein. In yet another aspect, the invention comprises an isolated recombinant cell, e.g., a bacterial cell containing an aforementioned nucleic acid molecule or vector. The nucleic acid sequence can be optionally integrated into the genome.

The term "substantially pure" in reference to a given polypeptide, polynucleotide or oligosaccharide means that the polypeptide, polynucleotide or oligosaccharide is substantially free from other biological macromolecules. The substantially pure polypeptide, polynucleotide or oligosaccharide is at least 75% (e.g., at least 80, 85, 95, or 99%) pure by dry weight. Purity can be measured by any appropriate calibrated standard method, for example, by column chromatography, polyacrylamide gel electrophoresis, thin layer chromatography (TLC) or HPLC analysis.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, Purified HMOS compositions are at least 60% by weight (dry weight) the compound of interest. Preferably, the preparation is at least 75%, more preferably at least 90%, and most preferably at least 99%, by weight the compound of interest. Purity is measured by any appropriate calibrated standard method, for example, by column chromatography, polyacrylamide gel electrophoresis, thin layer chromatography (TLC) or HPLC analysis. For example, a "purified protein" refers to a protein that has been separated from other proteins, lipids, and nucleic acids with which it is naturally associated. Preferably, the protein constitutes at least 10, 20, 50 70, 80, 90, 95, 99-100% by dry weight of the purified preparation.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide.

A "heterologous promoter", when operably linked to a nucleic acid sequence, refers to a promoter which is not naturally associated with the nucleic acid sequence.

The terms "express" and "over-express" are used to denote the fact that, in some cases, a cell useful in the method herein may inherently express some of the factor that it is to be genetically altered to produce, in which case the addition of the polynucleotide sequence results in overexpression of the factor. That is, more factor is expressed by the altered cell than would be, under the same conditions, by a wild type cell. Similarly, if the cell does not inherently express the factor that it is genetically altered to produce, the term used would be to merely "express" the factor since the wild type cell did not express the factor at all.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

The invention provides a method of treating, preventing, or reducing the risk of infection in a subject comprising administering to said subject a composition comprising a human milk oligosaccharide, purified from a culture of a recombinant strain of the current invention, wherein the HMOS binds to a pathogen and wherein the subject is infected with or at risk of infection with the pathogen. In one aspect, the infection is caused by a Norwalk-like virus or *Campylobacter jejuni*. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified HMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations intended to enhance the growth of beneficial microorganisms either in vitro or in vivo. For example, the purified sugar (e.g., 2'-FL) can be mixed with a *Bifidobacterium* or *Lactobacillus* in a probiotic nutritional composition. (i.e. *Bifidobacteria* are beneficial components of a normal human gut flora and are also known to utilize HMOS for growth.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 13A-E is a DNA sequence with annotations (in GenBank format) of the DNA insertion into the ion region diagrammed in FIG. 12 (SEQ ID NOs 9-15).

FIG. 14 is a table containing the genotypes of several *E. coli* strains of the current invention.

DETAILED DESCRIPTION OF THE INVENTION

Figure 1:
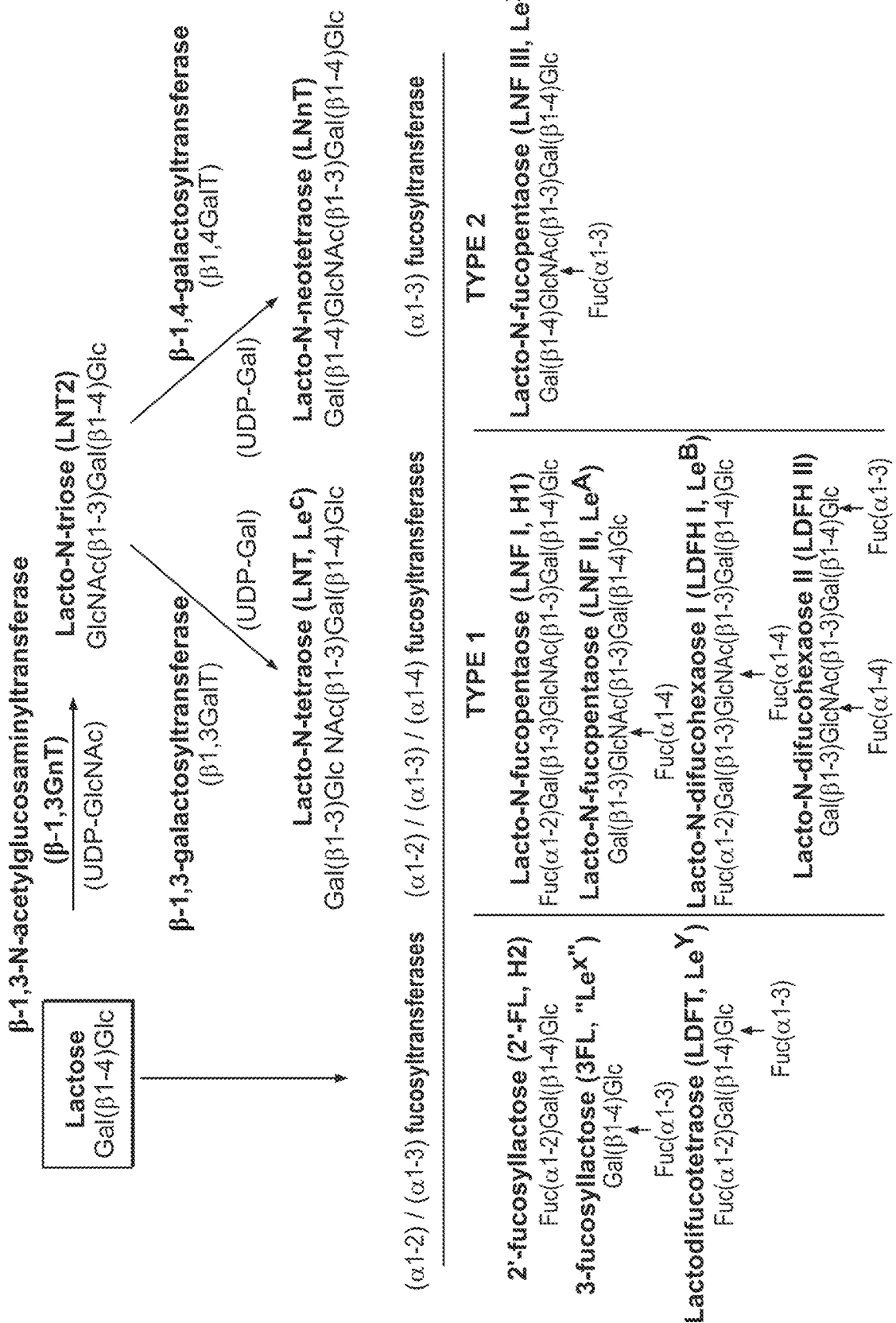
FIG. 1 is a schematic illustration showing the synthetic pathway of the major neutral fucosyl-oligosaccharides found in human milk.
Figure 2:
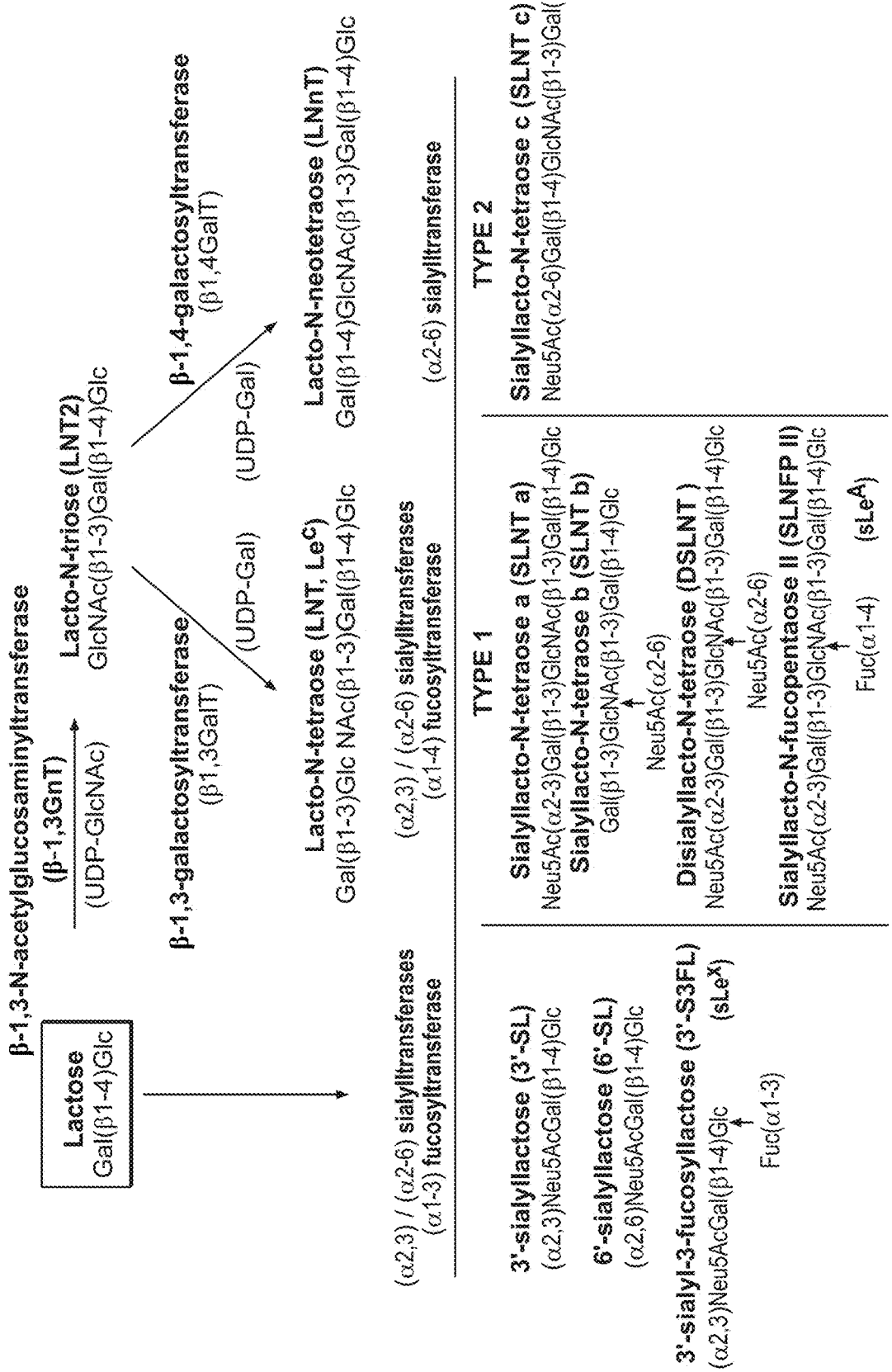
FIG. 2 is a schematic illustration showing the synthetic pathway of the major sialyloligosaccharides found in human milk.

Human milk glycans, which comprise both oligosaccharides (HMOS) and their glycoconjugates, play significant roles in the protection and development of human infants, and in particular the infant gastrointestinal (GI) tract. Milk oligosaccharides found in various mammals differ greatly, and their composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Previously, a full exploration of the roles of HMOS was limited by the inability to adequately characterize and measure these compounds. In recent years sensitive and reproducible quantitative methods for the analysis of both neutral and acidic HMOS have been developed (Erney, R., Hilty, M., Pickering, L., Ruiz-Palacios, G., and Prieto, P. (2001) *Adv Exp Med Biol* 501, 285-297. Bao, Y., and Newburg, D. S. (2008) Electrophoresis 29, 2508-2515). Approximately 200 distinct oligosaccharides have been identified in human milk, and combinations of a small number of simple epitopes are responsible for this diversity (Newburg D. S., 1999 Curr Med Chem, 6:117-127; Ninonuevo M. et al., 2006 J Agric Food Chem, 54:7471-74801). HMOS are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). HMOS are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal Biochem, 273:261-277; Martifn-Sosa et al., 2003 J Dairy Sci, 86:52-59; Parkkinen J. and Finne J., 1987 Methods Enzymol, 138:289-300; Shen Z. et al., 2001 J Chromatogr A, 921:315-321). Approximately 70-80% of oligosaccharides in human milk are fucosylated, and their synthetic pathways are believed to proceed in a manner similar to those pathways shown in FIG. 1 (with the Type I and Type II subgroups beginning with different precursor molecules). A smaller proportion of the oligosaccharides in human milk are sialylated, or are both fucosylated and sialylated. FIG. 2 outlines possible biosynthetic routes for sialylated (acidic) HMOS, although their actual synthetic pathways in humans are not yet completely defined.

Interestingly, HMOS as a class, survive transit through the intestine of infants very efficiently, a function of their being poorly transported across the gut wall and of their resistance to digestion by human gut enzymes (Chaturvedi, P., Warren, C. D., Buescher, C. R., Pickering, L. K. & Newburg, D. S. *Adv Exp Med Biol* 501, 315-323 (2001)). One consequence of this survival in the gut is that HMOS are able to function as prebiotics, i.e. they are available to serve as an abundant carbon source for the growth of resident gut commensal microorganisms (Ward, R. E., Nifionuevo, M., Mills, D. A., Lebrilla, C. B., and German, J. B. (2007) *Mol Nutr Food Res* 51, 1398-1405). Recently, there is burgeoning interest in the role of diet and dietary prebiotic agents in determining the composition of the gut microflora, and in understanding the linkage between the gut microflora and human health (Roberfroid, M., Gibson, G. R., Hoyles, L, McCartney, A. L., Rastall, R., Rowland, I., Wolvers, D., Watzl, B., Szajewska, H., Stahl, B., Guarner, F., Respondek, F., Whelan, K., Coxam, V., Davicco, M. J., Léotoing, L., Wittrant, Y., Delzenne, N. M., Cani, P. D., Neyrinck, A. M., and Meheust, A. (2010) *Br J Nutr* 104 Suppl 2, S1-63).

A number of human milk glycans possess structural homology to cell receptors for enteropathogens, and serve roles in pathogen defense by acting as molecular receptor "decoys". For example, pathogenic strains of *Campylobacter* bind specifically to glycans in human milk containing the H-2 epitope, i.e., 2'-fucosyl-N-acetyllactosamine or 2'-fucosyllactose (2'-FL); *Campylobacter* binding and infectivity are inhibited by 2'-FL and other glycans containing this H-2 epitope (Ruiz-Palacios, G. M., Cervantes, L. E., Ramos, P., Chavez-Munguia, B., and Newburg, D. S. (2003) *J Biol Chem* 278, 14112-14120). Similarly, some diarrheagenic *E. coli* pathogens are strongly inhibited in vivo by HMOS containing 2'-linked fucose moieties. Several major strains of human caliciviruses, especially the noroviruses, also bind to 2'-linked fucosylated glycans, and this binding is inhibited by human milk 2'-linked fucosylated glycans. Consumption of human milk that has high levels of these 2'-linked fucosyloligosaccharides has been associated with lower risk of norovirus, *Campylobacter*, ST of *E. coli*-associated diarrhea, and moderate-to-severe diarrhea of all causes in a Mexican cohort of breastfeeding children (Newburg D. S. et al., 2004 Glycobiology, 14:253-263; Newburg D. S. et al., 1998 Lancet, 351:1160-1164). Several pathogens are also known to utilize sialylated glycans as their host receptors, such as influenza (Couceiro, J. N., Paulson, J. C. & Baum, L G. Virus Res 29, 155-165 (1993)), parainfluenza (Amonsen, M., Smith, D. F., Cummings, R. D. & Air, G. M. J Virol 81, 8341-8345 (2007)), and rotoviruses (Kuhlenschmidt, T. B., Hanafin, W. P., Gelberg, H. B. & Kuhlenschmidt, M. S. Adv Exp Med Biol 473, 309-317

(1999)). The sialyl-Lewis X epitope is used by *Helicobacter pylori* (Mahdavi, J., Sondén, B., Hurtig, M., Olfat, F. O., et al. Science 297, 573-578 (2002)), *Pseudomonas aeruginosa* (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoën-Clouet, N., et al. Glycobiology 19, 309-320 (2009)).

While studies suggest that human milk glycans could be used as prebiotics and as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Novel chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)). Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)). However, low overall product yields and high process complexity have limited the commercial utility of these approaches.

Prior to the invention described herein, which enables the inexpensive production of large quantities of neutral and acidic HMOS, it had not been possible to fully investigate the ability of this class of molecule to inhibit pathogen binding, or indeed to explore their full range of potential additional functions.

Prior to the invention described herein, chemical syntheses of HMOS were possible, but were limited by stereospecificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). Also, prior to the invention described herein, in vitro enzymatic syntheses were also possible, but were limited by a requirement for expensive nucleotide-sugar precursors. The invention overcomes the shortcomings of these previous attempts by providing new strategies to inexpensively manufacture large quantities of human milk oligosaccharides for use as dietary supplements. The invention described herein makes use of an engineered bacterium *E. coli* (or other bacteria) engineered to produce 2'-FL, 3FL, LDFT, or sialylated fucosyl-oligosaccharides in commercially viable levels, for example the methods described herein enable the production of 2'-fucosylactose at >50 g/L in bioreactors.

Example 1. Engineering of *E. coli* to Generate Host Strains for the Production of Fucosylated Human Milk Oligosaccharides The *E. coli* K12 prototroph W3110 was chosen as the parent background for fucosylated HMOS biosynthesis. This strain had previously been modified at the ampC locus by the introduction of a tryptophan-inducible $P_{trpB}$-cI+ repressor construct (McCoy, J. & Lavallie, E. Current protocols in molecular biology/edited by Frederick M. Ausubel . . . [et al.](2001)), enabling economical production of recombinant proteins from the phage $\lambda P_L$ promoter (Sanger, F., Coulson, A. R., Hong, G. F., Hill, D. F. & Petersen, G. B. J Mol Biol 162, 729-773 (1982)) through induction with millimolar concentrations of tryptophan (Mieschendahl, M., Petri, T. & Hänggi, U. Nature Biotechnology 4, 802-808 (1986)). The strain GI724, an *E. coli* W3110 derivative containing the tryptophan-inducible $P_{trpB}$-cI+ repressor construct in ampC, was used at the basis for further *E. coli* strain manipulations (FIG. 14).

Figure 3:
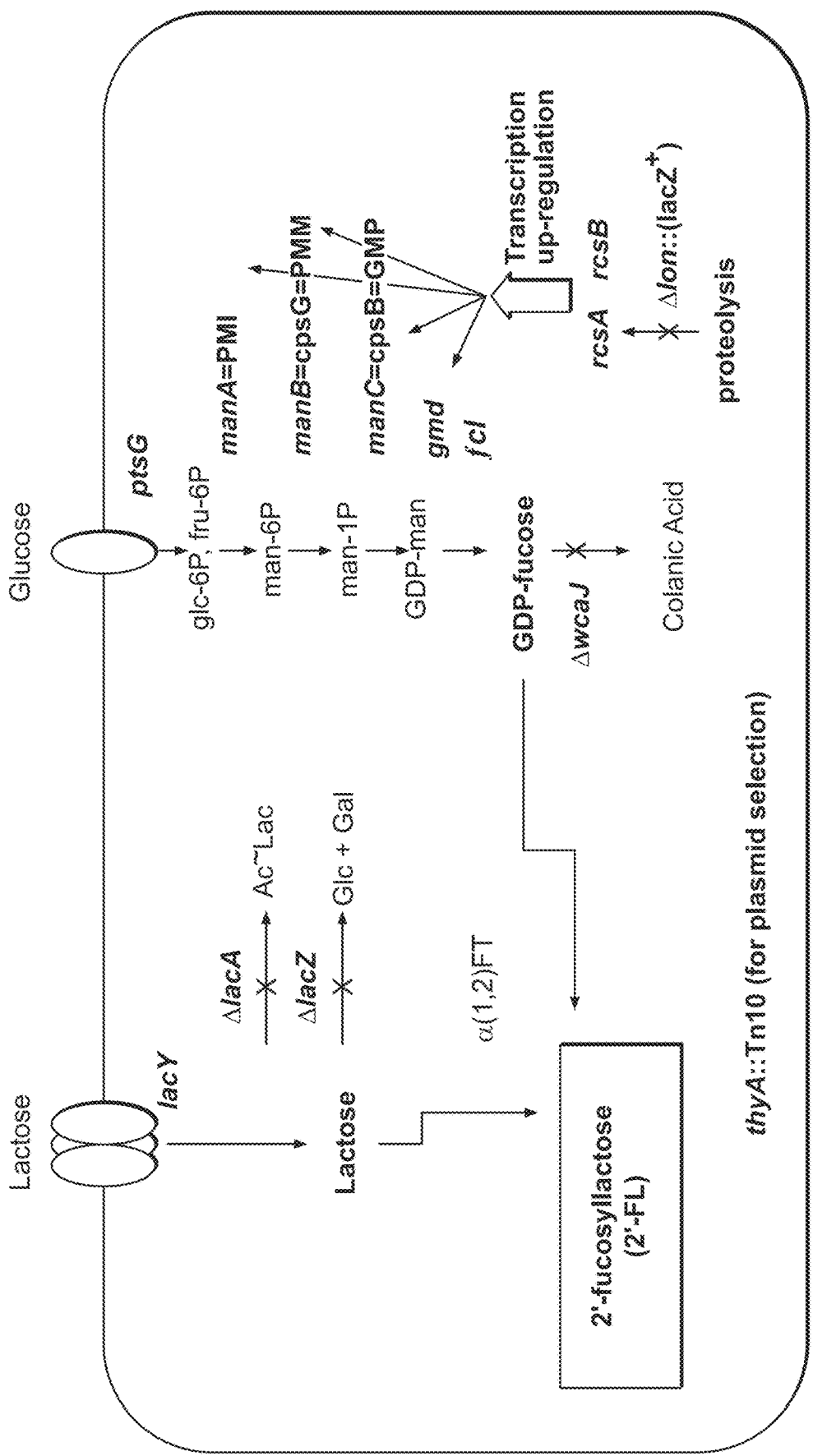
FIG. 3 is a schematic demonstrating metabolic pathways and the changes introduced into them to engineer 2'-fucosyllactose (2'-FL) synthesis in *Escherichia coli* (*E. coli*). Specifically, the lactose synthesis pathway and the GDP-fucose synthesis pathway are illustrated. In the GDP-fucose synthesis pathway: manA=phosphomannose isomerase (PMI), manB=phosphomannomutase (PMM), manC=mannose-1-phosphate guanylyltransferase (GMP), gmd=GDP-mannose-4,6-dehydratase, fcl=GDP-fucose synthase (GFS), and ΔwcaJ=mutated UDP-glucose lipid carrier transferase.
Figure 4:
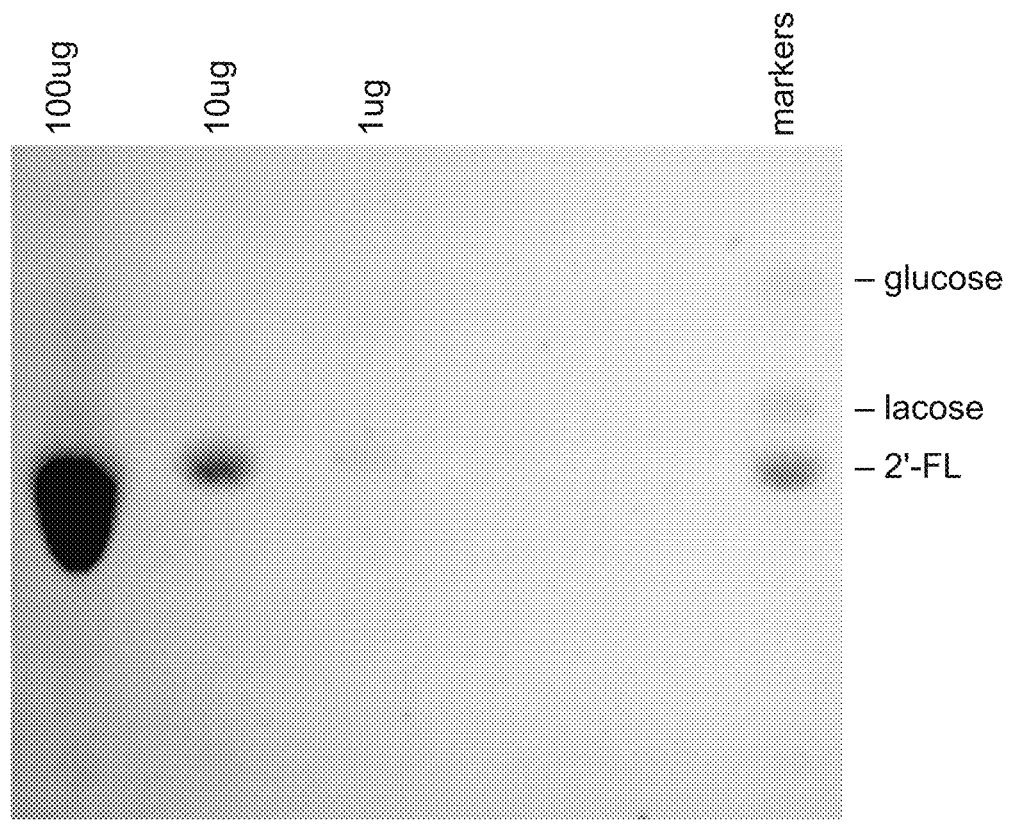
FIG. 4 is a photograph of a thin layer chromatogram of purified 2'-FL produced in *E. coli*.

Biosynthesis of fucosylated HMOS requires the generation of an enhanced cellular pool of both lactose and GDP-fucose (FIG. 3). This enhancement was achieved in strain GI724 through several manipulations of the chromosome using) Red recombineering (Court, D. L, Sawitzke, J. A. & Thomason, L. C. Annu Rev Genet 36, 361-388 (2002)) and generalized P1 phage transduction (Thomason, L. C., Costantino, N. & Court, D. L. Mol Biol Chapter 1, Unit 1.17 (2007)). FIG. 14 is a table presenting the genotypes of several *E. coli* strains constructed for this invention. The ability of the *E. coli* host strain to accumulate intracellular lactose was first engineered in strain E183 (FIG. 14) by simultaneous deletion of the endogenous β-galactosidase gene (lacZ) and the lactose operon repressor gene (lacI). During construction of this deletion in GI724 to produce E183, the lacIq promoter was placed immediately upstream of the lactose permease gene, lacY. The modified strain thus maintains its ability to transport lactose from the culture medium (via LacY), but is deleted for the wild-type copy of the lacZ (β-galactosidase) gene responsible for lactose catabolism. An intracellular lactose pool is therefore created when the modified strain is cultured in the presence of exogenous lactose.

Subsequently, the ability of the host *E. coli* strain to synthesize colanic acid, an extracellular capsular polysaccharide, was eliminated in strain E205 (FIG. 14) by the deletion of the wcaJ gene, encoding the UDP-glucose lipid carrier transferase (Stevenson, G., Andrianopoulos, K., Hobbs, M. & Reeves, P. R. J Bacteriol 178, 4885-4893 (1996)) in strain E183. In a wcaJ null background, GDP-fucose accumulates in the *E. coli* cytoplasm (Dumon, C., Priem, B., Martin, S. L., Heyraud, A., et al. Glycoconj J 18, 465-474 (2001)).

A thyA (thymidylate synthase) mutation was introduced into strain E205 to produce strain E214 (FIG. 14) by P1 transduction. In the absence of exogenous thymidine, thyA strains are unable to make DNA, and die. The defect can be complemented in trans by supplying a wild-type thyA gene on a multicopy plasmid (Belfort, M., Maley, G. F. & Maley, F. Proceedings of the National Academy of Sciences 80, 1858 (1983)). This complementation is used herein as a means of plasmid maintenance (eliminating the need for a more conventional antibiotic selection scheme to maintain plasmid copy number).

One strategy for GDP-fucose production is to enhance the bacterial cell's natural synthesis capacity. For example, this is enhancement is accomplished by inactivating enzymes involved in GDP-fucose consumption, and/or by overexpressing a positive regulator protein, RcsA, in the colanic acid (a fucose-containing exopolysaccharide) synthesis pathway. Collectively, this metabolic engineering strategy re-directs the flux of GDP-fucose destined for colanic acid synthesis to oligosaccharide synthesis (FIG. 3). By "GDP-fucose synthesis pathway" is meant a sequence of reactions, usually controlled and catalyzed by enzymes, which results in the synthesis of GDP-fucose. An exemplary GDP-fucose synthesis pathway in *Escherichia coli* as described in FIG. 3 is set forth below. In the GDP-fucose synthesis pathway set forth below, the enzymes for GDP-fucose synthesis include: 1) manA=phosphomannose isomerase (PMI), 2) manB=phosphomannomutase (PMM), 3) manC=mannose-1-phosphate guanylyltransferase (GMP), 4) gmd=GDP-mannose-4,6-dehydratase (GMD), 5) fcl=GDP-fucose synthase (GFS), and 6) ΔwcaJ=mutated UDP-glucose lipid carrier transferase.

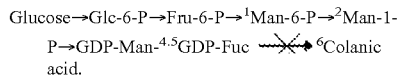

Glucose→Glc-6-P→Fru-6-P→¹Man-6-P→²Man-1-P→GDP-Man-⁴,⁵GDP-Fuc ⟶⟶⁶Colanic acid.

Figure 7:
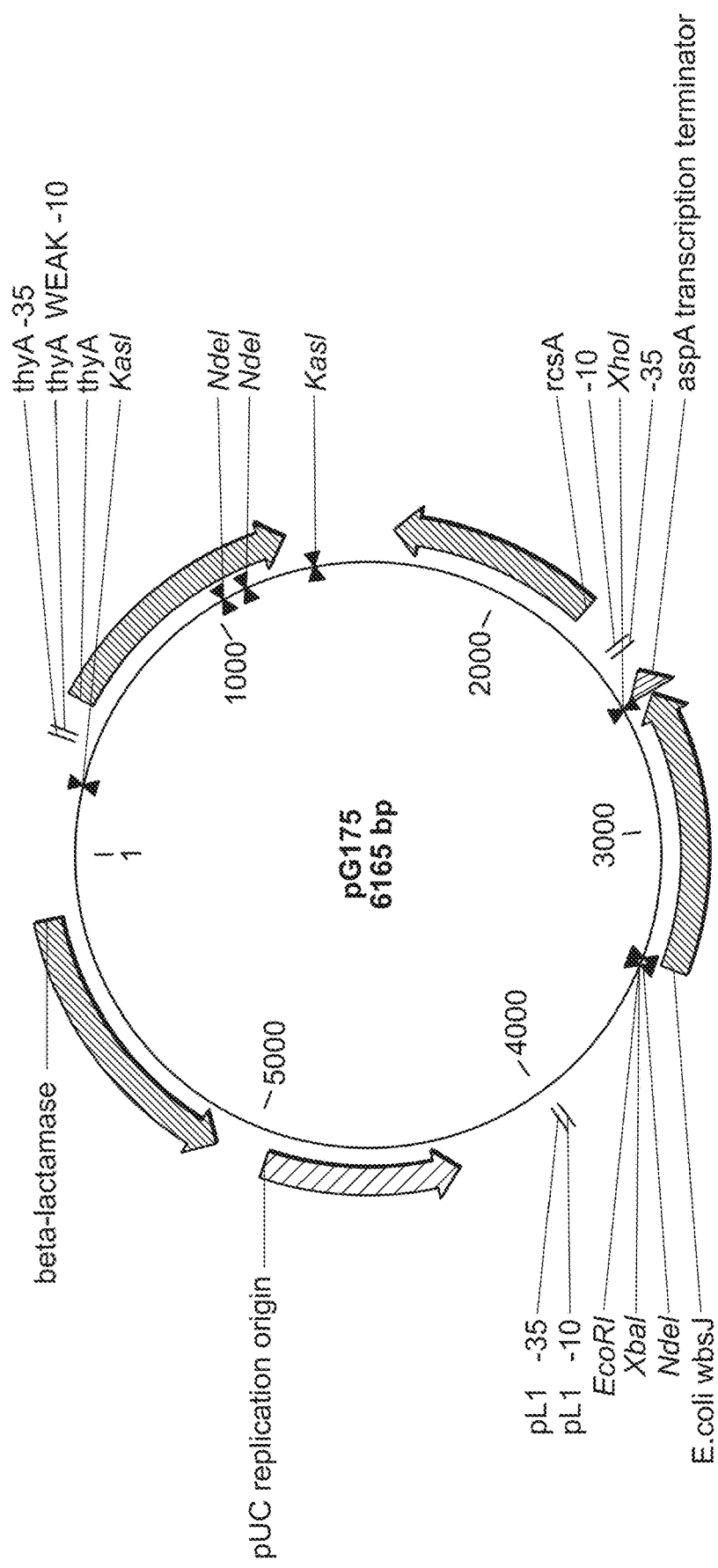
FIG. 7 is a plasmid map of pG175, which expresses the *E. coli* α(1,2)fucosyltransferase gene wbsJ.
Figure 10:
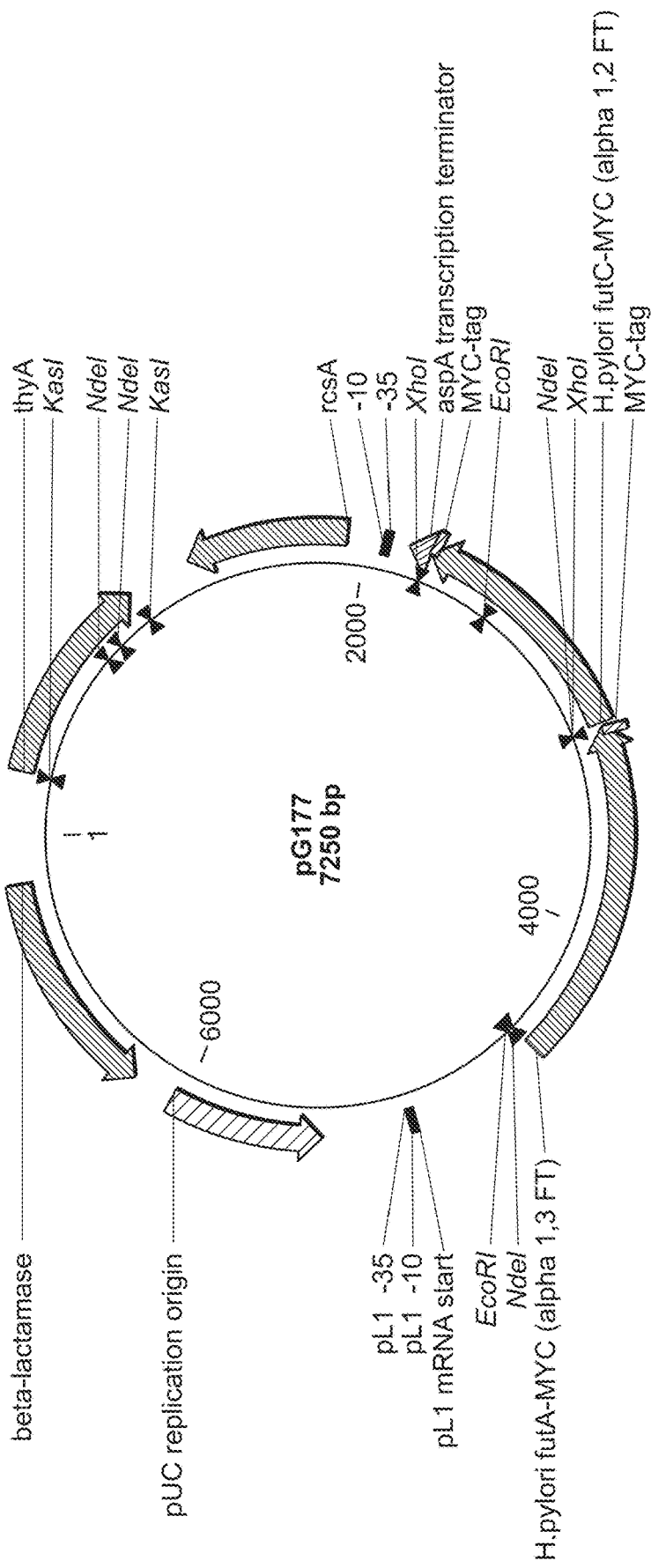
FIG. 10 is a plasmid map of pG177, which contains both the *H. pylori* 26695 α(1,2)fucosyltransferase gene futC and the *H. pylori* 26695 α(1,3)fucosyltransferase gene futA, configured as an operon.
Figure 15:
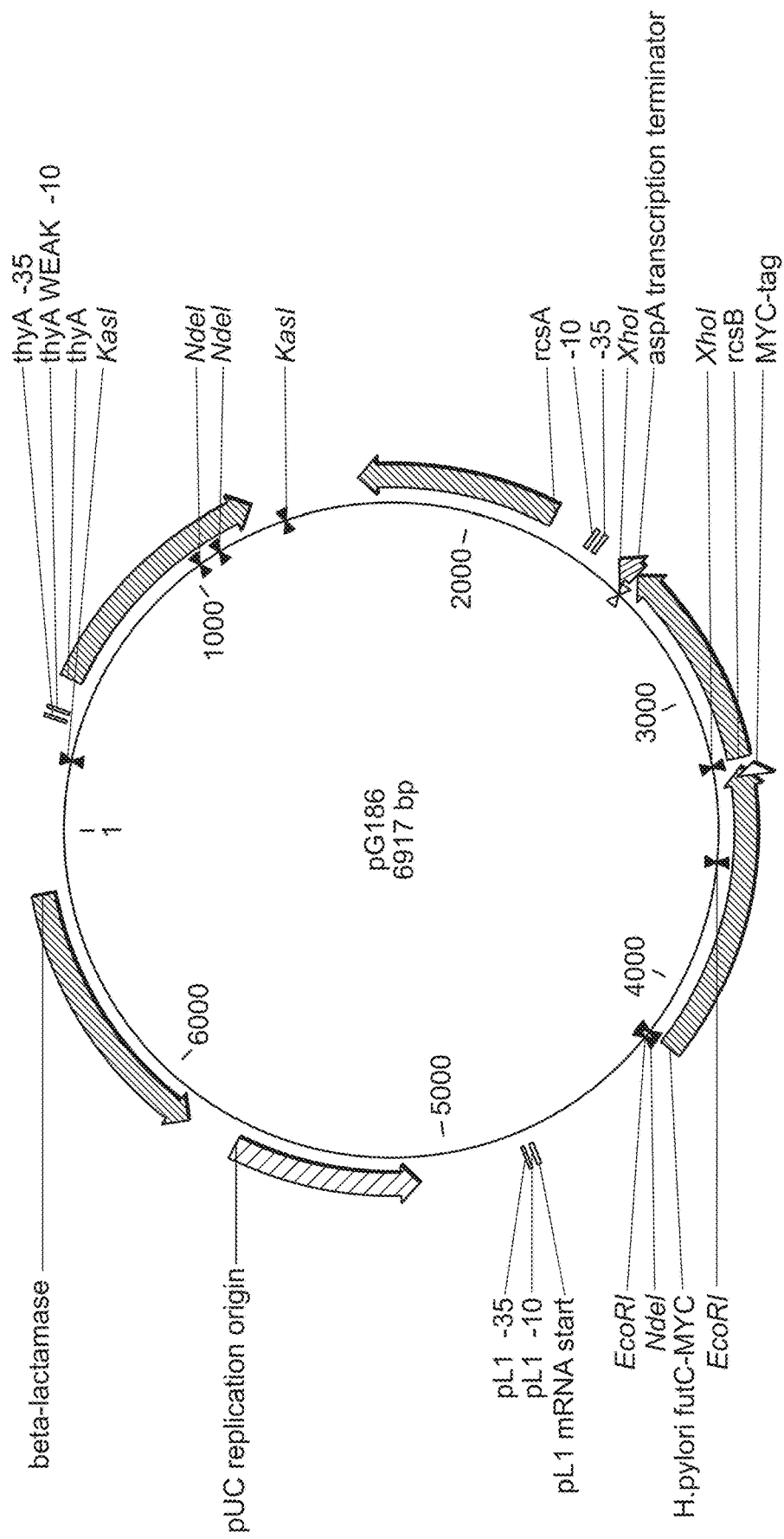
FIG. 15 is a plasmid map of pG186, which expresses the α(1,2)fucosyltransferase gene futC in an operon with the colanic acid pathway transcription activator gene rcsB.

Specifically, the magnitude of the cytoplasmic GDP-fucose pool in strain E214 is enhanced by over-expressing the *E. coli* positive transcriptional regulator of colanic acid biosynthesis, RscA (Gottesman, S. & Stout, V. Mol Microbiol 5, 1599-1606 (1991)). This over-expression of RcsA is achieved by incorporating a wild-type rcsA gene, including its promoter region, onto a multicopy plasmid vector and transforming the vector into the *E. coli* host, e.g. into E214. This vector typically also carries additional genes, in particular one or two fucosyltransferase genes under the control of the pL promoter, and thyA and beta-lactamase genes for plasmid selection and maintenance. pG175 (SEQ ID NO: 1 and FIG. 7), pG176 (SEQ ID NO: 2), pG177 (SEQ ID NO: 3 and FIG. 10), pG171 (SEQ ID NO: 5) and pG180 (SEQ ID NO: 6) are all examples of fucosyltransferase-expressing vectors that each also carry a copy of the rcsA gene, for the purpose of increasing the intracellular GDP-fucose pool of the *E. coli* hosts transformed with these plasmids. Overexpression of an additional positive regulator of colanic acid biosynthesis, namely RcsB (Gupte G, Woodward C, Stout V. Isolation and characterization of rcsb mutations that affect colanic acid capsule synthesis in *Escherichia coli* K-12. J Bacteriol 1997, July; 179(13):4328-35.), can also be utilized, either instead of or in addition to over-expression of RcsA, to increase intracellular GDP-fucose levels. Overexpression of rcsB is also achieved by including the gene on a multi-copy expression vector. pG186 is such a vector (SEQ ID NO: 8 and FIG. 15). pG186 expresses rcsB in an operon with futC under pL promoter control. The plasmid also expresses rcsA, driven off its own promoter. pG186 is a derivative of pG175 in which the α(1,2) FT (wbsJ) sequence is replaced by the *H. pylori* futC gene (FutC is MYC-tagged at its C-terminus). In addition, at the XhoI restriction site immediately 3' of the futC CDS, the *E. coli* rcsB gene is inserted, complete with a ribosome binding site at the 5' end of the rcsB CDS, and such that futC and rcsB form an operon.

Figure 12:
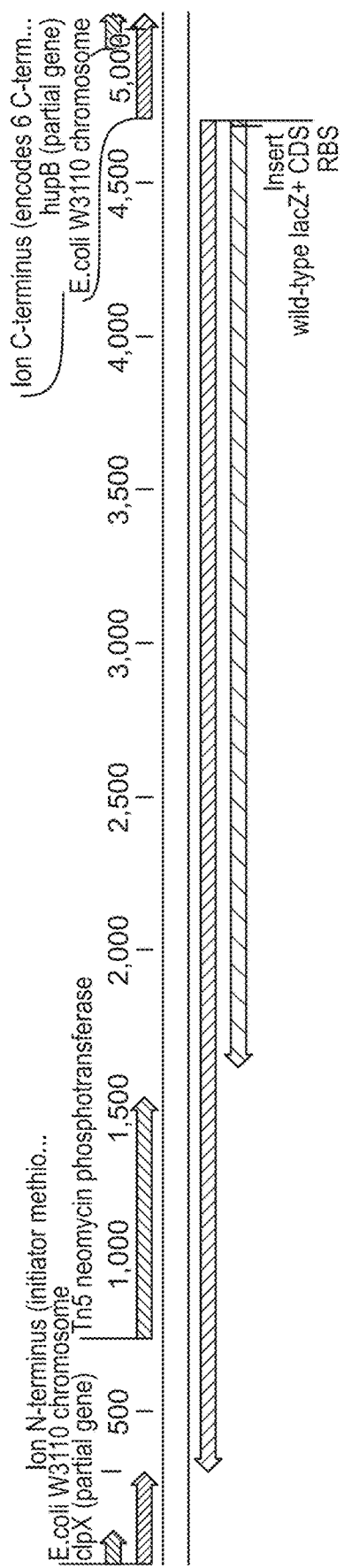
FIG. 12 is a diagram showing the replacement of the ion gene in *E. coli* strain E390 by a DNA fragment carrying both a kanamycin resistance gene (derived from transposon Tn5) and a wild-type *E. coli* lacZ+ coding sequence.

A third means to increase the intracellular GDP-fucose pool may also be employed. Colanic acid biosynthesis is increased following the introduction of a null mutation into the *E. coli* lon gene. Lon is an ATP-dependant intracellular protease that is responsible for degrading RcsA, mentioned above as a positive transcriptional regulator of colanic acid biosynthesis in *E. coli* (Gottesman, S. & Stout, V. Mol Microbiol 5, 1599-1606 (1991)). In a lon null background, RcsA is stabilized, RcsA levels increase, the genes responsible for GDP-fucose synthesis in *E. coli* are up-regulated, and intracellular GDP-fucose concentrations are enhanced. The lon gene was almost entirely deleted and replaced by an inserted functional, wild-type, but promoter-less *E. coli* lacZ⁺ gene (Δlon::(kan, lacZ⁺) in strain E214 to produce strain E390. λRed recombineering was used to perform the construction. FIG. 12 illustrates the new configuration of genes engineered at the lon locus in E390. FIG. 13A-E presents the complete DNA sequence of the region, with annotations in GenBank format. Genomic DNA sequence surrounding the lacZ+ insertion into the lon region in *E. coli* strain E390 is set forth below (SEQ ID NO: 7) The lon mutation in E390 increases intracellular levels of RcsA, and enhances the intracellular GDP-fucose pool. The inserted lacZ⁺ cassette not only knocks out lon, but also converts the lacZ⁻ host back to both a lacZ⁺ genotype and phenotype. The modified strain produces a minimal (albeit still readily detectable) level of β-galactosidase activity (1-2 units), which has very little impact on lactose consumption during production runs, but which is useful in removing residual lactose at the end of runs, is an easily scorable phenotypic marker for moving the lon mutation into other lacZ *E. coli* strains by P1 transduction, and can be used as a convenient test for cell lysis (e.g. caused by unwanted bacteriophage contamination) during production runs in the bioreactor.

The production host strain, E390 incorporates all the above genetic modifications and has the following genotype:

ampC::(P$_{trpB}$λcI⁺),P$_{lacI}$q(ΔlacI-lacZ)$_{158}$lacY⁺,ΔwcaJ, thyA$_{748}$::Tn10,Δlon::(kan,lacZ⁺)

An additional modification of E390 that is useful for increasing the cytoplasmic pool of free lactose (and hence the final yield of 2'-FL) is the incorporation of a lacA mutation. LacA is a lactose acetyltransferase that is only active when high levels of lactose accumulate in the *E. coli* cytoplasm. High intracellular osmolarity (e.g., caused by a high intracellular lactose pool) can inhibit bacterial growth, and *E. coli* has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in *E. coli* engineered to produce 2'-FL or other human milk oligosaccharides is therefore undesirable: it reduces overall yield. Moreover, acetyl-lactose is a side product that complicates oligosaccharide purification schemes. The incorporation of a lacA mutation resolves these problems. Strain E403 (FIG. 14) is a derivative of E390 that carries a deletion of the lacA gene and thus is incapable of synthesizing acetyl-lactose.

The production host strain, E403 incorporates all the above genetic modifications and has the following genotype:

ampC::(P$_{trpB}$λcI⁺),P$_{lacI}$q(ΔlacI-lacZ)$_{158}$lacY⁺,ΔwcaJ, thyA$_{748}$::Tn10,Δlon::(kan,lacZ⁺)ΔlacA Example 2. 2'-FL Production at Small Scale Various alternative α(1,2) fucosyltransferases are able to utilize lactose as a sugar acceptor and are available for the purpose of 2'-FL synthesis when expressed under appropriate culture conditions in *E. coli* E214, E390 or E403. For example the plasmid pG175 (ColE1, thyA+, bla+, P$_{L2}$-wbsJ, rcsA+) (SEQ ID NO: 1, FIG. 7) carries the wbsJ α(1,2) fucosyltransferase gene of *E. coli* strain O128:B12 and can direct the production of 2'-FL in *E. coli* strain E403. In another example plasmid pG171 (ColE1, thyA+, bla+, P$_{L2}$-futC, rcsA+) (SEQ ID NO: 5), carries the *H. pylori* 26695 futC α(1,2)fucosyltransferase gene (Wang, G., Rasko, D. A., Sherburne, R. & Taylor, D. E. Mol Microbiol 31, 1265-1274 (1999)) and will also direct the production of 2'-FL in strain E403. In a preferred example, the plasmid pG180 (ColE1, thyA+, bla+, P$_{L2}$-wcfW, rcsA+) (SEQ ID NO: 6) carries the previously uncharacterized *Bacteriodes fragilis* NCTC 9343 wcfW α(1,2)fucosyltransferase gene of the current invention and directs the production of 2'-FL in *E. coli* strain E403.

Figure 8:
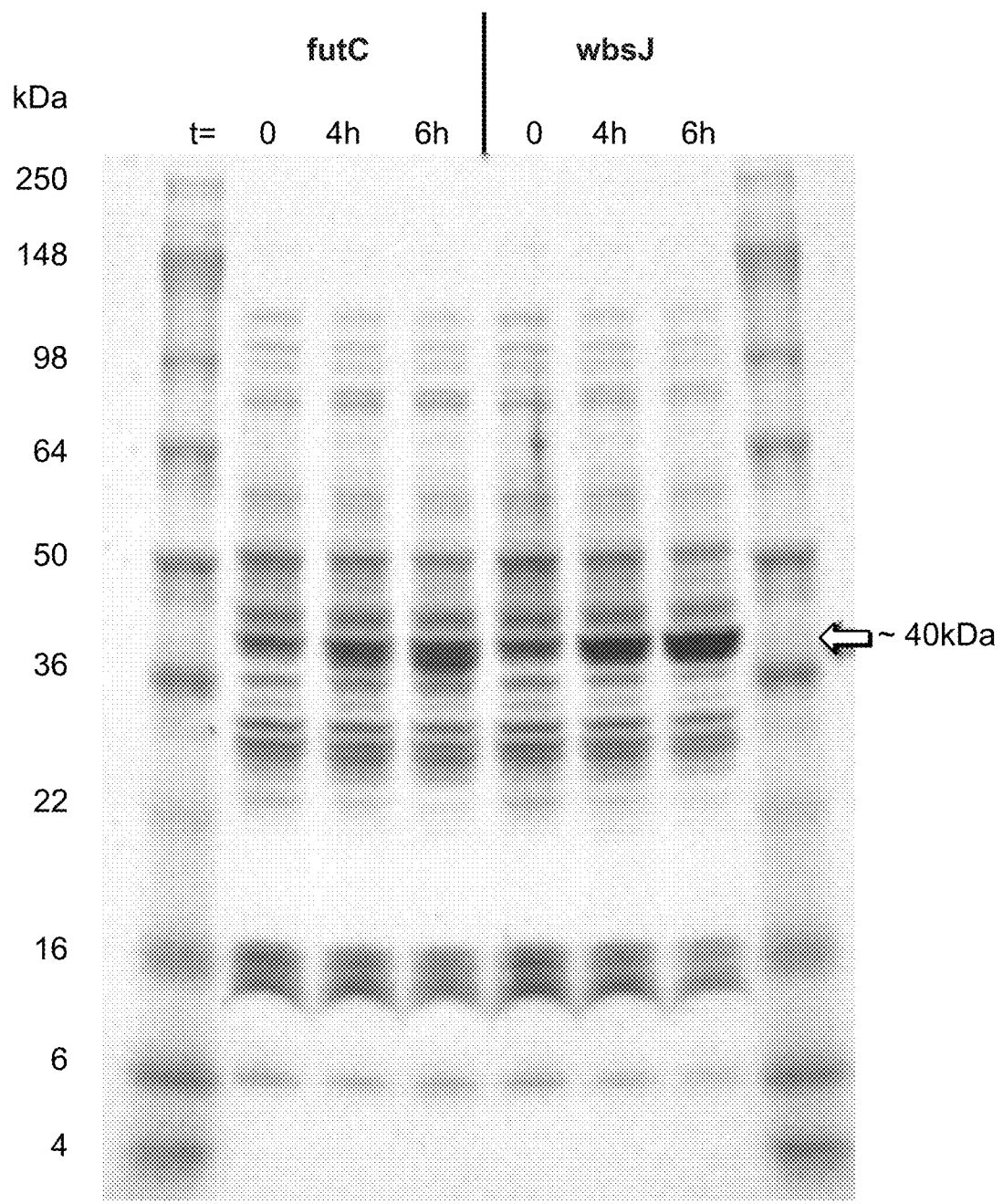
FIG. 8 is a photograph of a western blot of lysates of *E. coli* containing pG175 and expressing wbsJ, and of cells containing pG171, a pG175 derivative plasmid carrying the *H. pylori* 26695 futC gene in place of wbsJ and which expresses futC.
Figure 11:
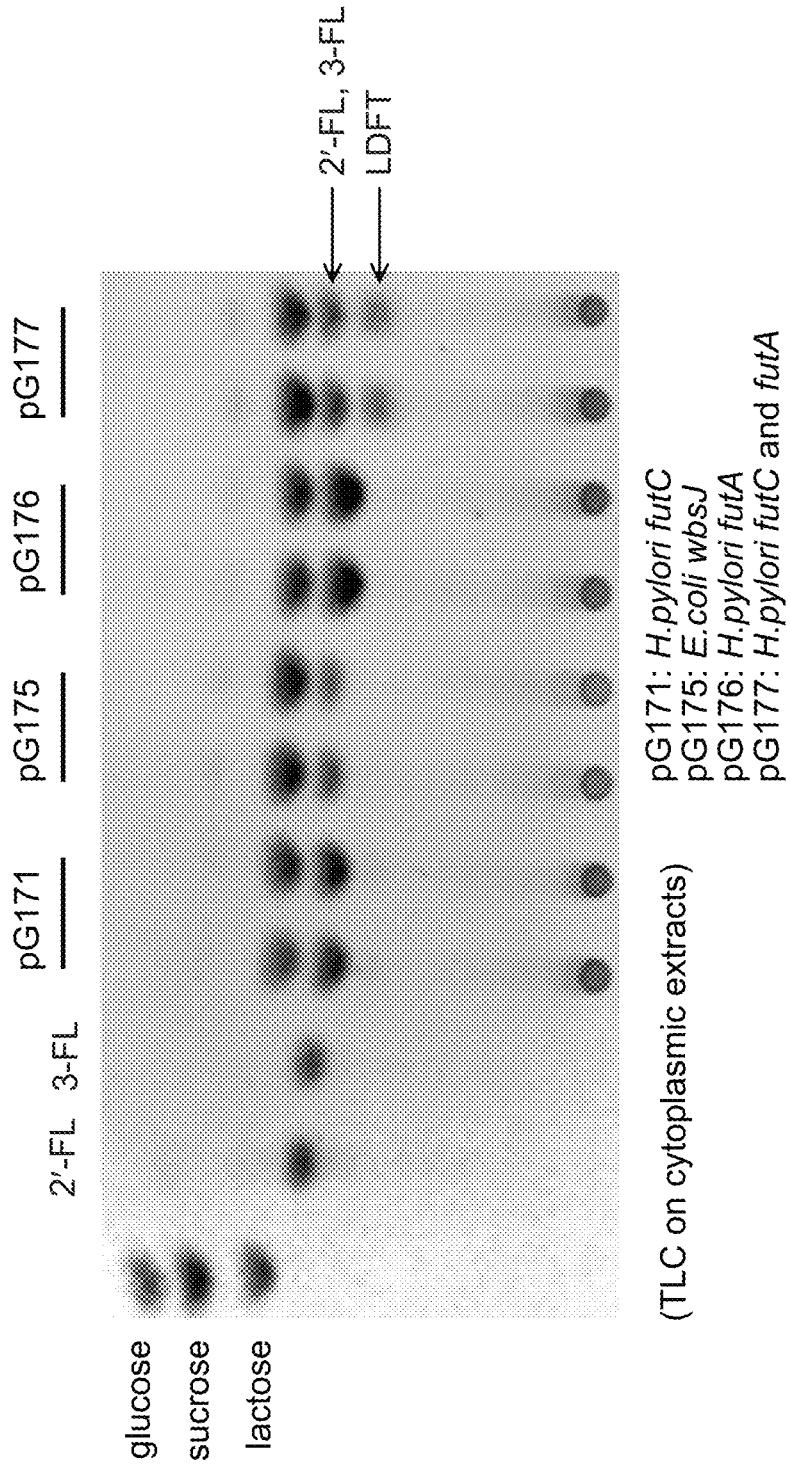
FIG. 11 is a photograph of a thin layer chromatogram of 2'-FL, 3FL, and LDFT (lactodifucotetraose) produced in *E. coli*, directed by plasmids pG171, pG175 (2'-FL), pG176 (3FL), and pG177 (LDFT, 2'-FL and 3FL).
Figure 16:
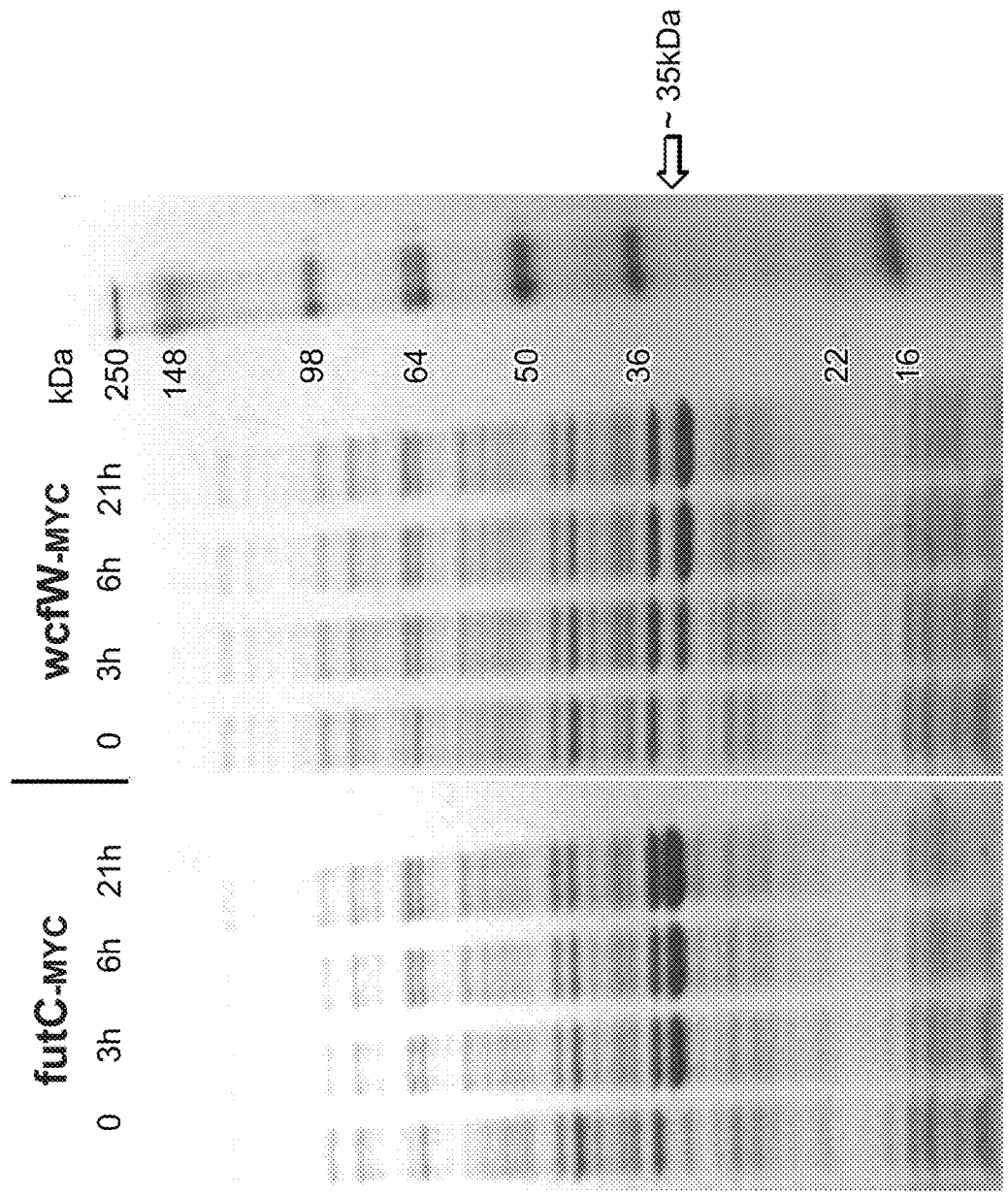
FIG. 16 is a photograph of a western blot of lysates of *E. coli* containing pG180, a pG175 derivative plasmid carrying the *B. fragilis* wcfW gene in place of wbsJ and which expresses wcfW, and of cells containing pG171, a pG175 derivative plasmid carrying the *H. pylori* 26695 futC gene in place of wbsJ and which expresses futC.
Figure 17:
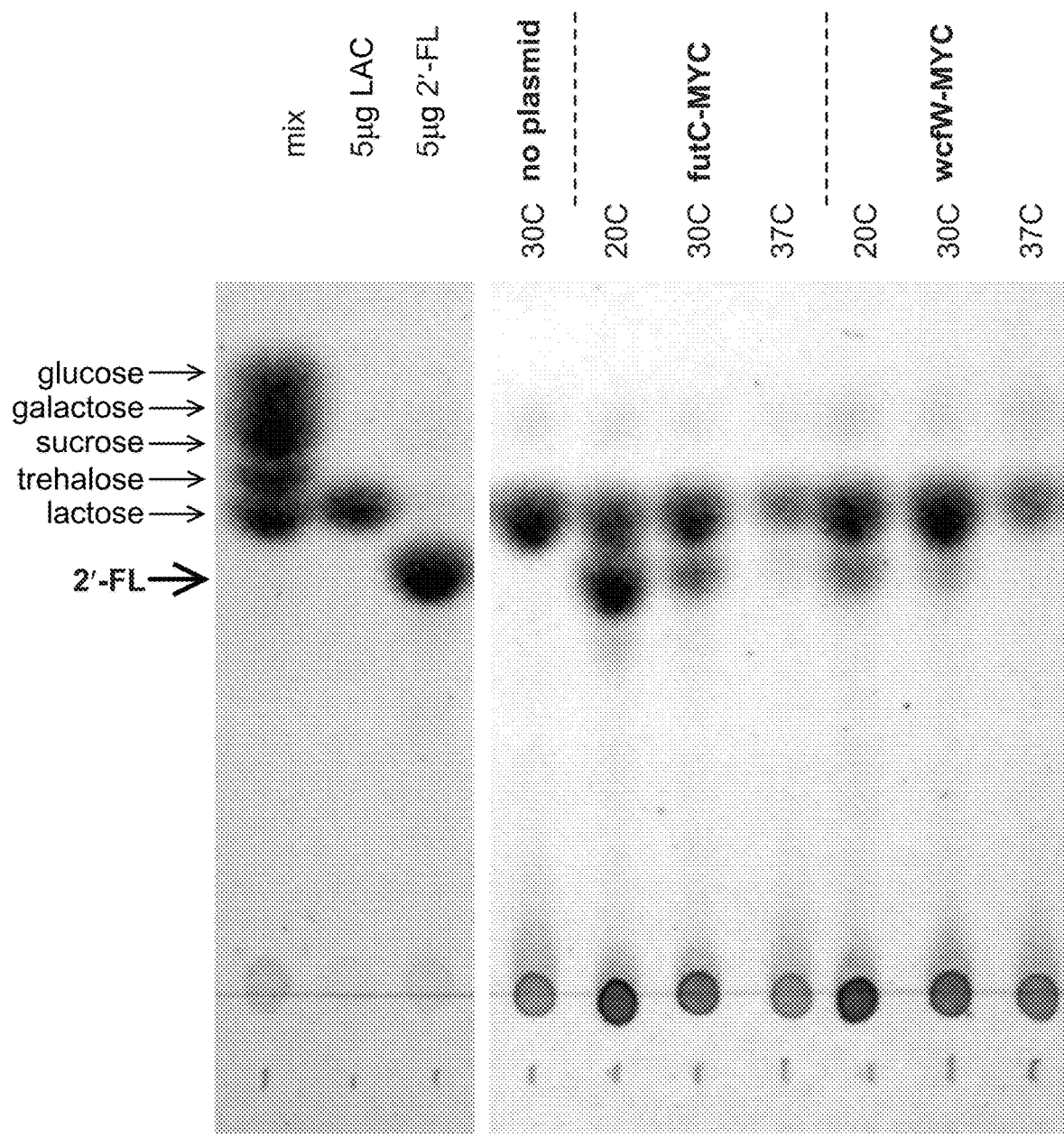
FIG. 17 is a photograph of a thin layer chromatogram of 2'-FL produced in *E. coli* by cells carrying plasmids pG180 or pG171 and induced for expression of wcfW or futC respectively.

The addition of tryptophan to the lactose-containing growth medium of cultures of any one of the strains E214, E390 or E403, when transformed with any one of the plasmids pG171, pG175 or pG180 leads, for each particular strain/plasmid combination, to activation of the host *E. coli* tryptophan utilization repressor TrpR, subsequent repression of P$_{trpB}$ and a consequent decrease in cytoplasmic cI levels, which results in a de-repression of P$_L$, expression of futC, wbsJ or wcfW, respectively, and production of 2'-FL. FIG. 8 is a coomassie blue-stained SDS PAGE gel of lysates of *E. coli* containing pG175 and expressing wbsJ, and of cells containing pG171 and expressing futC. Prominent stained protein bands running at a molecular weight of approximately 35 kDa are seen for both WbsJ and FutC at 4 and 6 h following P$_L$ induction (i.e., after addition of tryptophan). FIG. 16 is a coomassie blue-stained SDS PAGE gel of lysates of *E. coli* containing pG180 and expressing wcfW, and of cells containing pG171 and expressing *H. pylori* futC. Prominent stained bands for both WcfW and FutC are seen at a molecular weight of approximately 40 kDa at 4 and 6 h following P$_L$ induction (i.e., after addition of tryptophan to the growth medium). For 2'-FL production in small scale laboratory cultures (<100 ml) strains were grown at 30 C in a selective medium lacking both thymidine and tryptophan to early exponential phase (e.g. M9 salts, 0.5% glucose, 0.4% casaminoacids). Lactose was then added to a final concentration of 0.5 or 1%, along with tryptophan (200 μM final) to induce expression of the α(1,2) fucosyltransferase, driven from the P$_L$ promoter. At the end of the induction period (~24 h) TLC analysis was performed on aliquots of cell-free culture medium, or of heat extracts of cells (treatments at 98 C for 10 min, to release sugars contained within the cell). FIG. 11 shows a TLC analysis of cytoplasmic extracts of engineered *E. coli* cells transformed with pG175 or pG171. Cells were induced to express wbsJ or futC, respectively, and grown in the presence of lactose. The production of 2'-FL can clearly be seen in heat extracts of cells carrying either plasmid. FIG. 17 shows a TLC analysis of cytoplasmic extracts of engineered *E. coli* cells transformed with pG180 or pG171. Cells were induced to express wcfW or futC, respectively, and grown in the presence of lactose. The production of 2'-FL can clearly be seen with both plasmids. Prior to the present invention the wcfW gene had never been shown to encode a protein with demonstrated α(1,2) fucosyltransferase activity, or to utilize lactose as a sugar acceptor substrate.

The DNA sequence of the *Bacteroides fragilis* strain NCTC 9343 wcfW gene (protein coding sequence) is set forth below (SEQ ID NO: 4).

Example 3. 2'-FL Production in the Bioreactor

2'-FL can be produced in the bioreactor by any one of the host *E. coli* strains E214, E390 or E403, when transformed with any one of the plasmids pG171, pG175 or pG180. Growth of the transformed strain is performed in a minimal medium in a bioreactor, 10 L working volume, with control of dissolved oxygen, pH, lactose substrate, antifoam and nutrient levels. Minimal "FERM" medium is used in the bioreactor, which is detailed below.

Ferm (10 liters): Minimal medium comprising:
40 g $(NH_4)_2HPO_4$
100 g $KH_2PO_4$
10 g $MgSO_4.7H_2O$
40 g NaOH
Trace elements:
1.3 g NTA
0.5 g $FeSO_4.7H_2O$
0.09 g $MnCl_2.4H_2O$
0.09 g $ZnSO_4.7H_2O$
0.01 g $CoCl_2.6H_2O$
0.01 g $CuCl_2.2H_2O$
0.02 g $H_3BO_3$
0.01 g $Na_2MoO_4.2H_2O$ (pH 6.8)
Water to 10 liters
DF204 antifoam (0.1 ml/L)
150 g glycerol (initial batch growth), followed by fed batch mode with a 90% glycerol-1% $MgSO_4$-1× trace elements feed, at various rates for various times.

Figure 18:
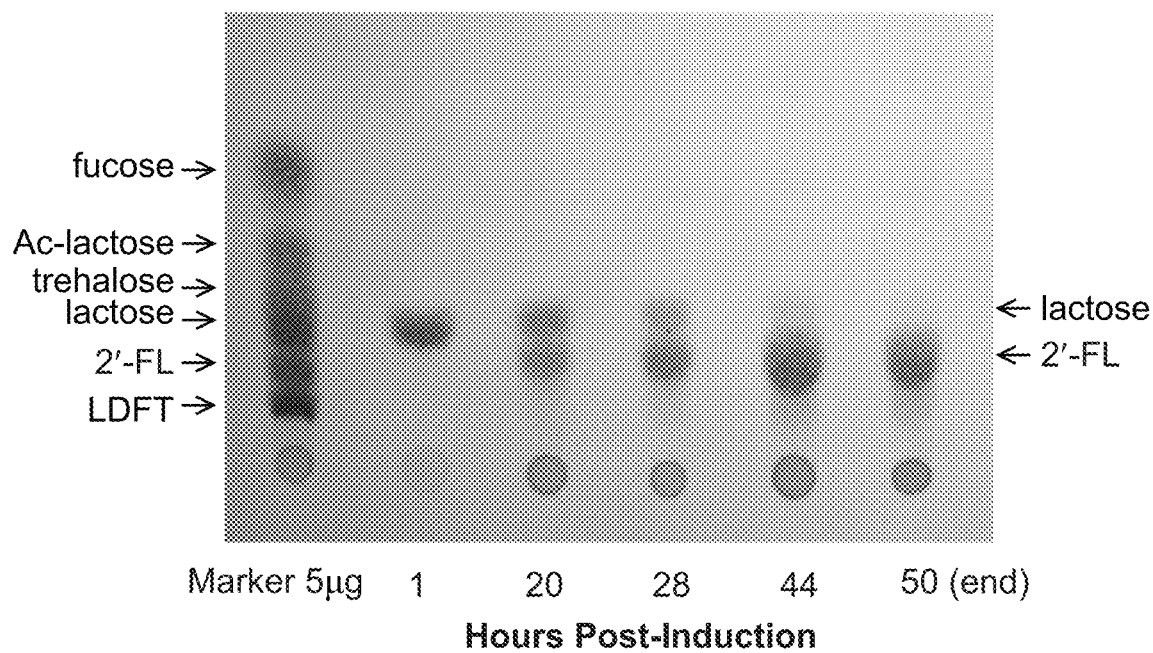
FIG. 18 is a photograph of a thin layer chromatogram showing the kinetics and extent of 2'-FL production in a 10 L bioreactor of *E. coli* host strain E403 transformed with plasmid pG171.

Production cell densities of $A_{600}$>100 are routinely achieved in these bioreactor runs. Briefly, a small bacterial culture is grown overnight in "FERM"—in the absence of either antibiotic or exogenous thymidine. The overnight culture (@~2 $A_{600}$) is used to inoculate a bioreactor (10 L working volume, containing "FERM") to an initial cell density of ~0.2 $A_{600}$. Biomass is built up in batch mode at 30° C. until the glycerol is exhausted ($A_{600}$~20), and then a fed batch phase is initiated utilizing glycerol as the limiting carbon source. At $A_{600}$~ 30, 0.2 g/L tryptophan is added to induce α(1,2) fucosyltransferase synthesis. An initial bolus of lactose is also added at this time. 5 hr later, a continuous slow feed of lactose is started in parallel to the glycerol feed. These conditions are continued for 48 hr (2'-FL production phase). At the end of this period, both the lactose and glycerol feeds are terminated, and the residual glycerol and lactose are consumed over a final fermentation period, prior to harvest. 2'-FL accumulates in the spent fermentation medium at concentrations as much as 30 times higher than in the cytoplasm. The specific yield in the spent medium varies between 10 and 50 g/L, depending on precise growth and induction conditions. FIG. 18 is a TLC of culture medium samples removed from a bioreactor at various times during a 2'-FL production run utilizing plasmid pG171 transformed into strain E403. All of the input lactose was converted to product by the end of the run, and product yield was approximately 25 g/L 2'-FL.

Example 4. 2'-Fucosyllactose Purification

2'-FL purification from *E. coli* fermentation broth is accomplished though five steps:
1. Clarification
  Fermentation broth is harvested and cells removed by sedimentation in a preparative centrifuge at 6000×g for 30 min. Each bioreactor run yields about 5-7 L of partially clarified supernatant. Clarified supernatants have a brown/orange coloration attributed to a fraction of caramelized sugars produced during the course of the fermentation, particularly by side-reactions promoted by the ammonium ions present in the fermentation medium.

2. Product Capture on Coarse Carbon

A column packed with coarse carbon (Calgon 12×40 TR) of ~1000 ml volume (dimension 5 cm diameter×60 cm length) is equilibrated with 1 column volume (CV) of water and loaded with clarified culture supernatant at a flow rate of 40 ml/min. This column has a total capacity of about 120 g of sugar (lactose). Following loading and sugar capture, the column is washed with 1.5 CV of water, then eluted with 2.5 CV of 50% ethanol or 25% isopropanol (lower concentrations of ethanol at this step (25-30%) may be sufficient for product elution). This solvent elution step releases about 95% of the total bound sugars on the column and a small portion of the color bodies (caramels). In this first step capture of the maximal amount of sugar is the primary objective. Resolution of contaminants is not an objective. The column can be regenerated with a 5 CV wash with water.

3. Evaporation

A volume of 2.5 L of ethanol or isopropanol eluate from the capture column is rotary-evaporated at 56 C and a sugar syrup in water is generated (this typically is a yellow-brown color). Alternative methods that could be used for this step include lyophilization or spray-drying.

4. Flash Chromatography on Fine Carbon and Ion Exchange Media

Figure 19:
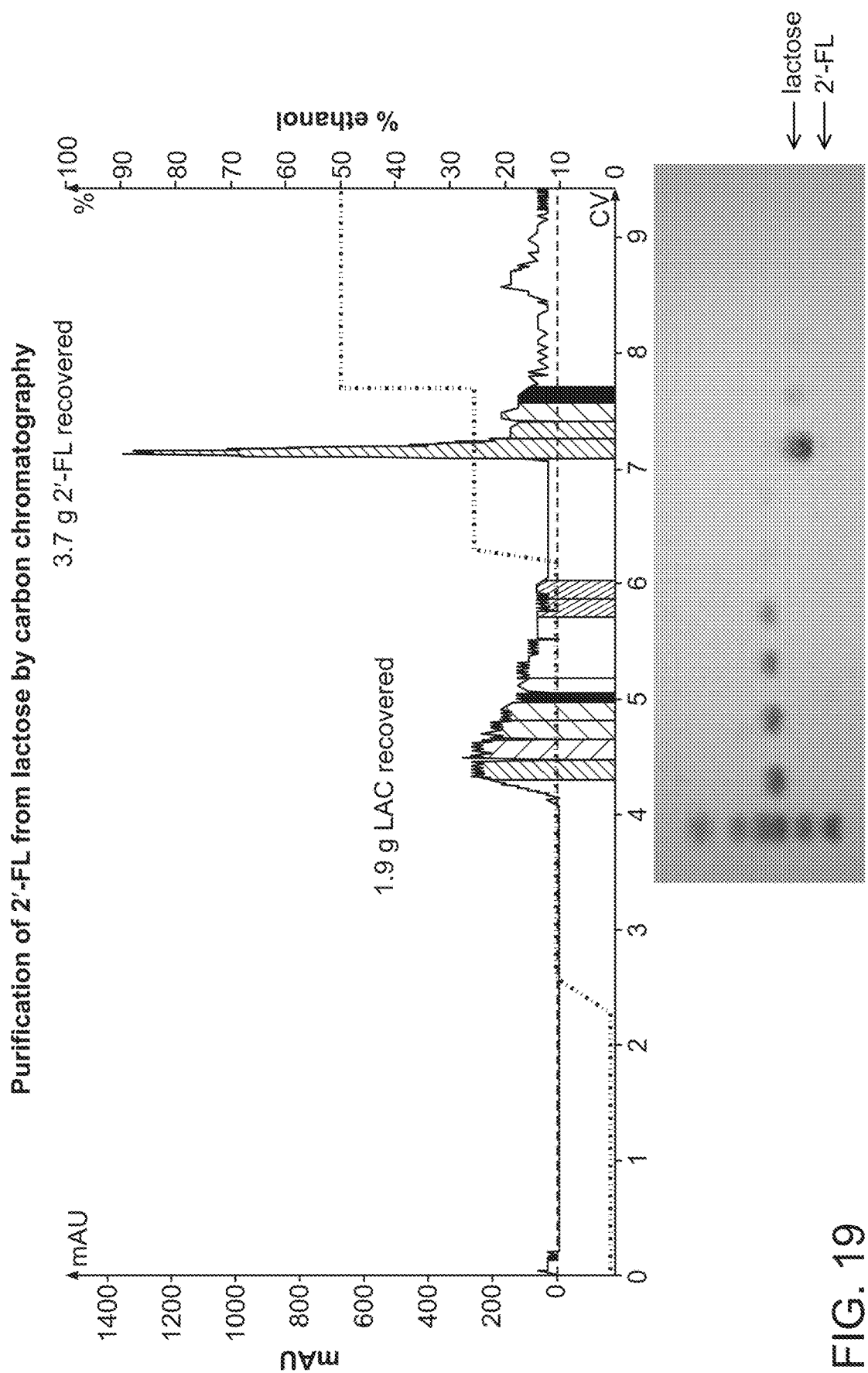
FIG. 19 is a column chromatogram and a TLC analysis of the resolution on a carbon column of a sample of 2'-FL made in *E. coli* from a lactose impurity.

A column (GE Healthcare HiScale50/40, 5×40 cm, max pressure 20 bar) connected to a Biotage Isolera One FLASH Chromatography System is packed with 750 ml of a Darco Activated Carbon G60 (100-mesh): Celite 535 (coarse) 1:1 mixture (both column packings obtained from Sigma). The column is equilibrated with 5 CV of water and loaded with sugar from step 3 (10-50 g, depending on the ratio of 2'-FL to contaminating lactose), using either a celite loading cartridge or direct injection. The column is connected to an evaporative light scattering (ELSD) detector to detect peaks of eluting sugars during the chromatography. A four-step gradient of isopropanol, ethanol or methanol is run in order to separate 2'-FL from monosaccharides (if present), lactose and color bodies. e.g., for B=ethanol: Step 1, 2.5 CV 0% B; Step 2, 4 CV 10% B (elutes monosaccharides and lactose contaminants); step 3, 4 CV 25% B (Elutes 2'-FL); step 4, 5 CV 50% B (elutes some of the color bodies and partially regenerates the column). Additional column regeneration is achieved using methanol @ 50% and isopropanol @ 50%. Fractions corresponding to sugar peaks are collected automatically in 120-ml bottles, pooled and directed to step 5. In certain purification runs from longer-than-normal fermentations, passage of the 2'-FL-containing fraction through anion-exchange and cation exchange columns can remove excess protein/DNA/caramel body contaminants. Resins tested successfully for this purpose are Dowex 22 and Toyopearl Mono-Q, for the anion exchanger, and Dowex 88 for the cation exchanger. Mixed bed Dowex resins have proved unsuitable as they tend to adsorb sugars at high affinity via hydrophobic interactions. FIG. 19 illustrates the performance of Darco G60:celite 1:1 in separating lactose from 2'-fucoyllactose when used in Flash chromatography mode.

5. Evaporation/Lyophilization 3.0 L of 25% B solvent fractions is rotary-evaporated at 56 C until dry. Clumps of solid sugar are re-dissolved in a minimum amount of water, the solution frozen, and then lyophilized. A white, crystalline, sweet powder (2'-FL) is obtained at the end of the process. 2'-FL purity obtained lies between 95 and 99%.

Sugars are routinely analyzed for purity by spotting 1 μl aliquots on aluminum-backed silica G60 Thin Layer Chromatography plates (10×20 cm; Macherey-Nagel). A mixture of LDFT (Rf=0.18), 2'-FL (Rf=0.24), lactose (Rf=0.30), trehalose (Rf=0.32), acetyl-lactose (Rf=0.39) and fucose (Rf=0.48) (5 g/L concentration for each sugar) is run alongside as standards. The plates are developed in a 50% butanol:25% acetic acid:25% water solvent until the front is within 1 cm from the top. Improved sugar resolution can be obtained by performing two sequential runs, drying the plate between runs. Sugar spots are visualized by spraying with α-naphtol in a sulfuric acid-ethanol solution (2.4 g α-naphtol in 83% (v/v) ethanol, 10.5% (v/v) sulfuric acid) and heating at 120 C for a few minutes. High molecular weight contaminants (DNA, protein, caramels) remain at the origin, or form smears with Rfs lower than LDFT.

Example 5. 3FL Production

Figure 9:
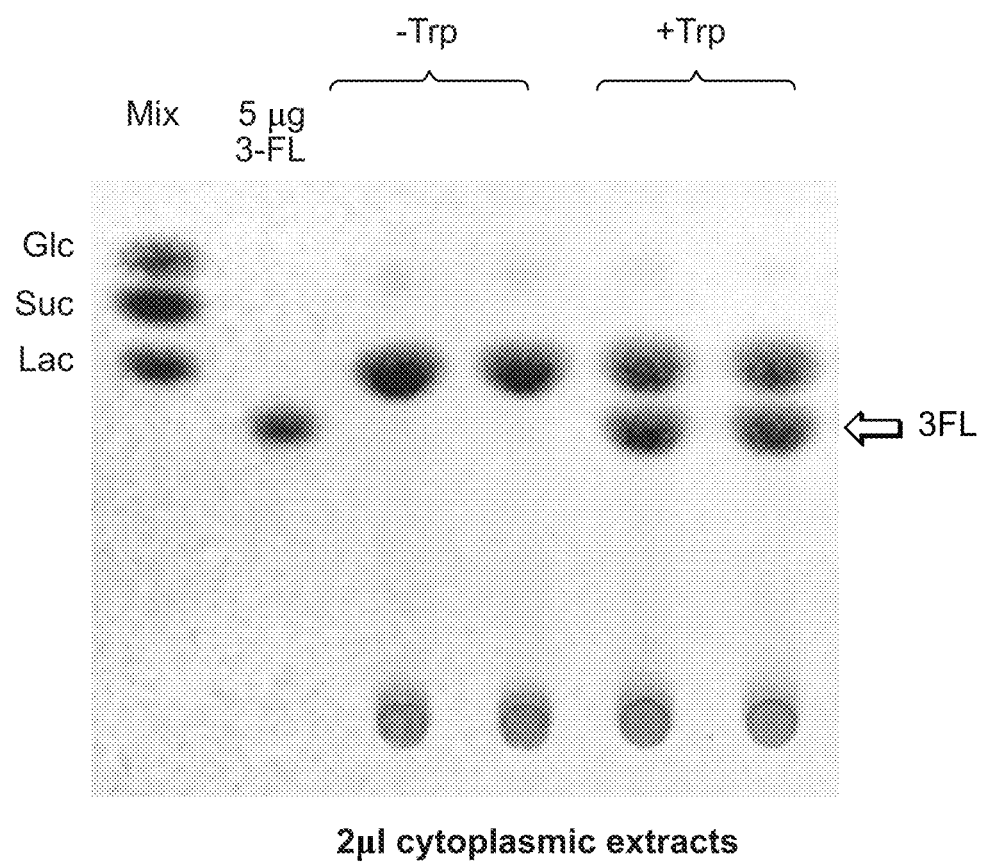
FIG. 9 is a photograph of a thin layer chromatogram of 3FL produced in *E. coli* containing the plasmid pG176 and induced for expression of the *H. pylori* 26695 α(1,3)fucosyltransferase gene futA by tryptophan addition.

Any one of *E. coli* host strains E214, E390 or E403, when transformed with a plasmid expressing an α(1,3)fucosyltransferase capable of using lactose as the sugar acceptor substrate, will produce the human milk oligosaccharide product, 3-fucosyllactose (3FL). FIG. 9 illustrates the pathways utilized in engineered strains of *E. coli* of this invention to achieve production of 3FL. For example, the plasmid pG176 (ColE1, thyA+, bla+, $P_{L2}$-futA, rcsA+) (SEQ ID NO: 2), is a derivative of pG175 in which the α(1,2) FT (wbsJ) sequence is replaced by the *Helicobacter pylori* futA gene (Dumon, C., Bosso, C., Utille, J. P., Heyraud, A. & Samain, E. Chembiochem 7, 359-365 (2006)). pG176 will direct the production of 3FL when transformed into any one of the host *E. coli* strains E214, E390 or E403. FIG. 11 shows a TLC analysis of 3FL production from E403 transformed with pG176. Additionally there are several other related bacterial-type α(1,3)-fucosyltransferases identified in *Helicobacter pylori* which could be used to direct synthesis of 3FL, e.g., "11639 FucTa" (Ge, Z., Chan, N. W., Palcic, M. M. & Taylor, D. E. J Biol Chem 272, 21357-21363 (1997); Martin, S. L., Edbrooke, M. R., Hodgman, T. C., van den Eijnden, D. H. & Bird, M. I. J Biol Chem 272, 21349-21356 (1997)) and "UA948 FucTa" (Rasko, D. A., Wang, G., Palcic, M. M. & Taylor, D. E. J Biol Chem 275, 4988-4994 (2000)). In addition to α(1,3)-fucosyltransferases from *H. pylori*, an α(1,3)fucosyltransferase (Hh0072, sequence accession AAP76669) isolated from *Helicobacter hepaticus* exhibits activity towards both non-sialylated and sialylated Type 2 oligosaccharide acceptor substrates (Zhang, L., Lau, K., Cheng, J., Yu, H., et al. Glycobiology (2010)). Furthermore, there are several additional bacterial α(1,3)-fucosyltransferases that may be used to make 3FL according to the methods of this invention. For example, close homologs of Hh0072 are found in H. *H. bilis* (HRAG_01092 gene, sequence accession EEO24035), and in *C. jejuni* (C1336_000250319 gene, sequence accession EFC31050).

3FL biosynthesis is performed as described above for 2'-FL, either at small scale in culture tubes and culture flasks, or in a bioreactor (10 L working volume) utilizing control of dissolved oxygen, pH, lactose substrate, antifoam and carbon:nitrogen balance. Cell densities of $A_{600}$~100 are reached in the bioreactor, and specific 3FL yields of up to 3 g/L have been achieved. Approximately half of the 3FL produced is found in the culture supernatant, and half inside the cells. Purification of 3FL from *E. coli* culture supernatants is achieved using an almost identical procedure to that described above for 2'-FL. The only substantive difference being that 3FL elutes from carbon columns at lower alcohol concentrations than does 2'-FL.

Example 6. The Simultaneous Production of Human Milk Oligosaccharides 2'-Fucosyllactose (2'-FL), 3-Fucosyllactose (3FL), and Lactodifucohexaose (LDFT) in *E. coli*

*E. coli* strains E214, E390 and E403 accumulate cytoplasmic pools of both lactose and GDP-fucose, as discussed above, and when transformed with plasmids expressing either an $\alpha(1,2)$ fucosyltransferase or an $\alpha(1,3)$ fucosyltransferase can synthesize the human milk oligosaccharides 2'-FL or 3FL respectively. The tetrasaccharide lactodifucotetrose (LDFT) is another major fucosylated oligosaccharide found in human milk, and contains both $\alpha(1,2)$- and $\alpha(1,3)$-linked fucose residues. pG177 (FIG. 10, SEQ ID NO: 3) is a derivative of pG175 in which the wbsJ gene is replaced by a two gene operon comprising the *Helicobacter pylori* futA gene and the *Helicobacter pylori* futC gene (i.e., an operon containing both an $\alpha(1,3)$- and $\alpha(1,2)$-fucosyltransferase). *E. coli* strains E214, E390 and E403 produce LDFT when transformed with plasmid pG177 and grown, either in small scale or in the bioreactor, as described above. In FIG. 11 (lanes pG177), LDFT made in *E. coli*, directed by pG177, was observed on analysis of cell extracts by thin layer chromatography.

Example 7. 3'-SL Synthesis in the *E. coli* Cytoplasm

The first step in the production of 3'-sialyllactose (3'-SL) in *E. coli* is generation of a host background strain that accumulates cytoplasmic pools of both lactose and CMP-Neu5Ac (CMP-sialic acid). Accumulation of cytoplasmic lactose is achieved through growth on lactose and inactivation of the endogenous *E. coli* β-galactosidase gene (lacZ), being careful to minimize polarity effects on lacY, the lac permease. This accumulation of a lactose pool has already been accomplished and is described above in *E. coli* hosts engineered for 2'-FL, 3FL and LDFT production.

Figure 5:
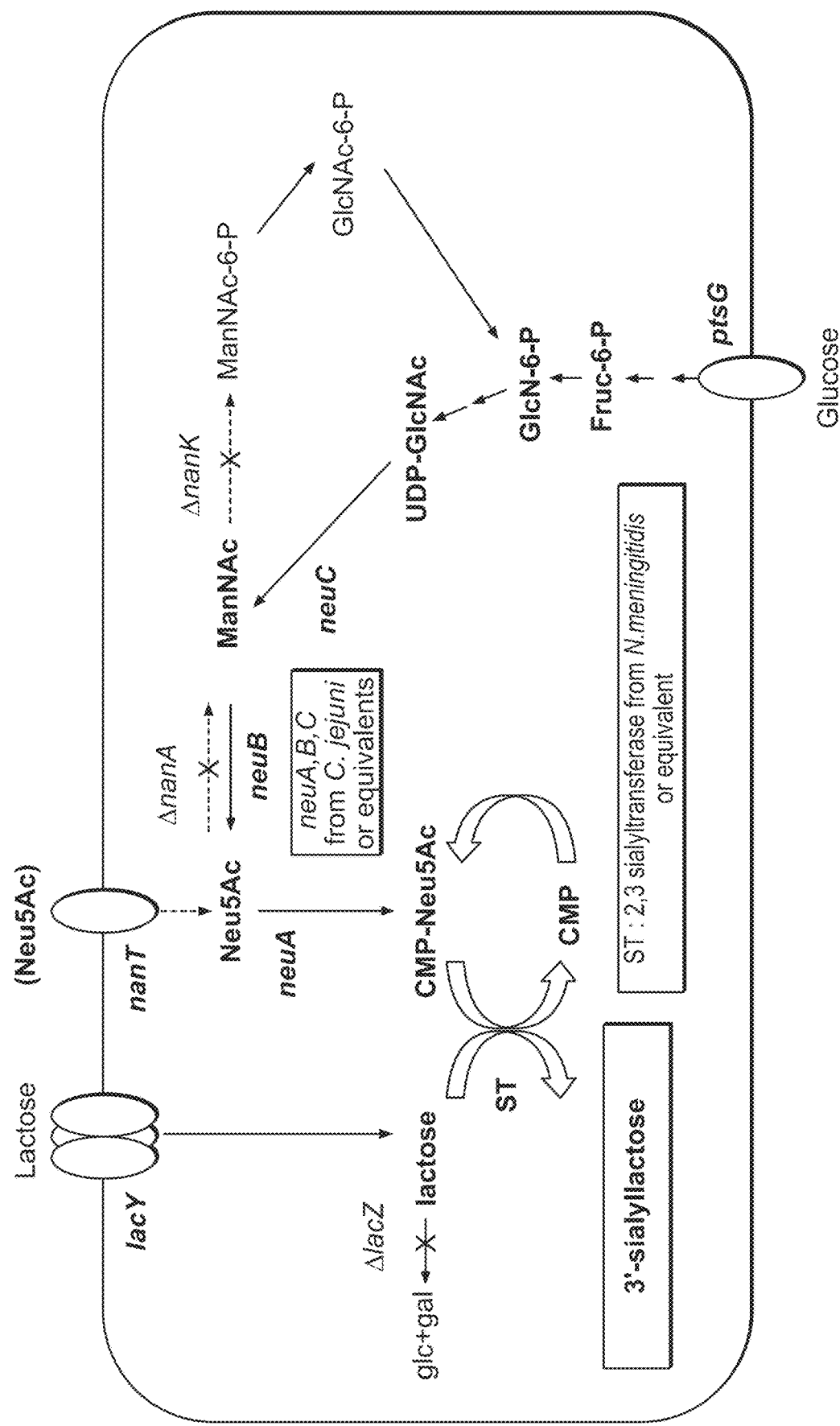
FIG. 5 is a schematic demonstrating metabolic pathways and the changes introduced into them to engineer 3'-sialyllactose (3'-SL) synthesis in *E. coli*. Abbreviations include: (Neu5Ac) N-acetylneuraminic acid, sialic acid; (nanT) sialic acid transporter; (ΔnanA) mutated N-acetylneuraminic acid lyase; (ManNAc) N-acetylmannosamine; (ΔnanK) mutated N-acetylmannosamine kinase; (ManNAc-6-P) N-acetylmannosamine-6-phosphate; (GlcNAc -6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; and (neuB), N-acetylneuraminic acid synthase.
Figure 6:
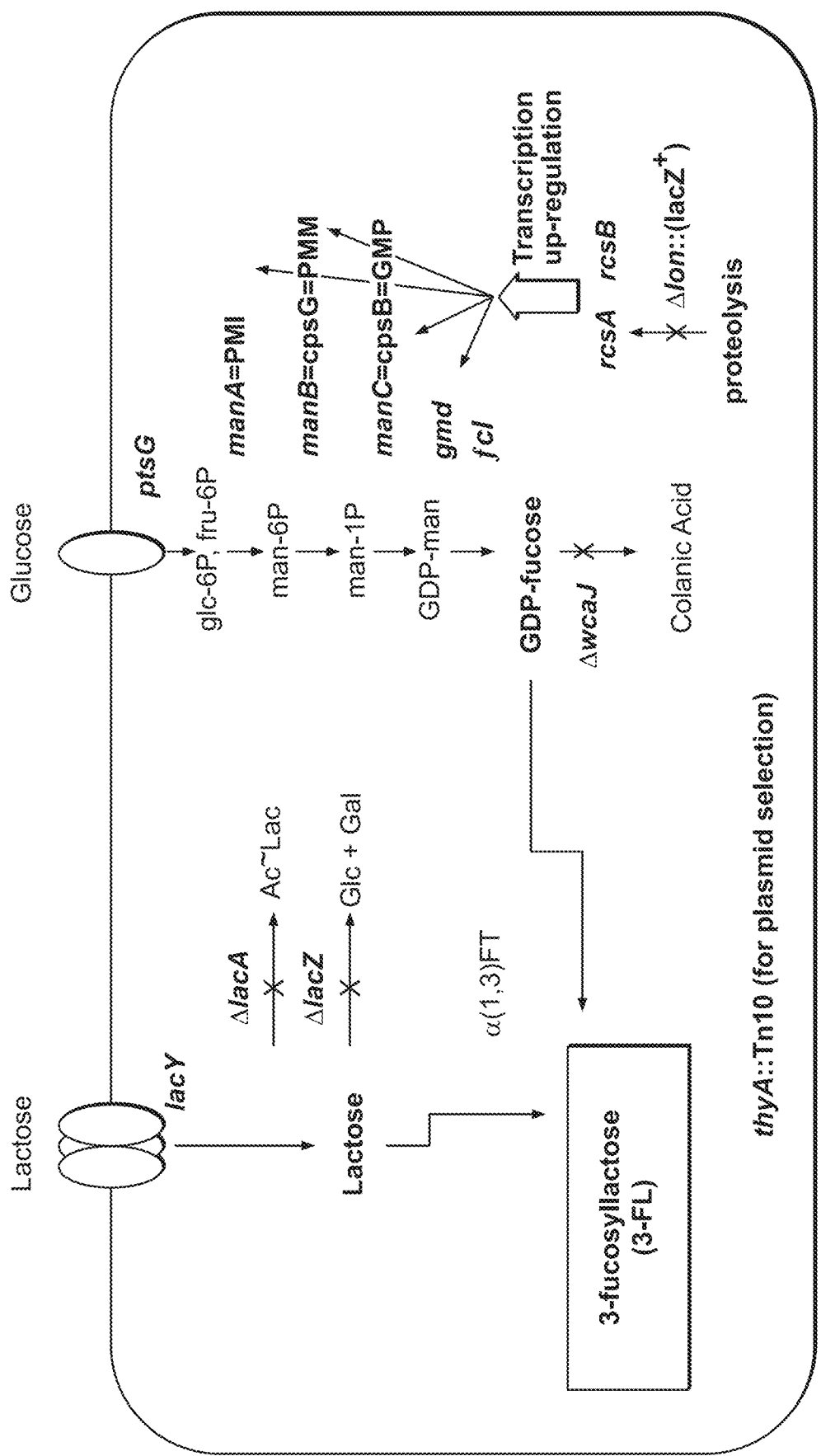
FIG. 6 is a schematic demonstrating metabolic pathways and the changes introduced into them to engineer 3-fucosyllactose (3-FL) synthesis in *E. coli*.

Specifically, a scheme to generate a cytoplasmic CMP-Neu5Ac pool, modified from methods known in the art, (e.g., Ringenberg, M., Lichtensteiger, C. & Vimr, E. Glycobiology 11, 533-539 (2001); Fierfort, N. & Samain, E. J Biotechnol 134, 261-265 (2008)), is shown in FIG. 5. Under this scheme, the *E. coli* K12 sialic acid catabolic pathway is first ablated through introduction of null mutations in endogenous nanA (N-acetylneuraminate lyase) and nanK (N-acetylmannosamine kinase) genes. By "sialic acid catabolic pathway" is meant a sequence of reactions, usually controlled and catalyzed by enzymes, which results in the degradation of sialic acid. An exemplary sialic acid catabolic pathway in *Escherichia coli* is set forth in FIG. 5. In the sialic acid catabolic pathway in FIG. 5, sialic acid (Neu5Ac; N-acetylneuraminic acid) is degraded by the enzymes NanA (N-acetylneuraminic acid lyase) and NanK (N-acetylmannosamine kinase). Other abbreviations for the sialic acid catabolic pathway in FIG. 5 include: (nanT) sialic acid transporter; (AnanA) mutated N-acetylneuraminic acid lyase; (ΔnanK) mutated N-acetylmannosamine kinase; (ManNAc-6-P) N-acetylmannosamine-6-phosphate; (GlcNAc-6-P) N-acetylglucosamine-6-phosphate; (GlcN-6-P) Glucosamine-6-phosphate; (Fruc-6-P) Fructose-6-phosphate; (neuA), CMP-N-acetylneuraminic acid synthetase; (CMP-Neu5Ac) CMP-N-acetylneuraminic acid; and (neuB), N-acetylneuraminic acid synthase.

Next, since *E. coli* K12 lacks a de novo sialic acid synthesis pathway, sialic acid synthetic capability is introduced through the provision of three recombinant enzymes; a UDP-GlcNAc 2-epimerase (e.g., neuC), a Neu5Ac synthase (e.g., neuB) and a CMP-Neu5Ac synthetase (e.g., neuA). Equivalent genes from *C. jejuni, E. coli* K1, *H. influenzae* or from *N. meningitides* can be utilized (interchangeably) for this purpose.

Figure 20:
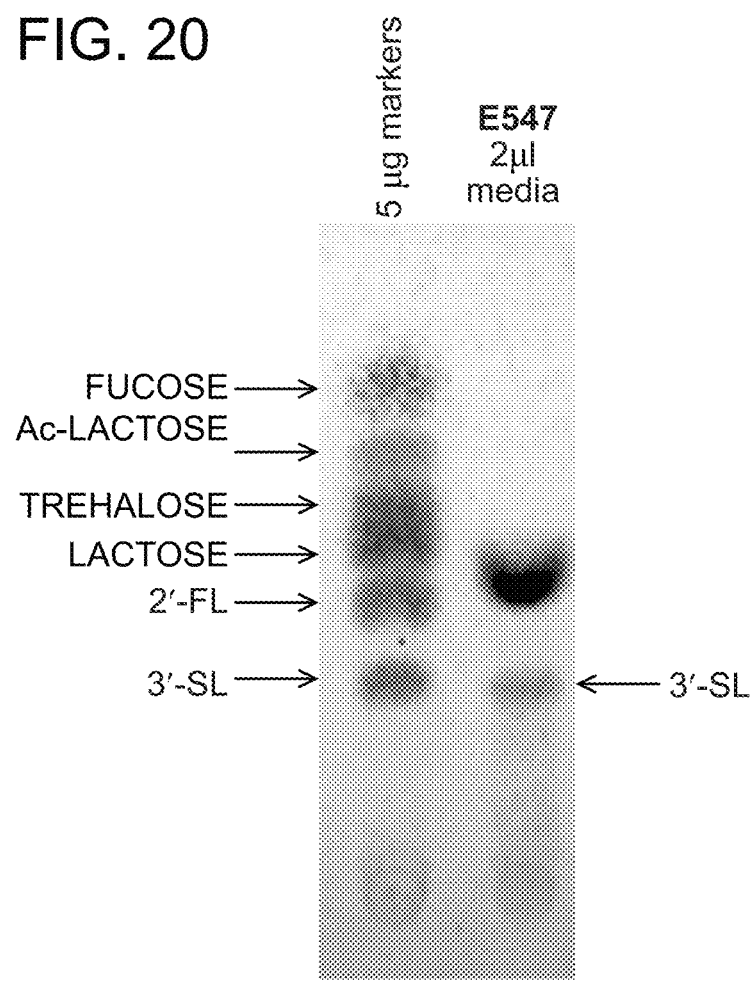
FIG. 20 is a photograph of a thin layer chromatogram showing 3'-SL in culture medium produced by *E. coli* strain E547, containing plasmids expressing a bacterial α(2,3) sialyltransferase and neuA, neuB and neuC.

The addition of sialic acid to the 3' position of lactose to generate 3'-sialyllactose is then achieved utilizing a bacterial-type $\alpha(2,3)$sialyltransferase, and numerous candidate genes have been described, including those from *N. meningitidis* and *N. gonorrhoeae* (Gilbert, M., Watson, D. C., Cunningham, A. M., Jennings, M. P., et al. J Biol Chem 271, 28271-28276 (1996); Gilbert, M., Cunningham, A. M., Watson, D. C., Martin, A., et al. Eur J Biochem 249, 187-194 (1997)). The *Neisseria* enzymes are already known to use lactose as an acceptor sugar. The recombinant *N. meningitidis* enzyme generates 3'-sialyllactose in engineered *E. coli* (Fierfort, N. & Samain, E. J Biotechnol 134, 261-265 (2008)). FIG. 20 shows a TLC analysis of culture media taken from a culture of *E. coli* strain E547 (ampC:: ($Pr_{trpB}\lambda cI^+$), $P_{lacI^q}(\Delta lacI-lacZ)_{158}lacY^+$, ΔacA, Δnan) and carrying plasmids expressing neuA,B,C and a bacterial-type $\alpha(2,3)$sialyltransferase. The presence of 3'-sialyllactose (3'-SL) in the culture media is clearly seen.

Example 8. The Production of Human Milk Oligosaccharide 3'-Sialyl-3-Fucosyllactose (3'-S3FL) in *E. coli*

Prior to the invention described herein, it was unpredictable that a combination of any particular fucosyltransferase gene and any particular sialyl-transferase gene in the same bacterial strain could produce 3'-S3FL. Described below are results demonstrating that the combination of a fucosyltransferase gene and a sialyl-transferase gene in the same Lac⁺ *E. coli* strain resulted in the production of 3'-S3FL. These unexpected results are likely due to the surprisingly relaxed substrate specificity of the particular fucosyltransferase and sialyl-transferase enzymes utilzied.

Humans synthesize the sialyl-Lewis X epitope utilizing different combinations of six $\alpha(1,3)$fucosyl- and six $\alpha(2,3)$ sialyl-transferases encoded in the human genome (de Vries, T., Knegtel, R. M., Holmes, E. H. & Macher, B. A. Glycobiology 11, 119R-128R (2001); Taniguchi, A. Curr Drug Targets 9, 310-316 (2008)). These sugar transferases differ not only in their tissue expression patterns, but also in their acceptor specificities. For example, human myeloid-type $\alpha(1,3)$ fucosyltransferase (FUT IV) will fucosylate Type 2 (Galβ1->4Glc/GlcNAc) chain-based acceptors, but only if they are non-sialylated. In contrast "plasma-type" $\alpha(1,3)$ fucosyltansferase (FUT VI) will utilize Type 2 acceptors whether or not they are sialylated, and the promiscuous "Lewis" $\alpha(1,3/4)$ fucosyltransferase (FUT III), found in breast and kidney, will act on sialylated and non-sialylated Type 1 (Galβ1->3GlcNAc) and Type 2 acceptors (Easton, E. W., Schiphorst, W. E., van Drunen, E., van der Schoot, C. E. & van den Eijnden, D. H. Blood 81, 2978-2986 (1993)). A similar situation exists for the family of human □ $\alpha(2,3)$ sialyl-transferases, with different enzymes exhibiting major differences in acceptor specificity (Legaigneur, P., Breton, C., El Battari, A., Guillemot, J. C., et al. J Biol Chem 276, 21608-21617 (2001); Jeanneau, C., Chazalet, V., Augé, C., Soumpasis, D. M., et al. J Biol Chem 279, 13461-13468 (2004)). This diversity in acceptor specificity highlights a key issue in the synthesis of 3'-sialyl-3-fucosyllactose (3'-

S3FL) in *E. coli*, i.e., to identify a suitable combination of fucosyl- and sialyl-transferases capable of acting cooperatively to synthesize 3'-S3FL (utilizing lactose as the initial acceptor sugar). However, since human and all other eukaryotic fucosyl- and sialyl-transferases are secreted proteins located in the lumen of the golgi, they are poorly suited for the task of 3'-S3FL biosynthesis in the bacterial cytoplasm.

Several bacterial pathogens are known to incorporate fucosylated and/or sialylated sugars into their cell envelopes, typically for reasons of host mimicry and immune evasion. For example; both *Neisseria meningitides* and *Campylobacter jejuni* are able to incorporate sialic acid through 2,3-linkages to galactose moieties in their capsular lipooligosaccharide (LOS) (Tsai, C. M., Kao, G. & Zhu, P. I Infection and Immunity 70, 407 (2002); Gilbert, M., Brisson, J. R., Karwaski, M. F., Michniewicz, J., et al. J Biol Chem 275, 3896-3906 (2000)), and some strains of *E. coli* incorporate α(1,2) fucose groups into lipopolysaccharide (LPS) (Li, M., Liu, X. W., Shao, J., Shen, J., et al. Biochemistry 47, 378-387 (2008); Li, M., Shen, J., Liu, X., Shao, J., et al. Biochemistry 47, 11590-11597 (2008)). Certain strains of *Helicobacter pylori* are able not only to incorporate α(2,3)-sialyl-groups, but also α(1,2)-, α(1,3)-, and α(1,4)-fucosyl-groups into LPS, and thus can display a broad range of human Lewis-type epitopes on their cell surface (Moran, A. P. Carbohydr Res 343, 1952-1965 (2008)). Most bacterial sialyl- and fucosyl-transferases operate in the cytoplasm, i.e., they are better suited to the methods described herein than are eukaryotic golgi-localized sugar transferases.

Strains of *E. coli* engineered to express the transferases described above accumulate a cytoplasmic pool of lactose, as well as an additional pool of either the nucleotide sugar GDP-fucose, or the nucleotide sugar CMP-Neu5Ac (CMP-sialic acid). Addition of these sugars to the lactose acceptor is performed in these engineered hosts using candidate recombinant α(1,3)-fucosyl- or α(2,3)-sialyl-transferases, generating 3-fucosyllactose and 3'-sialyllactose respectively. Finally, the two synthetic capabilities are combined into a single *E. coli* strain to produce 3'-S3FL.

An *E. coli* strain that accumulates cytoplasmic pools of both lactose and GDP-fucose has been developed. This strain, when transformed with a plasmid over-expressing an α(1,2)fucosyltransferase, produces 2'-fucosyllactose (2'-FL) at levels of ~10-50 g/L of bacterial culture medium. A substitution of the α(1,2) fucosyltransferase in this host with an appropriate α(1,3) fucosyltransferase leads to the production of 3-fucosyllactose (3FL). The bacterial α(1,3) fucosyltransferase then works in conjunction with a bacterial α(2,3)sialyltransferase to make the desired product, 3'-S3FL.

An α(1,3)fucosyltransferase (Hh0072) isolated from *Helicobacter hepaticus* exhibits activity towards both non-sialylated and sialylated Type 2 oligosaccharide acceptor substrates (Zhang, L., Lau, K., Cheng, J., Yu, H., et al. Glycobiology (2010)). This enzyme is cloned, expressed, and evaluated to measure utilization of a lactose acceptor and to evaluate production of 3FL in the context of the current GDP-fucose-producing *E. coli* host. Hh0072 is also tested in concert with various bacterial α(2,3)sialyltransferases for its competence in 3'-S3FL synthesis. As alternatives to Hh0072, there are two characterized homologous bacterial-type 3-fucosyltransferases identified in *Helicobacter pylori*, "11639 FucTa" (Ge, Z., Chan, N. W., Palcic, M. M. & Taylor, D. E. J Biol Chem 272, 21357-21363 (1997); Martin, S. L., Edbrooke, M. R., Hodgman, T. C., van den Eijnden, D. H. & Bird, M. I. J Biol Chem 272, 21349-21356 (1997)) and "UA948 FucTa" (Rasko, D. A., Wang, G., Palcic, M. M. & Taylor, D. E. J Biol Chem 275, 4988-4994 (2000)). These two paralogs exhibit differing acceptor specificities, "11639 FucTa" utilizes only Type 2 acceptors and is a strict α(1,3)-fucosyltransferase, whereas "UA948 FucTa" has relaxed acceptor specificity (utilizing both Type1 and Type 2 acceptors) and is able to generate both α(1,3)- and α(1,4)-fucosyl linkages. The precise molecular basis of this difference in specificity was determined (Ma, B., Lau, L. H., Palcic, M. M., Hazes, B. & Taylor, D. E. J Biol Chem 280, 36848-36856 (2005)), and characterization of several additional α(1,3)-fucosyltransferase paralogs from a variety of additional *H. pylori* strains revealed significant strain-to-strain acceptor specificity diversity.

In addition to the enzymes from *H. pylori* and *H. hepaticus*, other bacterial α(1,3)-fucosyltransferases are optionally used. For example, close homologs of Hh0072 are found in *H. bilis* (HRAG_01092 gene, sequence accession EEO24035), and in *C. jejuni* (C1336_000250319 gene, sequence accession EFC31050).

Described below is 3'-S3FL synthesis in *E. coli*. The first step towards this is to combine into a single *E. coli* strain the 3-fucosyllactose synthetic ability, outlined above, with the ability to make 3'-sialyllactose, also outlined above. All of the chromosomal genetic modifications discussed above are introduced into a new host strain, which will then simultaneously accumulate cytoplasmic pools of the 3 specific precursors; lactose, GDP-fucose and CMP-Neu5Ac. This "combined" strain background is then used to host simultaneous production of an α(1,3)fucosyltransferase with an α(2,3)sialyltransferase, with gene expression driven either off two compatible multicopy plasmids or with both enzyme genes positioned on the same plasmid as an artificial operon. Acceptor specificities for some of the bacterial α(1,3)fucosyltransferases and α(2,3)sialyltransferases, particularly with respect to fucosylation of 3'-sialyllactose and sialylation of 3-fucosyllactose and different combinations of α(1,3)fucosyltransferase and α(2,3)sialyltransferase enzymes are evaluated. Production levels and ratios of 3'-SL, 3FL and 3'-S3FL are monitored, e.g., by TLC, with confirmation of identity by NMR and accurate quantitation either by calibrated mass spectrometry utilizing specific ion monitoring, or by capillary electrophoresis (Bao, Y., Zhu, L. & Newburg, D. S. Simultaneous quantification of sialyloligosaccharides from human milk by capillary electrophoresis. Anal Biochem 370, 206-214 (2007)).

The sequences corresponding to the SEQ ID NOs described herein are provided below.

The sequence of PG175 is set forth below (SEQ ID NO: 1):

```
TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATATGCGGTGTGAAATACCGCACAGATGCGTAAGGAGAAA

ATACCGCATCAGGCGCCTCCTCAACCTGTATATTCGTAAACCACGCCCAATGGGAGCTGTCTCAGGTTTGTTCCT
```

-continued

```
GATTGGTTACGGCGCGTTTCGCATCATTGTTGAGTTTTTCCGCCAGCCCGACGCGCAGTTTACCGGTGCCTGGGT
GCAGTACATCAGCATGGGGCAAATTCTTTCCATCCCGATGATTGTCGCGGGTGTGATCATGATGGTCTGGGCATA
TCGTCGCAGCCCACAGCAACACGTTTCCTGAGGAACCATGAAACAGTATTTAGAACTGATGCAAAAAGTGCTCGA
CGAAGGCACACAGAAAAACGACCGTACCGGAACCGGAACGCTTTCCATTTTTGGTCATCAGATGCGTTTTAACCT
GCAAGATGGATTCCCGCTGGTGACAACTAAACGTTGCCACCTGCGTTCCATCATCCATGAACTGCTGTGGTTTCT
GCAGGGCGACACTAACATTGCTTATCTACACGAAAACAATGTCACCATCTGGGACGAATGGGCCGATGAAAACGG
CGACCTCGGGCCAGTGTATGGTAAACAGTGGCGCGCCTGGCCAACGCCAGATGGTCGTCATATTGACCAGATCAC
TACGGTACTGAACCAGCTGAAAAACGACCCGGATTCGCGCCGCATTATTGTTTCAGCGTGGAACGTAGGCGAACT
GGATAAAATGGCGCTGGCACCGTGCCATGCATTCTTCCAGTTCTATGTGGCAGACGGCAAACTCTCTTGCCAGCT
TTATCAGCGCTCCTGTGACGTCTTCCTCGGCCTGCCGTTCAACATTGCCAGCTACGCGTTATTGGTGCATATGAT
GGCGCAGCAGTGCGATCTGGAAGTGGGTGATTTTGTCTGGACCGGTGGCGACACGCATCTGTACAGCAACCATAT
GGATCAAACTCATCTGCAATTAAGCCGCGAACCGCGTCCGCTGCCGAAGTTGATTATCAAACGTAAACCCGAATC
CATCTTCGACTACCGTTTCGAAGACTTTGAGATTGAAGGCTACGATCCGCATCCGGGCATTAAAGCGCCGGTGGC
TATCTAATTACGAAACATCCTGCCAGAGCCGACGCCAGTGTGCGTCGGTTTTTTTACCCTCCGTTAAATTCTTCG
AGACGCCTTCCCGAAGGCGCCATTCGCCATTCAGGCTGCGCAACTGTTGGGAAGGGCGATCGGTGCGGGCCTCTT
CGCTATTACGCCAGCTGGCGAAAGGGGATGTGCTGCAAGGCGATTAAGTTGGGTAACGCCAGGGTTTTCCCAGT
CACGACGTTGTAAAACGACGGCCAGTGCCAAGCTTTCTTTAATGAAGCAGGGCATCAGGACGGTATCTTTGTGGA
GAAAGCAGAGTAATCTTATTCAGCCTGACTGGTGGGAAACCACCAGTCAGAATGTGTTAGCGCATGTTGACAAAA
ATACCATTAGTCACATTATCCGTCAGTCGGACGACATGGTAGATAACCTGTTTATTATGCGTTTTGATCTTACGT
TTAATATTACCTTTATGCGATGAAACGGTCTTGGCTTTGATATTCATTTGGTCAGAGATTTGAATGGTTCCCTGA
CCTGCCATCCACATTCGCAACATACTCGATTCGGTTCGGCTCAATGATAACGTCGGCATATTTAAAAACGAGGTT
ATCGTTGTCTCTTTTTTCAGAATATCGCCAAGGATATCGTCGAGAGATTCCGGTTTAATCGATTTAGAACTGATC
AATAAATTTTTTCTGACCAATAGATATTCATCAAAATGAACATTGGCAATTGCCATAAAAACGATAAATAACGTA
TTGGGATGTTGATTAATGATGAGCTTGATACGCTGACTGTTAGAAGCATCGTGGATGAAACAGTCCTCATTAATA
AACACCACTGAAGGGCGCTGTGAATCACAAGCTATGGCAAGGTCATCAACGGTTTCAATGTCGTTGATTTCTCTT
TTTTTAACCCCTCTACTCAACAGATACCCGGTTAAACCTAGTCGGGTGTAACTACATAAATCCATAATAATCGTT
GACATGGCATACCCTCACTCAATGCGTAACGATAATTCCCCTTACCTGAATATTTCATCATGACTAAACGGAACA
ACATGGGTCACCTAATGCGCCACTCTCGCGATTTTTCAGGCGGACTTACTATCCCGTAAAGTGTTGTATAATTTG
CCTGGAATTGTCTTAAAGTAAAGTAAATGTTGCGATATGTGAGTGAGCTTAAAACAAATATTTCGCTGCAGGAGT
ATCCTGGAAGATGTTCGTAGAAGCTTACTGCTCACAAGAAAAAAGGCACGTCATCTGACGTGCCTTTTTTATTTG
TACTACCCTGTACGATTACTGCAGCTCAGTTATTATAATTTTACCCACGATTCGGGAATAATATCATGTTTAAT
ATCTTTCTTAAACCATTTACTCGGAGCAATTACTGTTTTATTTTTATTTTCATTTAACCAAGCAGCCCACCAACT
GAAAGAACTATTTGAAATTATATTATTTTTACATTTACTCATAAGCAGCATATCTAATTCAACATGATAAGCATC
ACCTTGAACAAAACATATTTGATTATTAAAAAATATATTTTCCCTGCACCACTTTATATCATCAGAAAAAATGAA
GAGAAGGGTTTTTTATTAATAACACCTTTATTCATCAAATAATCAATGGCACGTTCAAAATATTTTTCACTACA
TGTGCCATGAGTTTCATTTGCTATTTTACTGGAAACATAATCACCTCTTCTAATATGTAATGAACAAGTATCATT
TTCTTTAATTAAATTAAGCAATTCATTTTGATAACTATTAAACTTGGTTTTAGGTTGAAATTCCTTTATCAACTC
ATGCCTAAATTCCTTAAAATATTTTTCAGTTTGAAAATAACCGACGATTTTTTTATTTATACTTTTGGTATCAAT
ATCTGGATCATACTCTAAACTTTTCTCAACGTAATGCTTTCTGAACATTCCTTTTTTCATGAAATGTGGGATTTT
TTCGGAAAATAAGTATTTTTCAAATGGCCATGCTTTTTTTACAAATTCTGAACTACAAGATAATTCAACTAATCT
```

-continued

```
TAATGGATGAGTTTTATATTTTACTGCATCAGATATATCAACAGTCAAATTTTGATGAGTTCTTTTTGCAATAGC

AAATGCAGTTGCATACTGAAACATTTGATTACCAAGACCACCAATAATTTTAACTTCCATATGTATATCTCCTTC

TTCTAGAATTCTAAAAATTGATTGAATGTATGCAAATAAATGCATACACCATAGGTGTGGTTTAATTTGATGCCC

TTTTTCAGGGCTGGAATGTGTAAGAGCGGGGTTATTTATGCTGTTGTTTTTTGTTACTCGGGAAGGGCTTTACC

TCTTCCGCATAAACGCTTCCATCAGCGTTTATAGTTAAAAAAATCTTTCGGAACTGGTTTTGCGCTTACCCCAAC

CAACAGGGGATTTGCTGCTTTCCATTGAGCCTGTTTCTCTGCGCGACGTTCGCGGCGGCGTGTTTGTGCATCCAT

CTGGATTCTCCTGTCAGTTAGCTTTGGTGGTGTGTGGCAGTTGTAGTCCTGAACGAAAACCCCCCGCGATTGGCA

CATTGGCAGCTAATCCGGAATCGCACTTACGGCCAATGCTTCGTTTCGTATCACACACCCCAAAGCCTTCTGCTT

TGAATGCTGCCCTTCTTCAGGGCTTAATTTTTAAGAGCGTCACCTTCATGGTGGTCAGTGCGTCCTGCTGATGTG

CTCAGTATCACCGCCAGTGGTATTTATGTCAACACCGCCAGAGATAATTTATCACCGCAGATGGTTATCTGTATG

TTTTTTATATGAATTTATTTTTTGCAGGGGGGCATTGTTTGGTAGGTGAGAGATCAATTCTGCATTAATGAATCG

GCCAACGCGCGGGGAGAGGCGGTTTGCGTATTGGGCGCTCTTCCGCTTCCTCGCTCACTGACTCGCTGCGCTCGG

TCGTTCGGCTGCGGCGAGCGGTATCAGCTCACTCAAAGGCGGTAATACGGTTATCCACAGAATCAGGGGATAACG

CAGGAAAGAACATGTGAGCAAAAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGTGGCGAAACCCGACAGGACTAT

AAAGATACCAGGCGTTTCCCCCTGGAAGCTCCCTCGTGCGCTCTCCTGTTCCGACCCTGCCGCTTACCGGATACC

TGTCCGCCTTTCTCCCTTCGGGAAGCGTGGCGCTTTCTCATAGCTCACGCTGTAGGTATCTCAGTTCGGTGTAGG

TCGTTCGCTCCAAGCTGGGCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTAGAAGGACAGTATTTGGTA

TCTGCGCTCTGCTGAAGCCAGTTACCTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAAAGGATCTCAAGAAGATCCTTTGATCT

TTTCTACGGGGTCTGACGCTCAGTGGAACGAAAACTCACGTTAAGGGATTTTGGTCATGAGATTATCAAAAAGGA

TCTTCACCTAGATCCTTTTAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGTTCATCCATAGTTGCCTGAC

TCCCCGTCGTGTAGATAACTACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAGCGCAGAAGTGGTCCTGCAA

CTTTATCCGCCTCCATCCAGTCTATTAATTGTTGCCGGGAAGCTAGAGTAAGTAGTTCGCCAGTTAATAGTTTGC

GCAACGTTGTTGCCATTGCTACAGGCATCGTGGTGTCACGCTCGTCGTTTGGTATGGCTTCATTCAGCTCCGGTT

CCCAACGATCAAGGCGAGTTACATGATCCCCCATGTTGTGCAAAAAAGCGGTTAGCTCCTTCGGTCCTCCGATCG

TTGTCAGAAGTAAGTTGGCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAATAGTGTATGCGGCGACCGA

GTTGCTCTTGCCCGGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAACCCACTCGTGCAC

CCAACTGATCTTCAGCATCTTTTACTTTCACCAGCGTTTCTGGGTGAGCAAAAACAGGAAGGCAAAATGCCGCAA

AAAAGGGAATAAGGGCGACACGGAAATGTTGAATACTCATACTCTTCCTTTTTCAATATTATTGAAGCATTTATC
```

AGGGTTATTGTCTCATGAGCGGATACATATTTGAATGTATTTAGAAAAATAAACAAATAGGGGTTCCGCGCACAT

TTCCCCGAAAAGTGCCACCTGACGTCTAAGAAACCATTATTATCATGACATTAACCTATAAAAATAGGCGTATCA

CGAGGCCCTTTCGTC

The sequence of pG176 is set forth below (SEQ ID NO: 2):

TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATATGCGGTGTGAAATACCGCACAGATGCGTAAGGAGAAA

ATACCGCATCAGGCGCCATGAAACAGTATTTAGAACTGATGCAAAAAGTGCTCGACGAAGGCACACAGAAAAACG

ACCGTACCGGAACCGGAACGCTTTCCATTTTTGGTCATCAGATGCGTTTTAACCTGCAAGATGGATTCCCGCTGG

TGACAACTAAACGTTGCCACCTGCGTTCCATCATCCATGAACTGCTGTGGTTTCTGCAGGGCGACACTAACATTG

CTTATCTACACGAAAACAATGTCACCATCTGGGACGAATGGGCCGATGAAAACGGCGACCTCGGGCCAGTGTATG

GTAAACAGTGGCGCGCCTGGCCAACGCCAGATGGTCGTCATATTGACCAGATCACTACGGTACTGAACCAGCTGA

AAAACGACCCGGATTCGCGCCGCATTATTGTTTCAGCGTGGAACGTAGGCGAACTGGATAAAATGGCGCTGGCAC

CGTGCCATGCATTCTTCCAGTTCTATGTGGCAGACGGCAAACTCTCTTGCCAGCTTTATCAGCGCTCCTGTGACG

TCTTCCTCGGCCTGCCGTTCAACATTGCCAGCTACGCGTTATTGGTGCATATGATGGCGCAGCAGTGCGATCTGG

AAGTGGGTGATTTTGTCTGGACCGGTGGCGACACGCATCGTACAGCAACCATATGGATCAAACTCATCTGCAAT

TAAGCCGCGAACCGCGTCCGCTGCCGAAGTTGATTATCAAACGTAAACCCGAATCCATCTTCGACTACCGTTTCG

AAGACTTTGAGATTGAAGGCTACGATCCGCATCCGGGCATTAAAGCGCCGGTGGCTATCTAAGGCGCCATTCGCC

ATTCAGGCTGCGCAACTGTTGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTGTAAAACGACGGCCAGTGC

CAAGCTTTCTTTAATGAAGCAGGGCATCAGGACGGTATCTTTGTGGAGAAAGCAGAGTAATCTTATTCAGCCTGA

CTGGTGGGAAACCACCAGTCAGAATGTGTTAGCGCATGTTGACAAAAATACCATTAGTCACATTATCCGTCAGTC

GGACGACATGGTAGATAACCTGTTTATTATGCGTTTTGATCTTACGTTTAATATTACCTTTATGCGATGAAACGG

TCTTGGCTTTGATATTCATTTGGTCAGAGATTTGAATGGTTCCCTGACCTGCCATCCACATTCGCAACATACTCG

ATTCGGTTCGGCTCAATGATAACGTCGGCATATTTAAAAACGAGGTTATCGTTGTCTCTTTTTTCAGAATATCGC

CAAGGATATCGTCGAGAGATTCCGGTTTAATCGATTTAGAACTGATCAATAAATTTTTTCTGACCAATAGATATT

CATCAAAATGAACATTGGCAATTGCCATAAAAACGATAAATAACGTATTGGGATGTTGATTAATGATGAGCTTGA

TACGCTGACTGTTAGAAGCATCGTGGATGAAACAGTCCTCATTAATAAACACCACTGAAGGGCGCTGTGAATCAC

AAGCTATGGCAAGGTCATCAACGGTTTCAATGTCGTTGATTTCTCTTTTTTTAACCCCTCTACTCAACAGATACC

CGGTTAAACCTAGTCGGGTGTAACTACATAAATCCATAATAATCGTTGACATGGCATACCCTCACTCAATGCGTA

ACGATAATTCCCCTTACCTGAATATTTCATCATGACTAAACGGAACAACATGGGTCACCTAATGCGCCACTCTCG

CGATTTTTCAGGCGGACTTACTATCCCGTAAAGTGTTGTATAATTTGCCTGGAATTGTCTTAAAGTAAAGTAAAT

GTTGCGATATGTGAGTGAGCTTAAAACAAATATTTCGCTGCAGGAGTATCCTGGAAGATGTTCGTAGAAGCTTAC

TGCTCACAAGAAAAAGGCACGTCATCTGACGTGCCTTTTTTATTTGTACTACCCTGTACGATTACTGCAGCTCG

AGTTAATTCAAATCTTCTTCAGAAATCAATTTTTGTTCCAAACCCAATTTTTTAACCAACTTTCTCACCGCGCGC

AACAAAGGCAAGGATTTTTGATAAGCTTTGCGATAGATTTTAAAAGTGGTGTTTTGAGAGAGTTCTAATAAAGGC

GAAGCGTTTTGTAAAAGCCGGTCATAATTAACCCTCAAATCATCATAATTAACCCTCAAATCATCAATGGATACT

AACGGCTTATGCAGATCGTACTCCCACATGAAAGATGTTGAGAATTTGTGATAAATCGTATCGTTTTCTAAAATC

GTTTTAAAAAAATCTAGGATTTTTTTAAAACTCAAATCTTGGTAAAAGTAAGCTTTCCCATCAAGGGTGTTTAAA

-continued

```
GGGTTTTCATAGAGCATGTCTAAATAAGCGTTTGGGTGCGTGTGCAGGTATTTGATATAATCAATCGCTTCATCA

AAGTTGTTGAAATCATGCACATTCACAAAACTTTTAGGGTTAAAATCTTTCGCCACGCTGGGACTCCCCAATAA

ATAGGAATGGTATGGCTAAAATACGCATCAAGGATTTTTTCGGTTACATAGCCATAACCTTGCGAGTTTTCAAAA

CAGAGATTGAACTTGTATTGGCTTAAAAACTCGCTTTTGTTTCCAACCTTATAGCCTAAAGTGTTTCTCACACTT

CCTCCCCCAGTAACTGGCTCTATGGAATTTAGAGCGTCATAAAAAGCGTTCCTCATAGGAGCGTTAGCGTTGCTC

GCTACAAAACTGGCAAACCCTCTTTTTAAAAGATCGCTCTCATCATTCACTACTGCGCACAAATTAGGGTGGTTT

TCTTTAAAATGATGAGAGGGTTTTTTTAAAGCATAAAGGCTGTTGTCTTTGAGTTTGTAGGGCGCAGTGGTGTCA

TTAACAAGCTCGGCTTTATAGTGCAAATGGGCATAATACAAAGGCATTCTCAAATAACGATCATTAAAATCCAAT

TCATCAAAGCCTATGGCGTAATCAAAGAGGTTGAAATTAGGTGATTCGTTTTCACCGGTGTAAAACACTCGTTTA

GTGTTTTGATAAGATAAAATCTTTCTAGCCGCTCCAAGAGGATTGCTAAAAACTAGATCTGAAAATTCATTGGGG

TTTTGGTGGAGGGTGATTGCGTAGCGTTGGCTTAGGATAAAATAAAGAACGCTCTTTTTAAATTCTTTAATTTCT

TCATCTCCCCACCAATTCGCCACAGCGATTTTTAGGGGGGGGGGGGGAGATTTAGAGGCCATTTTTTCAATGGAA

GCGCTTTCTATAAAGGCGTCTAATAGGGGTTGGAACATATGTATATCTCCTTCTTGAATTCTAAAAATTGATTGA

ATGTATGCAAATAAATGCATACACCATAGGTGTGGTTTAATTTGATGCCCTTTTTCAGGGCTGGAATGTGTAAGA

GCGGGGTTATTTATGCTGTTGTTTTTTGTTACTCGGGAAGGGCTTTACCTCTTCCGCATAAACGCTTCCATCAG

CGTTTATAGTTAAAAAAATCTTTCGGAACTGGTTTTGCGCTTACCCCAACCAACAGGGGATTTGCTGCTTTCCAT

TGAGCCTGTTTCTCTGCGCGACGTTCGCGGCGGCGTGTTTGTGCATCCATCTGGATTCTCCTGTCAGTTAGCTTT

GGTGGTGTGTGGCAGTTGTAGTCCTGAACGAAAACCCCCGCGATTGGCACATTGGCAGCTAATCCGGAATCGCA

CTTACGGCCAATGCTTCGTTTCGTATCACACACCCCAAAGCCTTCTGCTTTGAATGCTGCCCTTCTTCAGGGCTT

AATTTTTAAGAGCGTCACCTTCATGGTGGTCAGTGCGTCCTGCTGATGTGCTCAGTATCACCGCCAGTGGTATTT

ATGTCAACACCGCCAGAGATAATTTATCACCGCAGATGGTTATCTGTATGTTTTTTATATGAATTTATTTTTGC

AGGGGGGCATTGTTTGGTAGGTGAGAGATCAATTCTGCATTAATGAATCGGCCAACGCGCGGGGAGAGGCGGTTT

GCGTATTGGGCGCTCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACATGTGAGCAAAAGG

CCAGCAAAAGGCCAGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGGCGTTTCCCCCTGG

AAGCTCCCTCGTGCGCTCTCCTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTTGAGTCCAACCCGGTAAGACA

CGACTTATCGCCACTGGCAGCAGCCACTGGTAACAGGATTAGCAGAGCGAGGTATGTAGGCGGTGCTACAGAGTT

CTTGAAGTGGTGGCCTAACTACGGCTACACTAGAAGGACAGTATTTGGTATCTGCGCTCTGCTGAAGCCAGTTAC

CTTCGGAAAAAGAGTTGGTAGCTCTTGATCCGGCAAACAAACCACCGCTGGTAGCGGTGGTTTTTTTGTTTGCAA

GCAGCAGATTACGCGCAGAAAAAAAGGATCTCAAGAAGATCCTTTGATCTTTTCTACGGGGTCTGACGCTCAGTG

GAACGAAAACTCACGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACCAATGCTTAATCAGTGA

GGCACCTATCTCAGCGATCTGTCTATTTCGTTCATCCATAGTTGCCTGACTCCCCGTCGTGTAGATAACTACGAT

ACGGGAGGGCTTACCATCTGGCCCCAGTGCTGCAATGATACCGCGAGACCCACGCTCACCGGCTCCAGATTTATC

AGCAATAAACCAGCCAGCCGGAAGGGCCGAGCGCAGAAGTGGTCCTGCAACTTTATCCGCCTCCATCCAGTCTAT

TAATTGTTGCCGGGAAGCTAGAGTAAGTAGTTCGCCAGTTAATAGTTTGCGCAACGTTGTTGCCATTGCTACAGG

CATCGTGGTGTCACGCTCGTCGTTTGGTATGGCTTCATTCAGCTCCGGTTCCCAACGATCAAGGCGAGTTACATG
```

-continued

```
ATCCCCCATGTTGTGCAAAAAAGCGGTTAGCTCCTTCGGTCCTCCGATCGTTGTCAGAAGTAAGTTGGCCGCAGT

GTTATCACTCATGGTTATGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACGTTCTTCGGGGCGAAAACTCTC

AAGGATCTTACCGCTGTTGAGATCCAGTTCGATGTAACCCACTCGTGCACCCAACTGATCTTCAGCATCTTTTAC

TTTCACCAGCGTTTCTGGGTGAGCAAAACAGGAAGGCAAATGCCGCAAAAAAGGGAATAAGGGCGACACGGAA

ATGTTGAATACTCATACTCTTCCTTTTTCAATATTATTGAAGCATTTATCAGGGTTATTGTCTCATGAGCGGATA

CATATTTGAATGTATTTAGAAAAATAAACAAATAGGGGTTCCGCGCACATTTCCCCGAAAAGTGCCACCTGACGT

CTAAGAAACCATTATTATCATGACATTAACCTATAAAAATAGGCGTATCACGAGGCCCTTTCGTC
```

The sequence of pG177 is set forth below (SEQ ID NO: 3):

```
TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATATGCGGTGTGAAATACCGCACAGATGCGTAAGGAGAAA

ATACCGCATCAGGCGCCATGAAACAGTATTTAGAACTGATGCAAAAAGTGCTCGACGAAGGCACACAGAAAAACG

ACCGTACCGGAACCGGAACGCTTTCCATTTTTGGTCATCAGATGCGTTTTAACCTGCAAGATGGATTCCCGCTGG

TGACAACTAAACGTTGCCACCTGCGTTCCATCATCCATGAACTGCTGTGGTTTCTGCAGGGCGACACTAACATTG

CTTATCTACACGAAAACAATGTCACCATCTGGGACGAATGGGCCGATGAAAACGGCGACCTCGGGCCAGTGTATG

GTAAACAGTGGCGCGCCTGGCCAACGCCAGATGGTCGTCATATTGACCAGATCACTACGGTACTGAACCAGCTGA

AAAACGACCCGGATTCGCGCCGCATTATTGTTTCAGCGTGGAACGTAGGCGAACTGGATAAAATGGCGCTGGCAC

CGTGCCATGCATTCTTCCAGTTCTATGTGGCAGACGGCAAACTCTCTTGCCAGCTTTATCAGCGCTCCTGTGACG

TCTTCCTCGGCCTGCCGTTCAACATTGCCAGCTACGCGTTATTGGTGCATATGATGGCGCAGCAGTGCGATCTGG

AAGTGGGTGATTTTGTCTGGACCGGTGGCGACACGCATCTGTACAGCAACCATATGGATCAAACTCATCTGCAAT

TAAGCCGCGAACCGCGTCCGCTGCCGAAGTTGATTATCAAACGTAAACCCGAATCCATCTTCGACTACCGTTTCG

AAGACTTTGAGATTGAAGGCTACGATCCGCATCCGGGCATTAAAGCGCCGGTGGCTATCTAAGGCGCCATTCGCC

ATTCAGGCTGCGCAACTGTTGGGAAGGGCGATCGGTGCGGGCCTCTTCGCTATTACGCCAGCTGGCGAAAGGGGG

ATGTGCTGCAAGGCGATTAAGTTGGGTAACGCCAGGGTTTTCCCAGTCACGACGTTGTAAAACGACGGCCAGTGC

CAAGCTTTCTTTAATGAAGCAGGGCATCAGGACGGTATCTTTGTGGAGAAAGCAGAGTAATCTTATTCAGCCTGA

CTGGTGGGAAACCACCAGTCAGAATGTGTTAGCGCATGTTGACAAAAATACCATTAGTCACATTATCCGTCAGTC

GGACGACATGGTAGATAACCTGTTTATTATGCGTTTTGATCTTACGTTTAATATTACCTTTATGCGATGAAACGG

TCTTGGCTTTGATATTCATTTGGTCAGAGATTTGAATGGTTCCCTGACCTGCCATCCACATTCGCAACATACTCG

ATTCGGTTCGGCTCAATGATAACGTCGGCATATTTAAAAACGAGGTTATCGTTGTCTCTTTTTTCAGAATATCGC

CAAGGATATCGTCGAGAGATTCCGGTTTAATCGATTTAGAACTGATCAATAAATTTTTTCTGACCAATAGATATT

CATCAAAATGAACATTGGCAATTGCCATAAAAACGATAAATAACGTATTGGGATGTTGATTAATGATGAGCTTGA

TACGCTGACTGTTAGAAGCATCGTGGATGAAACAGTCCTCATTAATAAACACCACTGAAGGGCGCTGTGAATCAC

AAGCTATGGCAAGGTCATCAACGGTTTCAATGTCGTTGATTTCTCTTTTTTTAACCCCTCTACTCAACAGATACC

CGGTTAAACCTAGTCGGGTGTAACTACATAAATCCATAATAATCGTTGACATGGCATACCCTCACTCAATGCGTA

ACGATAATTCCCCTTACCTGAATATTTCATCATGACTAAACGGAACAACATGGGTCACCTAATGCGCCACTCTCG

CGATTTTTCAGGCGGACTTACTATCCCGTAAAGTGTTGTATAATTTGCCTGGAATTGTCTTAAAGTAAAGTAAAT

GTTGCGATATGTGAGTGAGCTTAAAACAAATATTTCGCTGCAGGAGTATCCTGGAAGATGTTCGTAGAAGCTTAC
```

-continued

```
TGCTCACAAGAAAAAAGGCACGTCATCTGACGTGCCTTTTTTATTTGTACTACCCTGTACGATTACTGCAGCTCG

AGTTAATTCAAATCTTCTTCAGAAATCAATTTTTGTTCAGCGTTATACTTTTGGGATTTTACCTCAAAATGGGAT

TCTATTTTCACCCACTCCTTACAAAGGATATTCTCATGCCCAAAAAGCCAGTGTTTGGGCCAATAATGATTTTT

TCTGGATTTTCTATCAAATAGGCCGCCCACCAGCTATAAGTGCTATTAGCGATAATGCCATGCTGACAAGATTGC

ATGAGCAGCATGTCCCAATACGCCTCTTCTTCTTTATCCCTAGTGGTCATGTCCATAAAAGGGTAGCCAAGATCA

AGATTTTGCGTGAATTCTAAGTCTTCGCAAAACACAAAAAGCTCCATGTTTGGCACGCGCTTTGCCATATACTCA

AGCGCCTTTTTTGATAGTCAATACCAAGCTGACAGCCAATCCCCACATAATCCCCTCTTCTTATATGCACAAAC

ACGCTGTTTTTAGCGGCTAAAATCAAAGAAAGCTTGCACTGATATTCTTCCTCTTTTTTATTATTATTCTTATTA

TTTTCGGGTGGTGGTGGTAGAGTGAAGGTTTGCTTGATTAAAGGGGATATAGCATCAAAGTATCGTGGATCTTGG

AAATAGCCAAAAAAATAAGTCAAGCGGCTTGGCTTTAGCAATTTAGGCTCGTATTCAAAAACGATTTCTTGACTC

ACCCTATCAAATCCCATGCATTTGAGCGCGTCTCTTACTAGCTTGGGGAGGTGTTGCATTTTAGCTATAGCGATT

TCTTTCGCGCTCGCATAGGGCAAATCAATAGGGAAAAGTTCTAATTGCATTTTCCTATCGCTCCAATCAAAAGAA

GTGATATCTAACAGCACAGGCGTATTAGAGTGTTTTTGCAAACTTTTAGCGAAAGCGTATTGAAACATTTGATTC

CCAAGCCCTCCGCAAATTTGCACCACCTTAAAAGCCATATGTATATCTCCTTCTTGCTCGAGTTAATTCAAATCT

TCTTCAGAAATCAATTTTTGTTCCAAACCCAATTTTTTAACCAACTTTCTCACCGCGCGCAACAAAGGCAAGGAT

TTTTGATAAGCTTTGCGATAGATTTTAAAAGTGGTGTTTTGAGAGAGTTCTAATAAAGGCGAAGCGTTTTGTAAA

AGCCGGTCATAATTAACCCTCAAATCATCATAATTAACCCTCAAATCATCAATGGATACTAACGGCTTATGCAGA

TCGTACTCCCACATGAAAGATGTTGAGAATTTGTGATAAATCGTATCGTTTTCTAAAATCGTTTTAAAAAAATCT

AGGATTTTTTAAAACTCAAATCTTGGTAAAAGTAAGCTTTCCCATCAAGGGTGTTTAAAGGGTTTTCATAGAGC

ATGTCTAAATAAGCGTTTGGGTGCGTGTGCAGGTATTTGATATAATCAATCGCTTCATCAAAGTTGTTGAAATCA

TGCACATTCACAAAACTTTTAGGGTTAAAATCTTTCGCCACGCTGGGACTCCCCAATAAATAGGAATGGTATGG

CTAAAATACGCATCAAGGATTTTTTCGGTTACATAGCCATAACCTTGCGAGTTTTCAAAACAGAGATTGAACTTG

TATTGGCTTAAAAACTCGCTTTTGTTTCCAACCTTATAGCCTAAAGTGTTTCTCACACTTCCTCCCCCAGTAACT

GGCTCTATGGAATTTAGAGCGTCATAAAAAGCGTTCCTCATAGGAGCGTTAGCGTTGCTCGCTACAAAACTGGCA

AACCCTCTTTTTAAAAGATCGCTCTCATCATTCACTACTGCGCACAAATTAGGGTGGTTTTCTTTAAAATGATGA

GAGGGTTTTTTTAAAGCATAAAGGCTGTTGTCTTTGAGTTTGTAGGGCGCAGTGGTGTCATTAACAAGCTCGGCT

TTATAGTGCAAATGGGCATAATACAAAGGCATTCTCAAATAACGATCATTAAAATCCAATTCATCAAAGCCTATG

GCGTAATCAAAGAGGTTGAAATTAGGTGATTCGTTTTCACCGGTGTAAAACACTCGTTTAGTGTTTTGATAAGAT

AAAATCTTTCTAGCCGCTCCAAGAGGATTGCTAAAAACTAGATCTGAAAATTCATTGGGGTTTTGGTGGAGGGTG

ATTGCGTAGCGTTGGCTTAGGATAAAATAAAGAACGCTCTTTTTAAATTCTTTAATTTCTTCATCTCCCCACCAA

TTCGCCACAGCGATTTTTAGGGGGGGGGGGGGAGATTTAGAGGCCATTTTTTCAATGGAAGCGCTTTCTATAAAG

GCGTCTAATAGGGGTTGGAACATATGTATATCTCCTTCTTGAATTCTAAAAATTGATTGAATGTATGCAAATAAA

TGCATACACCATAGGTGTGGTTTAATTTGATGCCCTTTTTCAGGGCTGGAATGTGTAAGAGCGGGGTTATTTATG

CTGTTGTTTTTTGTTACTCGGGAAGGGCTTTACCTCTTCCGCATAAACGCTTCCATCAGCGTTTATAGTTAAAA

AAATCTTTCGGAACTGGTTTTGCGCTTACCCCAACCAACAGGGGATTTGCTGCTTTCCATTGAGCCTGTTTCTCT

GCGCGACGTTCGCGGCGGCGTGTTTGTGCATCCATCTGGATTCTCCTGTCAGTTAGCTTTGGTGGTGTGTGGCAG

TTGTAGTCCTGAACGAAAACCCCCCGCGATTGGCACATTGGCAGCTAATCCGGAATCGCACTTACGGCCAATGCT

TCGTTTCGTATCACACACCCCAAAGCCTTCTGCTTTGAATGCTGCCCTTCTTCAGGGCTTAATTTTTAAGAGCGT

CACCTTCATGGTGGTCAGTGCGTCCTGCTGATGTGCTCAGTATCACCGCCAGTGGTATTTATGTCAACACCGCCA

GAGATAATTTATCACCGCAGATGGTTATCTGTATGTTTTTTATATGAATTTATTTTTTGCAGGGGGGCATTGTTT
```

-continued

```
GGTAGGTGAGAGATCAATTCTGCATTAATGAATCGGCCAACGCGCGGGGAGAGGCGGTTTGCGTATTGGGCGCTC
TTCCGCTTCCTCGCTCACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGCATCACAAAAATCGACG
CTCAAGTCAGAGGTGGCGAAACCCGACAGGACTATAAAGATACCAGGCGTTTCCCCCTGGAAGCTCCCTCGTGCG
CTCTCCTGTTCCGACCCTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTGTGCACGAACCCCCCGT
TCAGCCCGACCGCTGCGCCTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTAAATTAAAAATGAAGTTTTAA
ATCAATCTAAAGTATATATGAGTAAACTTGGTCTGACAGTTACCAATGCTTAATCAGTGAGGCACCTATCTCAGC
GATCTGTCTATTTCGTTCATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTATCAGCAATAAACCAGCC
AGCCGGAAGGGCCGAGCGCAGAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCTACAGGCATCGTGGTGTCACG
CTCGTCGTTTGGTATGGCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACGGGATAATACCGCGCC
ACATAGCAGAACTTTAAAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTC
```

The sequence of *Bacteroides fragilis* NCTC 9343 wcfW CDS DNA is set for the below (SEQ ID NO: 4):

```
ATGATTGTATCATCTTTGCGAGGAGGATTGGGGAATCAAATGTTTATTTA
CGCTATGGTGAAGGCCATGGCATTAAGAAACAATGTACCATTCGCTTTTA
ATTTGACTACTGATTTTGCAAATGATGAAGTTTATAAAAGGAAACTTTTA
TTATCATATTTTGCATTAGACTTGCCTGAAAATAAAAAATTAACATTTGA
TTTTTCATATGGGAATTATTATAGAAGGCTAAGTCGTAATTTAGGTTGTC
ATATACTTCATCCATCATATCGTTATATTTGCGAAGAGCGCCCTCCCCAC
TTTGAATCAAGGTTAATTAGTTCTAAGATTACAAATGCTTTTCTGGAAGG
ATATTGGCAGTCAGAAAATATTTTCTTGATTATAAACAAGAGATAAAAG
AGGACTTTGTAATACAAAAAAAATTAGAATACACATCGTATTTGGAATTG
GAAGAAATAAAATTGCTAGATAAGAATGCCATAATGATTGGGGTTAGACG
GTATCAGGAAAGTGATGTAGCTCCTGGTGGAGTGTTAGAAGATGATTACT
ATAAATGTGCTATGGATATTATGGCATCAAAAGTTACTTCTCCTGTTTTC
TTTTGTTTTTCACAAGATTTAGAATGGGTTGAAAAACATCTAGCGGGAAA
ATATCCTGTTCGTTTGATAAGTAAAAAGGAGGATGATAGTGGTACTATAG
ATGATATGTTTCTAATGATGCATTTTCGTAATTATATAATATCGAATAGC
TCTTTTTACTGGTGGGAGCATGGCTTTCGAAATATGATGATAAGCTGGT
GATTGCTCCAGGTAATTTTATAAATAAGGATTCTGTACCAGAATCTTGGT
TTAAATTGAATGTAAGATAA
```

The sequence of pG171 is set forth below (SEQ ID NO: 5):

```
TCGCGCGTTTCGGTGATGACGGTGAAAACCTCTGACACATGCAGCTCCCGGAGACGGTCACAGCTTGTCTGTAAG
CGGATGCCGGGAGCAGACAAGCCCGTCAGGGCGCGTCAGCGGGTGTTGGCGGGTGTCGGGGCTGGCTTAACTATG
CGGCATCAGAGCAGATTGTACTGAGAGTGCACCATATATGCGGTGTGAAATACCGCACAGATGCGTAAGGAGAAA
ATACCGCATCAGGCGCCTCCTCAACCTGTATATTCGTAAACCACGCCCAATGGGAGCTGTCTCAGGTTTGTTCCT
GATTGGTTACGGCGCGTTTCGCATCATTGTTGAGTTTTTCCGCCAGCCCGACGCGCAGTTTACCGGTGCCTGGGT
GCAGTACATCAGCATGGGCAAATTCTTTCCATCCCGATGATTGTCGCGGGTGTGATCATGATGGTCTGGGCATA
TCGTCGCAGCCCACAGCAACACGTTTCCTGAGGAACCATGAAACAGTATTTAGAACTGATGCAAAAAGTGCTCGA
CGAAGGCACACAGAAAAACGACCGTACCGGAACCGGAACGCTTTCCATTTTTGGTCATCAGATGCGTTTTAACCT
GCAAGATGGATTCCCGCTGGTGACAACTAAACGTTGCCACCTGCGTTCCATCATCCATGAACTGCTGTGGTTTCT
GCAGGGCGACACTAACATTGCTTATCTACACGAAAACAATGTCACCATCTGGGACGAATGGGCCGATGAAAACGG
CGACCTCGGGCCAGTGTATGGTAAACAGTGGCGCGCCTGGCCAACGCCAGATGGTCGTCATATTGACCAGATCAC
TACGGTACTGAACCAGCTGAAAAACGACCCGGATTCGCGCCGCATTATTGTTTCAGCGTGGAACGTAGGCGAACT
GGATAAAATGGCGCTGGCACCGTGCCATGCATTCTTCCAGTTCTATGTGGCAGACGGCAAACTCTCTTGCCAGCT
TTATCAGCGCTCCTGTGACGTCTTCCTCGGCCTGCCGTTCAACATTGCCAGCTACGCGTTATTGGTGCATATGAT
GGCGCAGCAGTGCGATCTGGAAGTGGGTGATTTTGTCTGGACCGGTGGCGACACGCATCTGTACAGCAACCATAT
GGATCAAACTCATCTGCAATTAAGCCGCGAACCGCGTCCGCTGCCGAAGTTGATTATCAAACGTAAACCCGAATC
CATCTTCGACTACCGTTTCGAAGACTTTGAGATTGAAGGCTACGATCCGCATCCGGGCATTAAAGCGCCGGTGGC
TATCTAATTACGAAACATCCTGCCAGAGCCGACGCCAGTGTGCGTCGGTTTTTTTACCCTCCGTTAAATTCTTCG
AGACGCCTTCCCGAAGGCGCCATTCGCCATTCAGGCTGCGCAACTGTTGGGAAGGGCGATCGGTGCGGGCCTCTT
CGCTATTACGCCAGCTGGCGAAAGGGGGATGTGCTGCAAGGCGATTAAGTTGGGTAACGCCAGGGTTTTCCCAGT
CACGACGTTGTAAAACGACGGCCAGTGCCAAGCTTTCTTTAATGAAGCAGGGCATCAGGACGGTATCTTTGTGGA
GAAAGCAGAGTAATCTTATTCAGCCTGACTGGTGGGAAACCACCAGTCAGAATGTGTTAGCGCATGTTGACAAAA
ATACCATTAGTCACATTATCCGTCAGTCGGACGACATGGTAGATAACCTGTTTATTATGCGTTTTGATCTTACGT
TTAATATTACCTTTATGCGATGAAACGGTCTTGGCTTTGATATTCATTTGGTCAGAGATTTGAATGGTTCCCTGA
CCTGCCATCCACATTCGCAACATACTCGATTCGGTTCGGCTCAATGATAACGTCGGCATATTTAAAAACGAGGTT
ATCGTTGTCTCTTTTTTCAGAATATCGCCAAGGATATCGTCGAGAGATTCCGGTTTAATCGATTTAGAACTGATC
AATAAATTTTTTCTGACCAATAGATATTCATCAAAATGAACATTGGCAATTGCCATAAAAACGATAAATAACGTA
TTGGGATGTTGATTAATGATGAGCTTGATACGCTGACTGTTAGAAGCATCGTGGATGAAACAGTCCTCATTAATA
AACACCACTGAAGGGCGCTGTGAATCACAAGCTATGGCAAGGTCATCAACGGTTTCAATGTCGTTGATTTCTCTT
TTTTTAACCCCTCTACTCAACAGATACCCGGTTAAACCTAGTCGGGTGTAACTACATAAATCCATAATAATCGTT
GACATGGCATACCCTCACTCAATGCGTAACGATAATTCCCCTTACCTGAATATTTCATCATGACTAAACGGAACA
ACATGGGTCACCTAATGCGCCACTCTCGCGATTTTTCAGGCGGACTTACTATCCCGTAAAGTGTTGTATAATTTG
CCTGGAATTGTCTTAAAGTAAAGTAAATGTTGCGATATGTGAGTGAGCTTAAAACAAATATTTCGCTGCAGGAGT
ATCCTGGAAGATGTTCGTAGAAGCTTACTGCTCACAAGAAAAAAGGCACGTCATCTGACGTGCCTTTTTTATTTG
TACTACCCTGTACGATTACTGCAGCTCGAGTTTAATTCAAATCTTCTTCAGAAATCAATTTTTGTTCAGCGTTAT
ACTTTTGGGATTTTACCTCAAAATGGGATTCTATTTTCACCCACTCCTTACAAAGGATATTCTCATGCCCAAAAA
GCCAGTGTTTGGGGCCAATAATGATTTTTTCTGGATTTTCTATCAAATAGGCCGCCCACCAGCTATAAGTGCTAT
TAGCGATAATGCCATGCTGACAAGATTGCATGAGCAGCATGTCCCAATACGCCTCTTCTTCTTTATCCCTAGTGG
TCATGTCCATAAAAGGGTAGCCAAGATCAAGATTTTGCGTGAATTCTAAGTCTTCGCAAAACACAAAAAGCTCCA
TGTTTGGCACGCGCTTTGCCATATACTCAAGCGCCTTTTTTTGATAGTCAATACCAAGCTGACAGCCAATCCCCA
CATAATCCCCTCTTCTTATATGCACAAACACGCTGTTTTTAGCGGCTAAAATCAAAGAAAGCTTGCACTGATATT
```

```
CTTCCTCTTTTTTATTATTATTCTTATTATTTTCGGGTGGTGGTGGTAGAGTGAAGGTTTGCTTGATTAAAGGGG
ATATAGCATCAAAGTATCGTGGATCTTGGAAATAGCCAAAAAAATAAGTCAAGCGGCTTGGCTTTAGCAATTTAG
GCTCGTATTCAAAAACGATTTCTTGACTCACCCTATCAAATCCCATGCATTTGAGCGCGTCTCTTACTAGCTTGG
GGAGGTGTTGCATTTTAGCTATAGCGATTTCTTTCGCGCTCGCATAGGGCAAATCAATAGGGAAAAGTTCTAATT
GCATTTTCCTATCGCTCCAATCAAAAGAAGTGATATCTAACAGCACAGGCGTATTAGAGTGTTTTTGCAAACTTT
TAGCGAAAGCGTATTGAAACATTTGATTCCCAAGCCCTCCGCAAATTTGCACCACCTTAAAAGCCATATGTATAT
CTCCTTCTTGAATTCTAAAAATTGATTGAATGTATGCAAATAAATGCATACACCATAGGTGTGGTTTAATTTGAT
GCCCTTTTTCAGGGCTGGAATGTGTAAGAGCGGGGTTATTTATGCTGTTGTTTTTTTGTTACTCGGGAAGGGCTT
TACCTCTTCCGCATAAACGCTTCCATCAGCGTTTATAGTTAAAAAAATCTTTCGGAACTGGTTTTGCGCTTACCC
CAACCAACAGGGGATTTGCTGCTTTCCATTGAGCCTGTTTCTCTGCGCGACGTTCGCGGCGGCGTGTTTGTGCAT
CCATCTGGATTCTCCTGTCAGTTAGCTTTGGTGGTGTGTGGCAGTTGTAGTCCTGAACGAAAACCCCCCGCGATT
GGCACATTGGCAGCTAATCCGGAATCGCACTTACGGCCAATGCTTCGTTTCGTATCACACACCCCAAAGCCTTCT
GCTTTGAATGCTGCCCTTCTTCAGGGCTTAATTTTTAAGAGCGTCACCTTCATGGTGGTCAGTGCGTCCTGCTGA
TGTGCTCAGTATCACCGCCAGTGGTATTTATGTCAACACCGCCAGAGATAATTTATCACCGCAGATGGTTATCTG
TATGTTTTTTATATGAATTTATTTTTTGCAGGGGGGCATTGTTTGGTAGGTGAGAGATCAATTCTGCATTAATGA
ATCGGCCAACGCGCGGGGAGAGGCGGTTTGCGTATTGGGCGCTCTTCCGCTTCCTCGCTCACTGACTCGCTGCGC
TCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTT
TTCCATAGGCTCCGCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCTGCCGCTTACCGGA
TACCTGTCCGCCTTTCTCCCTTCGGGAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCCCGACCGCTGCGCCTTATCCGGTAAC
TATCGTCTTGAGTCCAACCCGGTAAGACACGACTTATCGCCACTGGCAGCAGCCACTGGTAACAGGATTAGCAGA
GCGAGGTATGTAGGCGGTGCTACAGAGTTCTTGAAGTGGTGGCCTAACTACGGCTACACTAGAAGGACAGTATTT
GGTATCTGCGCTCTGCTGAAGCCAGTTACCTTCGGAAAAAGAGTTGGTAGCTCTTGATCCGGCAAACAAACCACC
GCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAA
AGGATCTTCACCTAGATCCTTTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCAGTGCTGCAATGATACCGCGA
GACCCACGCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGTTAATAGT
TTGCGCAACGTTGTTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTCCTTCGGTCCTCCG
ATCGTTGTCAGAAGTAAGTTGGCCGCAGTGTTATCACTCATGGTTATGGCAGCACTGCATAATTCTCTTACTGTC
ATGCCATCCGTAAGATGCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTTTAAAAGTGCTCATCATT
GGAAAACGTTCTTCGGGGCGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAAACAGGAAGGCAAAATGCC
GCAAAAAAGGGAATAAGGGCGACACGGAAATGTTGAATACTCATACTCTTCCTTTTTCAATATTATTGAAGCATT
```

-continued

```
TATCAGGGTTATTGTCTCATGAGCGGATACATATTTGAATGTATTTAGAAAAATAAACAAATAGGGGTTCCGCGC

ACATTTCCCCGAAAAGTGCCACCTGACGTCTAAGAAACCATTATTATCATGACATTAACCTATAAAAATAGGCGT

ATCACGAGGCCCTTTCGTC
```

The sequence of pG180 is set forth below (SEQ ID NO: 6):

```
TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGCTGGCTTAACTATG

CGGCATCAGAGCAGATTGTACTGAGAGTGCACCATATATGCGGTGTGAAATACCGCACAGATGCGTAAGGAGAAA

ATACCGCATCAGGCGCCTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTTTACCGGTGCCTGGGT

GCAGTACATCAGCATGGGCAAATTCTTTCCATCCCGATGATTGTCGCGGGTGTGATCATGATGGTCTGGGCATA

TCGTCGCAGCCCACAGCAACACGTTTCCTGAGGAACCATGAAACAGTATTTAGAACTGATGCAAAAAGTGCTCGA

CGAAGGCACACAGAAAAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGAACTGCTGTGGTTTCT

GCAGGGCGACACTAACATTGCTTATCTACACGAAAACAATGTCACCATCTGGGACGAATGGGCCGATGAAAACGG

CGACCTCGGGCCAGTGTATGGTAAACAGTGGCGCGCCTGGCCAACGCCAGATGGTCGTCATATTGACCAGATCAC

TACGGTACTGAACCAGCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAAACTCTCTTGCCAGCT

TTATCAGCGCTCCTGTGACGTCTTCCTCGGCCTGCCGTTCAACATTGCCAGCTACGCGTTATTGGTGCATATGAT

GGCGCAGCAGTGCGATCTGGAAGTGGGTGATTTTGTCTGGACCGGTGGCGACACGCATCTGTACAGCAACCATAT

GGATCAAACTCATCTGCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCATTAAAGCGCCGGTGGC

TATCTAATTACGAAACATCCTGCCAGAGCCGACGCCAGTGTGCGTCGGTTTTTTTACCCTCCGTTAAATTCTTCG

AGACGCCTTCCCGAAGGCGCCATTCGCCATTCAGGCTGCGCAACTGTTGGGAAGGGCGATCGGTGCGGGCCTCTT

CGCTATTACGCCAGCTGGCGAAAGGGGATGTGCTGCAAGGCGATTAAGTTGGGTAACGCCAGGGTTTTCCCAGT

CACGACGTTGTAAAACGACGGCCAGTGCCAAGCTTTCTTTAATGAAGCAGGGCATCAGGACGGTATCTTTGTGGA

GAAAGCAGAGTAATCTTATTCAGCCTGACTGGTGGGAAACCACCAGTCAGAATGTGTTAGCGCATGTTGACAAAA

ATACCATTAGTCACATTATCCGTCAGTCGGACGACATGGTAGATAACCTGTTTATTATGCGTTTTGATCTTACGT

TTAATATTACCTTTATGCGATGAAACGGTCTTGGCTTTGATATTCATTTGGTCAGAGATTTGAATGGTTCCCTGA

CCTGCCATCCACATTCGCAACATACTCGATTCGGTTCGGCTCAATGATAACGTCGGCATATTTAAAAACGAGGTT

ATCGTTGTCTCTTTTTTCAGAATATCGCCAAGGATATCGTCGAGAGATTCCGGTTTAATCGATTTAGAACTGATC

AATAAATTTTTTCTGACCAATAGATATTCATCAAAATGAACATTGGCAATTGCCATAAAAACGATAAATAACGTA

TTGGGATGTTGATTAATGATGAGCTTGATACGCTGACTGTTAGAAGCATCGTGGATGAAACAGTCCTCATTAATA

AACACCACTGAAGGGCGCTGTGAATCACAAGCTATGGCAAGGTCATCAACGGTTTCAATGTCGTTGATTTCTCTT

TTTTTAACCCCTCTACTCAACAGATACCCGGTTAAACCTAGTCGGGTGTAACTACATAAATCCATAATAATCGTT

GACATGGCATACCCTCACTCAATGCGTAACGATAATTCCCCTTACCTGAATATTTCATCATGACTAAACGGAACA

ACATGGGTCACCTAATGCGCCACTCTCGCGATTTTTCAGGCGGACTTACTATCCCGTAAAGTGTTGTATAATTTG

CCTGGAATTGTCTTAAAGTAAAGTAAATGTTGCGATATGTGAGTGAGCTTAAAACAAATATTTCGCTGCAGGAGT

ATCCTGGAAGATGTTCGTAGAAGCTTACTGCTCACAAGAAAAAAGGCACGTCATCTGACGTGCCTTTTTTATTTG

TACTACCCTGTACGATTACTGCAGCTCGAGTTTAATTCAAATCTTCTTCAGAAATCAATTTTTGTTCTCTTACAT
```

```
TCAATTTAAACCAAGATTCTGGTACAGAATCCTTATTTATAAAATTACCTGGAGCAATCACCAGCTTATCATCAT

ATTTCGAAAGCCATGCTCCCCACCAGTAAAAAGAGCTATTCGATATTATATAATTACGAAAATGCATCATTAGAA

ACATATCATCTATAGTACCACTATCATCCTCCTTTTTACTTATCAAACGAACAGGATATTTTCCCGCTAGATGTT

TTTCAACCCATTCTAAATCTTGTGAAAAACAAAAGAAAACAGGAGAAGTAACTTTTGATGCCATAATATCCATAG

CACATTTATAGTAATCATCTTCTAACACTCCACCAGGAGCTACATCACTTTCCTGATACCGTCTAACCCCAATCA

TTATGGCATTCTTATCTAGCAATTTTATTTCTTCCAATTCCAAATACGATGTGTATTCTAATTTTTTTGTATTA

CAAAGTCCTCTTTTATCTCTTGTTTATAATCAAGAAAATATTTTTCTGACTGCCAATATCCTTCCAGAAAAGCAT

TTGTAATCTTAGAACTAATTAACCTTGATTCAAAGTGGGGAGGGCGCTCTTCGCAAATATAACGATATGATGGAT

GAAGTATATGACAACCTAAATTACGACTTAGCCTTCTATAATAATTCCCATATGAAAAATCAAATGTTAATTTTT

TATTTTCAGGCAAGTCTAATGCAAAATATGATAATAAAAGTTTCCTTTTATAAACTTCATCATTTGCAAATCAG

TAGTCAAATTAAAAGCGAATGGTACATTGTTTCTTAATGCCATGGCCTTCACCATAGCGTAAATAAACATTTGAT

TCCCCAATCCTCCTCGCAAAGATGATACAATCATATGTATATCTCCTTCTTGTCTAGAATTCTAAAAATTGATTG

AATGTATGCAAATAAATGCATACACCATAGGTGTGGTTTAATTTGATGCCCTTTTTCAGGGCTGGAATGTGTAAG

AGCGGGGTTATTTATGCTGTTGTTTTTTGTTACTCGGGAAGGGCTTTACCTCTTCCGCATAAACGCTTCCATCA

GCGTTTATAGTTAAAAAAATCTTTCGGAACTGGTTTTGCGCTTACCCCAACCAACAGGGGATTTGCTGCTTTCCA

TTGAGCCTGTTTCTCTGCGCGACGTTCGCGGCGGCGTGTTTGTGCATCCATCTGGATTCTCCTGTCAGTTAGCTT

TGGTGGTGTGTGGCAGTTGTAGTCCTGAACGAAAACCCCCGCGATTGGCACATTGGCAGCTAATCCGGAATCGC

ACTTACGGCCAATGCTTCGTTTCGTATCACACACCCCAAAGCCTTCTGCTTTGAATGCTGCCCTTCTTCAGGGCT

TAATTTTTAAGAGCGTCACCTTCATGGTGGTCAGTGCGTCCTGCTGATGTGCTCAGTATCACCGCCAGTGGTATT

TATGTCAACACCGCCAGAGATAATTTATCACCGCAGATGGTTATCTGTATGTTTTTTATATGAATTTATTTTTG

CAGGGGGGCATTGTTTGGTAGGTGAGAGATCAATTCTGCATTAATGAATCGGCCAACGCGCGGGGAGAGGCGGTT

TGCGTATTGGGCGCTCTTCCGCTTCCTCGCTCACTGACTCGCTGCGCTCGGTCGTTCGGCTGCGGCGAGCGGTAT

CAGCTCACTCAAAGGCGGTAATACGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTCCATAGGCTCCGCCCCCCTGACGAGC

ATCACAAAAATCGACGCTCAAGTCAGAGGTGGCGAAACCCGACAGGACTATAAAGATACCAGGCGTTTCCCCCTG

GAAGCTCCCTCGTGCGCTCTCCTGTTCCGACCCTGCCGCTTACCGGATACCTGTCCGCCTTTCTCCCTTCGGGAA

GCGTGGCGCTTTCTCATAGCTCACGCTGTAGGTATCTCAGTTCGGTGTAGGTCGTTCGCTCCAAGCTGGGCTGTG

TGCACGAACCCCCCGTTCAGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTATGTAGGCGGTGCTACAGAGT

TCTTGAAGTGGTGGCCTAACTACGGCTACACTAGAAGGACAGTATTTGGTATCTGCGCTCTGCTGAAGCCAGTTA

CCTTCGGAAAAAGAGTTGGTAGCTCTTGATCCGGCAAACAAACCACCGCTGGTAGCGGTGGTTTTTTTGTTTGCA

AGCAGCAGATTACGCGCAGAAAAAAAGGATCTCAAGAAGATCCTTTGATCTTTTCTACGGGGTCTGACGCTCAGT

GGAACGAAAACTCACGTTAAGGGATTTTGGTCATGAGATTATCAAAAAGGATCTTCACCTAGATCCTTTTAAATT

AAAAATGAAGTTTTAAATCAATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCCGTCGTGTAGATAACTACGA

TACGGGAGGGCTTACCATCTGGCCCCAGTGCTGCAATGATACCGCGAGACCCACGCTCACCGGCTCCAGATTTAT

CAGCAATAAACCAGCCAGCCGGAAGGGCCGAGCGCAGAAGTGGTCCTGCAACTTTATCCGCCTCCATCCAGTCTA

TTAATTGTTGCCGGGAAGCTAGAGTAAGTAGTTCGCCAGTTAATAGTTTGCGCAACGTTGTTGCCATTGCTACAG

GCATCGTGGTGTCACGCTCGTCGTTTGGTATGGCTTCATTCAGCTCCGGTTCCCAACGATCAAGGCGAGTTACAT

GATCCCCCATGTTGTGCAAAAAAGCGGTTAGCTCCTTCGGTCCTCCGATCGTTGTCAGAAGTAAGTTGGCCGCAG
```

-continued

```
TGTTATCACTCATGGTTATGGCAGCACTGCATAATTCTCTTACTGTCATGCCATCCGTAAGATGCTTTTCTGTGA

CTGGTGAGTACTCAACCAAGTCATTCTGAGAATAGTGTATGCGGCGACCGAGTTGCTCTTGCCCGGCGTCAATAC

GGGATAATACCGCGCCACATAGCAGAACTTTAAAAGTGCTCATCATTGGAAAACGTTCTTCGGGGCGAAAACTCT

CAAGGATCTTACCGCTGTTGAGATCCAGTTCGATGTAACCCACTCGTGCACCCAACTGATCTTCAGCATCTTTTA

CTTTCACCAGCGTTTCTGGGTGAGCAAAAACAGGAAGGCAAAATGCCGCAAAAAAGGGAATAAGGGCGACACGGA

AATGTTGAATACTCATACTCTTCCTTTTTCAATATTATTGAAGCATTTATCAGGGTTATTGTCTCATGAGCGGAT

ACATATTTGAATGTATTTAGAAAAATAAACAAATAGGGGTTCCGCGCACATTTCCCCGAAAAGTGCCACCTGACG

TCTAAGAAACCATTATTATCATGACATTAACCTATAAAAATAGGCGTATCACGAGGCCCTTTCGTC
```

The sequence of W3110 deltalon::Kan::lacZwithRBS *Escherichia coli* str. K-12 substr. W3110 is set forth below (SEQ ID NO: 7):

```
GTCCATGGAAGACGTCGAAAAAGTGGTTATCGACGAGTCGGTAATTGATGGTCAAAGCAAACCGTTGCTGATTTA

TGGCAAGCCGGAAGCGCAACAGGCATCTGGTGAATAATTAACCATTCCCATACAATTAGTTAACCAAAAAGGGGG

GATTTTATCTCCCCTTTAATTTTTCCTCTATTCTCGGCGTTGAATGTGGGGGAAACATCCCCATATACTGACGTA

CATGTTAATAGATGGCGTGAAGCACAGTCGTGTCATCTGATTACCTGGCGGAAATTAAACTAAGAGAGAGCTCTA

TGATTCCGGGGATCCGTCGACCTGCAGTTCGAAGTTCCTATTCTCTAGAAAGTATAGGAACTTCAGAGCGCTTTT

GAAGCTCACGCTGCCGCAAGCACTCAGGGCGCAAGGGCTGCTAAAGGAAGCGGAACACGTAGAAAGCCAGTCCGC

AGAAACGGTGCTGACCCCGGATGAATGTCAGCTACTGGGCTATCTGGACAAGGGAAAACGCAAGCGCAAAGAGAA

AGCAGGTAGCTTGCAGTGGGCTTACATGGCGATAGCTAGACTGGGCGGTTTTATGGACAGCAAGCGAACCGGAAT

TGCCAGCTGGGGCGCCCTCTGGTAAGGTTGGGAAGCCCTGCAAAGTAAACTGGATGGCTTTCTTGCCGCCAAGGA

TCTGATGGCGCAGGGGATCAAGATCTGATCAAGAGACAGGATGAGGATCGTTTCGCATGATTGAACAAGATGGAT

TGCACGCAGGTTCTCCGGCCGCTTGGGTGGAGAGGCTATTCGGCTATGACTGGGCACAACAGACAATCGGCTGCT

CTGATGCCGCCGTGTTCCGGCTGTCAGCGCAGGGGCGCCCGGTTCTTTTTGTCAAGACCGACCTGTCCGGTGCCC

TGAATGAACTGCAGGACGAGGCAGCGCGGCTATCGTGGCTGGCCACGACGGGCGTTCCTTGCGCAGCTGTGCTCG

ACGTTGTCACTGAAGCGGGAAGGGACTGGCTGCTATTGGGCGAAGTGCCGGGGCAGGATCTCCTGTCATCTCACC

TTGCTCCTGCCGAGAAAGTATCCATCATGGCTGATGCAATGCGGCGGCTGCATACGCTTGATCCGGCTACCTGCC

CATTCGACCACCAAGCGAAACATCGCATCGAGCGAGCACGTACTCGGATGGAAGCCGGTCTTGTCGATCAGGATG

ATCTGGACGAAGAGCATCAGGGGCTCGCGCCAGCCGAACTGTTCGCCAGGCTCAAGGCGCGCATGCCCGACGGCG

AGGATCTCGTCGTGACCCATGGCGATGCCTGCTTGCCGAATATCATGGTGGAAAATGGCCGCTTTTCTGGATTCA

TCGACTGTGGCCGGCTGGGTGTGGCGGACCGCTATCAGGACATAGCGTTGGCTACCCGTGATATTGCTGAAGAGC

TTGGCGGCGAATGGGCTGACCGCTTCCTCGTGCTTTACGGTATCGCCGCTCCCGATTCGCAGCGCATCGCCTTCT

ATCGCCTTCTTGACGAGTTCTTCTAATAAGGGGATCTTGAAGTTCCTATTCCGAAGTTCCTATTCTCTAGAAAGT

ATAGGAACTTCGAAGCAGCTCCAGCCTACATAAAGCGGCCGCTTATTTTTGACACCAGACCAACTGGTAATGGTA

GCGACCGGCGCTCAGCTGGAATTCCGCCGATACTGACGGGCTCCAGGAGTCGTCGCCACCAATCCCCATATGGAA

ACCGTCGATATTCAGCCATGTGCCTTCTTCCGCGTGCAGCAGATGGCGATGGCTGGTTTCCATCAGTTGCTGTTG

ACTGTAGCGGCTGATGTTGAACTGGAAGTCGCCGCGCCACTGGTGTGGGCCATAATTCAATTCGCGCGTCCCGCA

GCGCAGACCGTTTTCGCTCGGGAAGACGTACGGGGTATACATGTCTGACAATGGCAGATCCCAGCGGTCAAAACA

GGCGGCAGTAAGGCGGTCGGGATAGTTTTCTTGCGGCCCTAATCCGAGCCAGTTTACCCGCTCTGCTACCTGCGC

CAGCTGGCAGTTCAGGCCAATCCGCGCCGGATGCGGTGTATCGCTCGCCACTTCAACATCAACGGTAATCGCCAT

TTGACCACTACCATCAATCCGGTAGGTTTTCCGGCTGATAAATAAGGTTTTCCCCTGATGCTGCCACGCGTGAGC
```

-continued
GGTCGTAATCAGCACCGCATCAGCAAGTGTATCTGCCGTGCACTGCAACAACGCTGCTTCGGCCTGGTAATGGCC

CGCCGCCTTCCAGCGTTCGACCCAGGCGTTAGGGTCAATGCGGGTCGCTTCACTTACGCCAATGTCGTTATCCAG

CGGTGCACGGGTGAACTGATCGCGCAGCGGCGTCAGCAGTTGTTTTTTATCGCCAATCCACATCTGTGAAAGAAA

GCCTGACTGGCGGTTAAATTGCCAACGCTTATTACCCAGCTCGATGCAAAAATCCATTTCGCTGGTGGTCAGATG

CGGGATGGCGTGGGACGCGGCGGGGAGCGTCACACTGAGGTTTTCCGCCAGACGCCACTGCTGCCAGGCGCTGAT

GTGCCCGGCTTCTGACCATGCGGTCGCGTTCGGTTGCACTACGCGTACTGTGAGCCAGAGTTGCCCGGCGCTCTC

CGGCTGCGGTAGTTCAGGCAGTTCAATCAACTGTTTACCTTGTGGAGCGACATCCAGAGGCACTTCACCGCTTGC

CAGCGGCTTACCATCCAGCGCCACCATCCAGTGCAGGAGCTCGTTATCGCTATGACGGAACAGGTATTCGCTGGT

CACTTCGATGGTTTGCCCGGATAAACGGAACTGGAAAAACTGCTGCTGGTGTTTTGCTTCCGTCAGCGCTGGATG

CGGCGTGCGGTCGGCAAAGACCAGACCGTTCATACAGAACTGGCGATCGTTCGGCGTATCGCCAAAATCACCGCC

GTAAGCCGACCACGGGTTGCCGTTTTCATCATATTTAATCAGCGACTGATCCACCCAGTCCCAGACGAAGCCGCC

CTGTAAACGGGGATACTGACGAAACGCCTGCCAGTATTTAGCGAAACCGCCAAGACTGTTACCCATCGCGTGGGC

GTATTCGCAAAGGATCAGCGGGCGCGTCTCTCCAGGTAGCGAAAGCCATTTTTTGATGGACCATTTCGGCACAGC

CGGGAAGGGCTGGTCTTCATCCACGCGCGCGTACATCGGGCAAATAATATCGGTGGCCGTGGTGTCGGCTCCGCC

GCCTTCATACTGCACCGGGCGGGAAGGATCGACAGATTTGATCCAGCGATACAGCGCGTCGTGATTAGCGCCGTG

GCCTGATTCATTCCCCAGCGACCAGATGATCACACTCGGGTGATTACGATCGCGCTGCACCATTCGCGTTACGCG

TTCGCTCATCGCCGGTAGCCAGCGCGGATCATCGGTCAGACGATTCATTGGCACCATGCCGTGGGTTTCAATATT

GGCTTCATCCACCACATACAGGCCGTAGCGGTCGCACAGCGTGTACCACAGCGGATGGTTCGGATAATGCGAACA

GCGCACGGCGTTAAAGTTGTTCTGCTTCATCAGCAGGATATCCTGCACCATCGTCTGCTCATCCATGACCTGACC

ATGCAGAGGATGATGCTCGTGACGGTTAACGCCTCGAATCAGCAACGGCTTGCCGTTCAGCAGCAGCAGACCATT

TTCAATCCGCACCTCGCGGAAACCGACATCGCAGGCTTCTGCTTCAATCAGCGTGCCGTCGGCGGTGTGCAGTTC

AACCACCGCACGATAGAGATTCGGGATTTCGGCGCTCCACAGTTTCGGGTTTTCGACGTTCAGACGTAGTGTGAC

GCGATCGGCATAACCACCACGCTCATCGATAATTTCACCGCCGAAAGGCGCGGTGCCGCTGGCGACCTGCGTTTC

ACCCTGCCATAAAGAAACTGTTACCCGTAGGTAGTCACGCAACTCGCCGCACATCTGAACTTCAGCCTCCAGTAC

AGCGCGGCTGAAATCATCATTAAAGCGAGTGGCAACATGGAAATCGCTGATTTGTGTAGTCGGTTTATGCAGCAA

CGAGACGTCACGGAAAATGCCGCTCATCCGCCACATATCCTGATCTTCCAGATAACTGCCGTCACTCCAGCGCAG

CACCATCACCGCGAGGCGGTTTTCTCCGGCGCGTAAAAATGCGCTCAGGTCAAATTCAGACGGCAAACGACTGTC

CTGGCCGTAACCGACCCAGCGCCCGTTGCACCACAGATGAAACGCCGAGTTAACGCCATCAAAAATAATTCGCGT

CTGGCCTTCCTGTAGCCAGCTTTCATCAACATTAAATGTGAGCGAGTAACAACCCGTCGGATTCTCCGTGGGAAC

AAACGGCGGATTGACCGTAATGGGATAGGTCACGTTGGTGTAGATGGGCGCATCGTAACCGTGCATCTGCCAGTT

TGAGGGGACGACGACAGTATCGGCCTCAGGAAGATCGCACTCCAGCCAGCTTTCCGGCACCGCTTCTGGTGCCGG

AAACCAGGCAAAGCGCCATTCGCCATTCAGGCTGCGCAACTGTTGGGAAGGGCGATCGGTGCGGGCCTCTTCGCT

ATTACGCCAGCTGGCGAAAGGGGGATGTGCTGCAAGGCGATTAAGTTGGGTAACGCCAGGGTTTTCCCAGTCACG

ACGTTGTAAAACGACGGCCAGTGAATCCGTAATCATGGTCATAGTAGGTTTCCTCAGGTTGTGACTGCAAAATAG

TGACCTCGCGCAAAATGCACTAATAAAAACAGGGCTGGCAGGCTAATTCGGGCTTGCCAGCCTTTTTTTGTCTCG

CTAAGTTAGATGGCGGATCGGGCTTGCCCTTATTAAGGGGTGTTGTAAGGGGATGGCTGGCCTGATATAACTGCT

-continued

```
GCGCGTTCGTACCTTGAAGGATTCAAGTGCGATATAAATTATAAAGAGGAAGAGAAGAGTGAATAAATCTCAATT

GATCGACAAGATTGCTGCAGGGGCTGATATCTCTAAAGCTGCGGCTGGCCGTGCGTTAGATGCTATTATTGCTTC

CGTAACTGAATCTCTGAAAGAAGG
```

The sequence of pG186 is set forth below (SEQ ID NO: 8):

```
TCGCGCGTTTCGGTGATGACGGTGAAAACCTCTGACACATGCAGCTCCCGGAGACGGTCACAGCTTGTCTGTAAG

CGGATGCCGGGAGCAGACAAGCCCGTCAGGGCGCGTCAGCGGGTGTTGGCGGGTGTCGGGGCTGGCTTAACTATG

CGGCATCAGAGCAGATTGTACTGAGAGTGCACCATATATGCGGTGTGAAATACCGCACAGATGCGTAAGGAGAAA

ATACCGCATCAGGCGCCTCCTCAACCTGTATATTCGTAAACCACGCCCAATGGGAGCTGTCTCAGGTTTGTTCCT

GATTGGTTACGGCGCGTTTCGCATCATTGTTGAGTTTTTCCGCCAGCCCGACGCGCAGTTTACCGGTGCCTGGGT

GCAGTACATCAGCATGGGCAAATTCTTTCCATCCCGATGATTGTCGCGGGTGTGATCATGATGGTCTGGGCATA

TCGTCGCAGCCCACAGCAACACGTTTCCTGAGGAACCATGAAACAGTATTTAGAACTGATGCAAAAAGTGCTCGA

CGAAGGCACACAGAAAAACGACCGTACCGGAACCGGAACGCTTTCCATTTTTGGTCATCAGATGCGTTTTAACCT

GCAAGATGGATTCCCGCTGGTGACAACTAAACGTTGCCACCTGCGTTCCATCATCCATGAACTGCTGTGGTTTCT

GCAGGGCGACACTAACATTGCTTATCTACACGAAAACAATGTCACCATCTGGGACGAATGGGCCGATGAAAACGG

CGACCTCGGGCCAGTGTATGGTAAACAGTGGCGCGCCTGGCCAACGCCAGATGGTCGTCATATTGACCAGATCAC

TACGGTACTGAACCAGCTGAAAAACGACCCGGATTCGCGCCGCATTATTGTTTCAGCGTGGAACGTAGGCGAACT

GGATAAAATGGCGCTGGCACCGTGCCATGCATTCTTCCAGTTCTATGTGGCAGACGGCAAACTCTCTTGCCAGCT

TTATCAGCGCTCCTGTGACGTCTTCCTCGGCCTGCCGTTCAACATTGCCAGCTACGCGTTATTGGTGCATATGAT

GGCGCAGCAGTGCGATCTGGAAGTGGGTGATTTTGTCTGGACCGGTGGCGACACGCATCTGTACAGCAACCATAT

GGATCAAACTCATCTGCAATTAAGCCGCGAACCGCGTCCGCTGCCGAAGTTGATTATCAAACGTAAACCCGAATC

CATCTTCGACTACCGTTTCGAAGACTTTGAGATTGAAGGCTACGATCCGCATCCGGGCATTAAAGCGCCGGTGGC

TATCTAATTACGAAACATCCTGCCAGAGCCGACGCCAGTGTGCGTCGGTTTTTTTACCCTCCGTTAAATTCTTCG

AGACGCCTTCCCGAAGGCGCCATTCGCCATTCAGGCTGCGCAACTGTTGGGAAGGGCGATCGGTGCGGGCCTCTT

CGCTATTACGCCAGCTGGCGAAAGGGGGATGTGCTGCAAGGCGATTAAGTTGGGTAACGCCAGGGTTTTCCCAGT

CACGACGTTGTAAAACGACGGCCAGTGCCAAGCTTTCTTTAATGAAGCAGGGCATCAGGACGGTATCTTTGTGGA

GAAAGCAGAGTAATCTTATTCAGCCTGACTGGTGGGAAACCACCAGTCAGAATGTGTTAGCGCATGTTGACAAAA

ATACCATTAGTCACATTATCCGTCAGTCGGACGACATGGTAGATAACCTGTTTATTATGCGTTTTGATCTTACGT

TTAATATTACCTTTATGCGATGAAACGGTCTTGGCTTTGATATTCATTTGGTCAGAGATTTGAATGGTTCCCTGA

CCTGCCATCCACATTCGCAACATACTCGATTCGGTTCGGCTCAATGATAACGTCGGCATATTTAAAAACGAGGTT

ATCGTTGTCTCTTTTTTCAGAATATCGCCAAGGATATCGTCGAGAGATTCCGGTTTAATCGATTTAGAACTGATC

AATAAATTTTTTCTGACCAATAGATATTCATCAAAATGAACATTGGCAATTGCCATAAAAACGATAAATAACGTA

TTGGGATGTTGATTAATGATGAGCTTGATACGCTGACTGTTAGAAGCATCGTGGATGAAACAGTCCTCATTAATA

AACACCACTGAAGGGCGCTGTGAATCACAAGCTATGGCAAGGTCATCAACGGTTTCAATGTCGTTGATTTCTCTT

TTTTTAACCCCTCTACTCAACAGATACCCGGTTAAACCTAGTCGGGTGTAACTACATAAATCCATAATAATCGTT

GACATGGCATACCCTCACTCAATGCGTAACGATAATTCCCCTTACCTGAATATTTCATCATGACTAAACGGAACA

ACATGGGTCACCTAATGCGCCACTCTCGCGATTTTTCAGGCGGACTTACTATCCCGTAAAGTGTTGTATAATTTG

CCTGGAATTGTCTTAAAGTAAAGTAAATGTTGCGATATGTGAGTGAGCTTAAAACAAATATTTCGCTGCAGGAGT

ATCCTGGAAGATGTTCGTAGAAGCTTACTGCTCACAAGAAAAAAGGCACGTCATCTGACGTGCCTTTTTTATTTG

TACTACCCTGTACGATTACTGCAGCTCGAGTTAGTCTTTATCTGCCGGACTTAAGGTCACTGAAGAGAGATAATT
```

-continued

```
CAGCAGGGCGATATCGTTCTCGACACCCAGCTTCATCATCGCAGATTTCTTCTGGCTACTGATGGTTTTAATACT

GCGGTTCAGCTTTTTAGCGATCTCGGTCACCAGGAAGCCTTCCGCAAACAGGCGCAGAACTTCACTCTCTTTTGG

CGAGAGACGCTTGTCACCGTAACCACCAGCACTGATTTTTTCCAACAGGCGAGAAACGCTTTCCGGGGTAAATTT

CTTCCCTTTCTGCAGCGCGGCGAGAGCTTTCGGCAGATCGGTCGGTGCACCTTGTTTCAGCACGATCCCTTCGAT

ATCCAGATCCAATACCGCACTAAGAATCGCCGGGTTGTTGTTCATAGTCAGAACAATGATCGACAGGCTTGGGAA

ATGGCGCTTGATGTACTTGATTAAGGTAATGCCATCGCCGTACTTATCGCCAGGCATGGAGAGATCGGTAATCAA

CACATGCGCATCCAGTTTCGGCAGGTTGTTGATCAGTGCTGTAGAGTCTTCAAATTCGCCGACAACATTCACCCA

CTCAATTTGCTCAAGTGATTTGCGAATACCGAACAAGACTATCGGATGGTCATCGGCAATAATTACGTTCATATT

GTTCATTGTATATCTCCTTCTTCTCGAGTTTAATTCAAATCTTCTTCAGAAATCAATTTTTGTTCAGCGTTATAC

TTTTGGGATTTTACCTCAAAATGGGATTCTATTTTCACCCACTCCTTACAAAGGATATTCTCATGCCCAAAAAGC

CAGTGTTTGGGGCCAATAATGATTTTTTCTGGATTTTCTATCAAATAGGCCGCCCACCAGCTATAAGTGCTATTA

GCGATAATGCCATGCTGACAAGATTGCATGAGCAGCATGTCCCAATACGCCTCTTCTTCTTTATCCCTAGTGGTC

ATGTCCATAAAAGGGTAGCCAAGATCAAGATTTTGCGTGAATTCTAAGTCTTCGCAAAACACAAAAAGCTCCATG

TTTGGCACGCGCTTTGCCATATACTCAAGCGCCTTTTTTTGATAGTCAATACCAAGCTGACAGCCAATCCCCACA

TAATCCCCTCTTCTTATATGCACAAACACGCTGTTTTTAGCGGCTAAAATCAAAGAAAGCTTGCACTGATATTCT

TCCTCTTTTTATTATTATTCTTATTATTTTCGGGTGGTGGTGGTAGAGTGAAGGTTTGCTTGATTAAAGGGGAT

ATAGCATCAAAGTATCGTGGATCTTGGAAATAGCCAAAAAAATAAGTCAAGCGGCTTGGCTTTAGCAATTTAGGC

TCGTATTCAAAAACGATTTCTTGACTCACCCTATCAAATCCCATGCATTTGAGCGCGTCTCTTACTAGCTTGGGG

AGGTGTTGCATTTTAGCTATAGCGATTTCTTTCGCGCTCGCATAGGGCAAATCAATAGGGAAAAGTTCTAATTGC

ATTTTCCTATCGCTCCAATCAAAAGAAGTGATATCTAACAGCACAGGCGTATTAGAGTGTTTTTGCAAACTTTTA

GCGAAAGCGTATTGAAACATTTGATTCCCAAGCCCTCCGCAAATTTGCACCACCTTAAAAGCCATATGTATATCT

CCTTCTTGAATTCTAAAAATTGATTGAATGTATGCAAATAAATGCATACACCATAGGTGTGGTTTAATTTGATGC

CCTTTTTCAGGGCTGGAATGTGTAAGAGCGGGGTTATTTATGCTGTTGTTTTTTGTTACTCGGGAAGGGCTTTA

CCTCTTCCGCATAAACGCTTCCATCAGCGTTTATAGTTAAAAAAATCTTTCGGAACTGGTTTTGCGCTTACCCCA

ACCAACAGGGGATTTGCTGCTTTCCATTGAGCCTGTTTCTCTGCGCGACGTTCGCGGCGGCGTGTTTGTGCATCC

ATCTGGATTCTCCTGTCAGTTAGCTTTGGTGGTGTGTGGCAGTTGTAGTCCTGAACGAAAACCCCCCGCGATTGG

CACATTGGCAGCTAATCCGGAATCGCACTTACGGCCAATGCTTCGTTTCGTATCACACACCCCAAAGCCTTCTGC

TTTGAATGCTGCCCTTCTTCAGGGCTTAATTTTTAAGAGCGTCACCTTCATGGTGGTCAGTGCGTCCTGCTGATG

TGCTCAGTATCACCGCCAGTGGTATTTATGTCAACACCGCCAGAGATAATTTATCACCGCAGATGGTTATCTGTA

TGTTTTTTATATGAATTTATTTTTTGCAGGGGGGCATTGTTTGGTAGGTGAGAGATCAATTCTGCATTAATGAAT

CGGCCAACGCGCGGGAGAGGCGGTTTGCGTATTGGGCGCTCTTCCGCTTCCTCGCTCACTGACTCGCTGCGCTC

GGTCGTTCGGCTGCGGCGAGCGGTATCAGCTCACTCAAAGGCGGTAATACGGTTATCCACAGAATCAGGGGATAA

CGCAGGAAAGAACATGTGAGCAAAAGGCCAGCAAAAGGCCAGGAACCGTAAAAAGGCCGCGTTGCTGGCGTTTTT

CCATAGGCTCCGCCCCCCTGACGAGCATCACAAAAATCGACGCTCAAGTCAGAGGTGGCGAAACCCGACAGGACT

ATAAAGATACCAGGCGTTTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGGTATCTCAGTTCGGTGTA

GGTCGTTCGCTCCAAGCTGGGCTGTGTGCACGAACCCCCCGTTCAGCCCGACCGCTGCGCCTTATCCGGTAACTA

TCGTCTTGAGTCCAACCCGGTAAGACACGACTTATCGCCACTGGCAGCAGCCACTGGTAACAGGATTAGCAGAGC

GAGGTATGTAGGCGGTGCTACAGAGTTCTTGAAGTGGTGGCCTAACTACGGCTACACTAGAAGGACAGTATTTGG

TATCTGCGCTCTGCTGAAGCCAGTTACCTTCGGAAAAAGAGTTGGTAGCTCTTGATCCGGCAAACAAACCACCGC
```

-continued

```
TGGTAGCGGTGGTTTTTTTGTTTGCAAGCAGCAGATTACGCGCAGAAAAAAAGGATCTCAAGAAGATCCTTTGAT

CTTTTCTACGGGGTCTGACGCTCAGTGGAACGAAAACTCACGTTAAGGGATTTTGGTCATGAGATTATCAAAAAG

GATCTTCACCTAGATCCTTTTAAATTAAAAATGAAGTTTTAAATCAATCTAAAGTATATATGAGTAAACTTGGTC

TGACAGTTACCAATGCTTAATCAGTGAGGCACCTATCTCAGCGATCTGTCTATTTCGTTCATCCATAGTTGCCTG

ACTCCCCGTCGTGTAGATAACTACGATACGGGAGGGCTTACCATCTGGCCCCAGTGCTGCAATGATACCGCGAGA

CCCACGCTCACCGGCTCCAGATTTATCAGCAATAAACCAGCCAGCCGGAAGGGCCGAGCGCAGAAGTGGTCCTGC

AACTTTATCCGCCTCCATCCAGTCTATTAATTGTTGCCGGGAAGCTAGAGTAAGTAGTTCGCCAGTTAATAGTTT

GCGCAACGTTGTTGCCATTGCTACAGGCATCGTGGTGTCACGCTCGTCGTTTGGTATGGCTTCATTCAGCTCCGG

TTCCCAACGATCAAGGCGAGTTACATGATCCCCCATGTTGTGCAAAAAAGCGGTTAGCTCCTTCGGTCCTCCGAT

CGTTGTCAGAAGTAAGTTGGCCGCAGTGTTATCACTCATGGTTATGGCAGCACTGCATAATTCTCTTACTGTCAT

GCCATCCGTAAGATGCTTTTCTGTGACTGGTGAGTACTCAACCAAGTCATTCTGAGAATAGTGTATGCGGCGACC

GAGTTGCTCTTGCCCGGCGTCAATACGGGATAATACCGCGCCACATAGCAGAACTTTAAAAGTGCTCATCATTGG

AAAACGTTCTTCGGGGCGAAAACTCTCAAGGATCTTACCGCTGTTGAGATCCAGTTCGATGTAACCCACTCGTGC

ACCCAACTGATCTTCAGCATCTTTTACTTTCACCAGCGTTTCTGGGTGAGCAAAAACAGGAAGGCAAATGCCGC

AAAAAAGGGAATAAGGGCGACACGGAAATGTTGAATACTCATACTCTTCCTTTTTCAATATTATTGAAGCATTTA

TCAGGGTTATTGTCTCATGAGCGGATACATATTTGAATGTATTTAGAAAAATAAACAAATAGGGGTTCCGCGCAC

ATTTCCCCGAAAAGTGCCACCTGACGTCTAAGAAACCATTATTATCATGACATTAACCTATAAAAATAGGCGTAT

CACGAGGCCCTTTCGTC
```

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference.

Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for producing a fucosylated oligosaccharide in an *E.coli* bacterium, comprising
   (a) providing an *E.coli* bacterium comprising a β-galactosidase activity between 0.05 and 5 units and a mutation in a lacA gene, wherein said E.coli bacterium further comprises an exogenous lactose-accepting fucosyltransferase gene;
   (b) culturing said *E.coli* bacterium in the presence of lactose; and
   (c) retrieving a fucosylated oligosaccharide from said *E.coli* bacterium or from a culture supernatant of said *E.coli* bacterium,
   wherein a functional β-galactosidase gene is inserted into an endogenous gene of said *E. coli* bacterium.

2. The method of claim 1, wherein said mutation prevents the formation of intracellular acetyl-lactose.

3. The method of claim 1, wherein said *E.coli* bacterium further comprises a defective colanic acid synthesis pathway.

4. The method of claim 1, wherein said defective colanic acid synthesis pathway comprises a mutation in a colanic acid synthesis gene.

5. The method of claim 4, wherein said colanic acid synthesis gene comprises a wcaJ, wzxC, wcaD, wza, wzb, or wzc gene.

6. The method of claim 1, further comprising an inactivating mutation in a lon gene.

7. The method of claim 6, wherein said bacterium comprises a functional promoter-less wild-type *E. coli* lacZ⁺ gene inserted into said lon gene.

8. The method of claim 1, wherein said bacterium further comprises an exogenous *E. coli* rcsA or *E. coli* rcsB gene.

9. The method of claim 1, wherein said exogenous lactose-accepting fucosyltransferase gene comprises a Bacteroides fragilis wcfW gene or a *Helicobacter pylori* 26695 futA gene.

10. The method of claim 1, wherein said bacterium comprises both an exogenous fucosyltransferase gene encoding α(1,2) fucosyltransferase and an exogenous fucosyltransferase gene encoding α(1,3) fucosyltransferase.

11. The method of claim 1, wherein said bacterium comprises an endogenous lacY gene.

12. The method of claim 1, wherein said bacterium comprises a lactose permease gene.

13. The method of claim 12, wherein said lactose permease gene comprises an exogenous lactose permease gene.

14. The method of claim 1, wherein said *E.coli* bacterium comprises a deletion of an endogenous β-galactosidase gene.

15. The method of claim 1, wherein said bacterium accumulates an increased cytoplasmic lactose level, wherein the increased intracellular lactose level is at least 10% more than the level in a corresponding wild type bacterium.

16. The method of claim 1, wherein said fucosylated oligosaccharide comprises 2'-fucosyllactose, 3-fucosyllactose, or lactodifucotetraose.

17. The method of claim 1, wherein culturing said bacterium in step (b) does not comprise an antibiotic.

18. The method of claim 1, wherein said bacterium comprises a plasmid expression vector.

19. The method of claim 1, wherein said bacterium comprises an exogenous fucosyltransferase gene encoding α(1,2) fucosyltransferase or an exogenous fucosyltransferase gene encoding α(1,3) fucosyltransferase.

20. The method of claim 1, wherein said exogenous lactose-accepting fucosyltransferase gene comprises an α(1,3) fucosyltransferase gene from *Helicobacter pylori*, *H. hepaticus*, *H. bilis*, *Campylobacter jejuni*, or a species of Bacteroides.

21. The method of claim 1, wherein said exogenous lactose-accepting fucosyltransferase gene comprises a *E. coli* strain O128:B12 wbsJ gene, a *Helicobacter pylori* 26695 futC gene, a *H. hepaticus* Hh0072 gene, a *H. pylori* 11639 FucTa gene, or a *H. pylori* UA948 FucTa gene.

* * * * *

SEQUENCE LISTING

```
<160> NUMBER OF SEQ ID NOS: 15

<210> SEQ ID NO 1
<211> LENGTH: 6165
<212> TYPE: DNA
<213> ORGANISM: Artificial Sequence
<220> FEATURE:
<223> OTHER INFORMATION: Sequence of PG175.

<400> SEQUENCE: 1
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
```

```
gattggttac ggcgcgtttc gcatcattgt tgagtttttc cgccagcccg acgcgcagtt      360
taccggtgcc tgggtgcagt acatcagcat ggggcaaatt ctttccatcc cgatgattgt      420
cgcgggtgtg atcatgatgg tctgggcata tcgtcgcagc ccacagcaac acgtttcctg      480
aggaaccatg aaacagtatt tagaactgat gcaaaaagtg ctcgacgaag gcacacagaa      540
aaacgaccgt accggaaccg gaacgctttc cattttggt catcagatgc gttttaacct      600
gcaagatgga ttcccgctgg tgacaactaa acgttgccac ctgcgttcca tcatccatga      660
actgctgtgg tttctgcagg gcgacactaa cattgcttat ctacacgaaa caatgtcac      720 catctgggac gaatgggccg atgaaaacgg cgacctcggg ccagtgtatg gtaaacagtg      780
gcgcgcctgg ccaacgccag atggtcgtca tattgaccag atcactacgg tactgaacca      840
gctgaaaaac gacccggatt cgcgccgcat tattgtttca gcgtggaacg taggcgaact      900
ggataaaatg gcgctggcac cgtgccatgc attcttccag ttctatgtgg cagacggcaa      960
actctcttgc cagctttatc agcgctcctg tgacgtcttc ctcggcctgc cgttcaacat     1020
tgccagctac gcgttattgg tgcatatgat ggcgcagcag tgcgatctgg aagtgggtga     1080
ttttgtctgg accggtggcg acacgcatct gtacagcaac catatggatc aaactcatct     1140
gcaattaagc cgcgaaccgc gtccgctgcc gaagttgatt atcaaacgta acccgaatc     1200 catcttcgac taccgtttcg aagactttga gattgaaggc tacgatccgc atccgggcat     1260
taaagcgccg gtggctatct aattacgaaa catcctgcca gagccgacgc cagtgtgcgt     1320
cggttttttt accctccgtt aaattcttcg agacgcctt ccgaaggcgc cattcgccat     1380
tcaggctgcg caactgttgg aagggcgat cggtgcgggc ctcttcgcta ttacgccagc     1440
tggcgaaagg gggatgtgct gcaaggcgat taagttgggt aacgccaggg ttttcccagt     1500
cacgacgttg taaaacgacg gccagtgcca agctttcttt aatgaagcag ggcatcagga     1560
cggtatcttt gtggagaaag cagagtaatc ttattcagcc tgactggtgg gaaaccacca     1620
gtcagaatgt gttagcgcat gttgacaaaa ataccattag tcacattatc cgtcagtcgg     1680
acgacatggt agataacctg tttattatgc gttttgatct tacgtttaat attacccttta     1740 tgcgatgaaa cggtcttggc tttgatattc atttggtcag agatttgaat ggttccctga     1800
cctgccatcc acattcgcaa catactcgat tcggttcggc tcaatgataa cgtcggcata     1860
tttaaaaacg aggttatcgt tgtctctttt ttcagaatat cgccaaggat atcgtcgaga     1920
gattccggtt taatcgattt agaactgatc aataaatttt ttctgaccaa tagatattca     1980
tcaaaatgaa cattggcaat tgccataaaa acgataaata acgtattggg atgttgatta     2040
atgatgagct tgatacgctg actgttagaa gcatcgtgga tgaaacagtc ctcattaata     2100
aacaccactg aagggcgctg tgaatcacaa gctatgcaa ggtcatcaac ggtttcaatg     2160
tcgttgattt ctcttttttt aaccctctcta ctcaacagat acccggttaa acctagtcgg     2220
gtgtaactac ataaatccat aataatcgtt gacatggcat accctcactc aatgcgtaac     2280
gataattccc cttacctgaa tatttcatca tgactaaacg gaacaacatg ggtcacctaa     2340
tgcgccactc tcgcgatttt tcaggcggac ttactatccc gtaaagtgtt gtataatttg     2400
cctggaattg tcttaaagta aagtaaatgt tgcgatatgt gagtgagctt aaaacaaata     2460
tttcgctgca ggagtatcct ggaagatgtt cgtagaagct tactgctcac aagaaaaaag     2520
gcacgtcatc tgacgtgcct ttttatttg tactaccctg tacgattact gcagctcgag     2580
ttattataat tttacccacg attcgggaat aatatcatgt ttaatatctt tcttaaacca     2640
```

```
tttactcgga gcaattactg ttttattttt attttcattt aaccaagcag cccaccaact    2700
gaaagaacta tttgaaatta tattatttt acatttactc ataagcagca tatctaattc    2760
aacatgataa gcatcacctt gaacaaaaca tatttgatta ttaaaaaata tattttccct    2820
gcaccacttt atatcatcag aaaaaatgaa gagaagggtt ttttattaa taacacctt    2880
attcatcaaa taatcaatgg cacgttcaaa atatttttca ctacatgtgc catgagtttc    2940
atttgctatt ttactggaaa cataatcacc tcttctaata tgtaatgaac aagtatcatt    3000
ttctttaatt aaattaagca attcattttg ataactatta aacttggttt taggttgaaa    3060
ttcctttatc aactcatgcc taaattcctt aaaatatttt tcagtttgaa ataaccgac    3120
gatttttta tttatacttt tggtatcaat atctggatca tactctaaac ttttctcaac    3180
gtaatgcttt ctgaacattc ctttttcat gaaatgtggg atttttcgg aaaataagta    3240
tttttcaaat ggccatgctt tttacaaa ttctgaacta caagataatt caactaatct    3300
taatggatga gttttatatt ttactgcatc agatatatca acagtcaaat tttgatgagt    3360
tcttttgca atagcaaatg cagttgcata ctgaaacatt tgattaccaa gaccaccaat    3420
aattttaact tccatatgta tatctccttc ttctagaatt ctaaaaattg attgaatgta    3480
tgcaaataaa tgcatacacc ataggtgtgg tttaattgt atgcccttttt cagggctgga    3540
atgtgtaaga gcggggttat ttatgctgtt gtttttttgt tactcgggaa gggctttacc    3600
tcttccgcat aaacgcttcc atcagcgttt atagttaaaa aatctttcg gaactggttt    3660
tgcgcttacc ccaaccaaca ggggatttgc tgctttccat tgagcctgtt tctctgcgcg    3720
acgttcgcgg cggcgtgttt gtgcatccat ctggattctc ctgtcagtta gctttggtgg    3780
tgtgtggcag ttgtagtcct gaacgaaaac cccccgcgat tggcacattg gcagctaatc    3840
cggaatcgca cttacggcca atgcttcgtt tcgtatcaca caccccaaag ccttctgctt    3900
tgaatgctgc ccttcttcag ggcttaattt ttaagagcgt caccttcatg gtggtcagtg    3960
cgtcctgctg atgtgctcag tatcaccgcc agtggtattt atgtcaacac cgccagagat    4020
aatttatcac cgcagatggt tatctgtatg ttttttatat gaatttatttt tttgcagggg    4080
ggcattgttt ggtaggtgag agatcaattc tgcattaatg aatcggccaa cgcgcgggga    4140
gaggcggttt gcgtattggg cgctcttccg cttcctcgct cactgactcg ctgcgctcgg    4200
tcgttcggct gcggcgagcg gtatcagctc actcaaaggc ggtaatacgg ttatccacag    4260
aatcagggga taacgcagga agaacatgt gagcaaaagg ccagcaaaag gccaggaacc    4320
gtaaaaaggc cgcgttgctg gcgttttttcc ataggctccg ccccctgac gagcatcaca    4380
aaaatcgacg ctcaagtcag aggtggcgaa acccgacagg actataaaga taccaggcgt    4440
ttccccctgg aagctccctc gtgcgctctc ctgttccgac cctgccgctt accgatacc    4500
tgtccgcctt tctcccttcg ggaagcgtgg cgctttctca tagctcacgc tgtaggtatc    4560
tcagttcggt gtaggtcgtt cgctccaagc tgggctgtgt gcacgaaccc ccgttcagc    4620
ccgaccgctg cgccttatcc ggtaactatc gtcttgagtc caacccggta agacacgact    4680
tatcgccact ggcagcagcc actggtaaca ggattagcag agcgaggtat gtaggcggtg    4740
ctacagagtt cttgaagtgg tggcctaact acggctacac tagaaggaca gtatttggta    4800
tctgcgctct gctgaagcca gttaccttcg gaaaaagagt ggtagctct tgatccggca    4860
aacaaaccac cgctggtagc ggtggttttt ttgtttgcaa gcagcagatt acgcgcagaa    4920
aaaaaggatc tcaagaagat cctttgatct ttttctacggg gtctgacgct cagtggaacg    4980
aaaactcacg ttaagggatt ttggtcatga gattatcaaa aaggatcttc acctagatcc    5040
```

```
ttttaaatta aaaatgaagt tttaaatcaa tctaaagtat atatgagtaa acttggtctg    5100
acagttacca atgcttaatc agtgaggcac ctatctcagc gatctgtcta tttcgttcat    5160
ccatagttgc ctgactcccc gtcgtgtaga taactacgat acgggagggc ttaccatctg    5220
gccccagtgc tgcaatgata ccgcgagacc cacgctcacc ggctccagat ttatcagcaa    5280
taaaccagcc agccggaagg gccgagcgca gaagtggtcc tgcaacttta tccgcctcca    5340
tccagtctat taattgttgc cgggaagcta gagtaagtag ttcgccagtt aatagtttgc    5400
gcaacgttgt tgccattgct acaggcatcg tggtgtcacg ctcgtcgttt ggtatggctt    5460
cattcagctc cggttcccaa cgatcaaggc gagttacatg atcccccatg ttgtgcaaaa    5520
aagcggttag ctccttcggt cctccgatcg ttgtcagaag taagttggcc gcagtgttat    5580
cactcatggt tatggcagca ctgcataatt ctcttactgt catgccatcc gtaagatgct    5640
tttctgtgac tggtgagtac tcaaccaagt cattctgaga atagtgtatg cggcgaccga    5700
gttgctcttg cccggcgtca atacgggata ataccgcgcc acatagcaga actttaaaag    5760
tgctcatcat tggaaaacgt tcttcggggc gaaaactctc aaggatctta ccgctgttga    5820
gatccagttc gatgtaaccc actcgtgcac ccaactgatc ttcagcatct tttactttca    5880
ccagcgtttc tgggtgagca aaaacaggaa ggcaaaatgc cgcaaaaaag ggaataaggg    5940
cgacacggaa atgttgaata ctcatactct tcctttttca atattattga agcatttatc    6000
agggttattg tctcatgagc ggatacatat ttgaatgtat ttagaaaaat aaacaaatag    6060
gggttccgcg cacatttccc cgaaaagtgc cacctgacgt ctaagaaacc attattatca    6120
tgacattaac ctataaaaat aggcgtatca cgaggccctt tcgtc              6165
```

<210> SEQ ID NO 2
<211> LENGTH: 6290
<212> TYPE: DNA
<213> ORGANISM: Artificial Sequence
<220> FEATURE:
<223> OTHER INFORMATION: Sequence of pG176.

<400> SEQUENCE: 2

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatatg cggtgtgaaa taccgcacag atgcgtaagg agaaaatacc gcatcaggcg     240
ccatgaaaca gtatttagaa ctgatgcaaa agtgctcga cgaaggcaca cagaaaaacg     300
accgtaccgg aaccggaacg ctttccattt ttggtcatca gatgcgtttt aacctgcaag     360
atggattccc gctggtgaca actaaacgtt gccacctgcg ttccatcatc catgaactgc     420 tgtggttct gcagggcgac actaacattg cttatctaca cgaaaacaat gtcaccatct     480
gggacgaatg ggccgatgaa aacgcgacc tcgggccagt gtatggtaaa cagtggcgcg     540
cctggccaac gccagatggt cgtcatattg accagatcac tacggtactg aaccagctga     600
aaaacgaccc ggattcgcgc cgcattattg tttcagcgtg gaacgtaggc gaactggata     660
aaatggcgct ggcaccgtgc catgcattct tccagttcta tgtggcagac ggcaaactct     720
cttgccagct ttatcagcgc tcctgtgacg tcttcctcgg cctgccgttc aacattgcca     780
gctacgcgtt attggtgcat atgatggcgc agcagtgcga tctggaagtg ggtgattttg     840
tctggaccgg tggcgacacg catctgtaca gcaaccatat ggatcaaact catctgcaat     900
```

-continued

```
taagccgcga accgcgtccg ctgccgaagt tgattatcaa acgtaaaccc gaatccatct    960
tcgactaccg tttcgaagac tttgagattg aaggctacga tccgcatccg ggcattaaag   1020
cgccggtggc tatctaaggc gccattcgcc attcaggctg cgcaactgtt gggaagggcg   1080
atcggtgcgg gcctcttcgc tattacgcca gctggcgaaa gggggatgtg ctgcaaggcg   1140
attaagttgg gtaacgccag ggttttccca gtcacgacgt tgtaaaacga cggccagtgc   1200
caagctttct ttaatgaagc agggcatcag gacggtatct tgtgggagaa agcagagtaa   1260
tcttattcag cctgactggt gggaaaccac cagtcagaat gtgttagcgc atgttgacaa   1320
aaataccatt agtcacatta ccgtcagtc ggacgacatg gtagataacc tgtttattat   1380
gcgttttgat cttacgttta atattacctt tatgcgatga aacggtcttg gctttgatat   1440
tcatttggtc agagatttga atggttccct gacctgccat ccacattcgc aacatactcg   1500
attcggttcg gctcaatgat aacgtcggca tatttaaaaa cgaggttatc gttgtctctt   1560
ttttcagaat atcgccaagg atatcgtcga gagattccgg tttaatcgat ttagaactga   1620
tcaataaatt ttttctgacc aatagatatt catcaaaatg aacattggca attgccataa   1680
aaacgataaa taacgtattg ggatgttgat taatgatgag cttgatacgc tgactgttag   1740
aagcatcgtg gatgaaacag tcctcattaa taaaacaccac tgaagggcgc tgtgaatcac   1800
agctatggc aaggtcatca acggtttcaa tgtcgttgat ttctcttttt ttaacccctc   1860
tactcaacag atacccggtt aaacctagtc gggtgtaact acataaatcc ataataatcg   1920
ttgacatggc atacccctcac tcaatgcgta acgataattc cccttacctg aatatttcat   1980
catgactaaa cggaacaaca tgggtcacct aatgcgccac tctcgcgatt tttcaggcgg   2040
acttactatc ccgtaaagtg ttgtataatt tgcctggaat tgtcttaaag taaagtaaat   2100
gttgcgatat gtgagtgagc ttaaaacaaa tatttcgctg caggagtatc ctggaagatg   2160
ttcgtagaag cttactgctc acaagaaaaa aggcacgtca tctgacgtgc ctttttattt   2220
tgtactaccc tgtacgatta ctgcagctcg agttaattca aatcttcttc agaaatcaat   2280
ttttgttcca aacccaattt tttaaccaac tttctcaccg cgcgcaacaa aggcaaggat   2340
ttttgataag ctttgcgata gattttaaaa gtggtgtttt gagagagttc taataaaggc   2400
gaagcgtttt gtaaaagccg gtcataatta accctcaaat catcataatt aaccctcaaa   2460
tcatcaatgg atactaacgg cttatgcaga tcgtactccc acatgaaaga tgttgagaat   2520
ttgtgataaa tcgtatcgtt ttctaaaatc gttttaaaaa aatctaggat tttttttaaaa   2580
ctcaaatctt ggtaaaagta agcttttccca tcaagggtgt ttaaagggtt ttcatagagc   2640
atgtctaaat aagcgtttgg gtgcgtgtgc aggtatttga tataatcaat cgcttcatca   2700
aagttgttga atcatgcac attcacaaaa cttttagggt taaaatcttt cgccacgctg   2760
ggactccccc aataaatagg aatggtatgg ctaaaatacg catcaaggat ttttttcggtt   2820
acatagccat aaccttgcga gttttcaaaa cagagattga acttgtattg gcttaaaaac   2880
tcgcttttgt ttccaacctt atagcctaaa gtgtttctca cttcctcc cccagtaact   2940
ggctctatgg aatttagagc gtcataaaaa gcgttcctca taggagcgtt agcgttgctc   3000
gctacaaaac tggcaaaccc tctttttaaa agatcgctct catcattcac tactgcgcac   3060
aaattagggt ggttttcttt aaaatgatga gagggttttt ttaaagcata aggctgttg    3120
tctttgagtt tgtagggcgc agtggtgtca ttaacaagct cggctttata gtgcaaatgg   3180
gcataataca aaggcattct caaataacga tcattaaaat ccaattcatc aaagcctatg   3240
gcgtaatcaa agaggttgaa attaggtgat tcgttttcac cggtgtaaaa cactcgttta   3300
```

```
gtgttttgat aagataaaat ctttctagcc gctccaagag gattgctaaa aactagatct    3360
gaaaattcat tgggttttg gtggagggtg attgcgtagc gttggcttag gataaaataa    3420
agaacgctct ttttaaattc tttaatttct tcatctcccc accaattcgc cacagcgatt    3480 tttaggggg ggggggagaa tttagaggcc attttttcaa tggaagcgct ttctataaag    3540
gcgtctaata ggggttggaa catatgtata tctccttctt gaattctaaa aattgattga    3600
atgtatgcaa ataaatgcat acaccatagg tgtggtttaa tttgatgccc ttttttcaggg   3660 ctggaatgtg taagagcggg gttatttatg ctgttgtttt tttgttactc gggaagggct    3720
ttacctcttc cgcataaacg cttccatcag cgtttatagt taaaaaaatc tttcggaact    3780
ggttttgcgc ttaccccaac caacagggga tttgctgctt tccattgagc ctgtttctct    3840
gcgcgacgtt cgcggcggcg tgtttgtgca tccatctgga ttctcctgtc agttagcttt    3900
ggtggtgtgt ggcagttgta gtcctgaacg aaaacccccc gcgattggca cattggcagc    3960
taatccggaa tcgcacttac ggccaatgct tcgtttcgta tcacacaccc caaagccttc    4020
tgctttgaat gctgcccttc ttcagggctt aattttttaag agcgtcacct tcatggtggt    4080
cagtgcgtcc tgctgatgtg ctcagtatca ccgccagtgg tatttatgtc aacaccgcca    4140
gagataattt atcaccgcag atggttatct gtatgttttt tatatgaatt tatttttttgc    4200 aggggggcat tgtttggtag gtgagagatc aattctgcat taatgaatcg gccaacgcgc    4260
ggggagaggc ggtttgcgta ttgggcgctc ttccgcttcc tcgctcactg actcgctgcg    4320
ctcggtcgtt cggctgcggc gagcggtatc agctcactca aaggcggtaa tacggttatc    4380
cacagaatca ggggataacg caggaaagaa catgtgagca aaaggccagc aaaaggccag    4440
gaaccgtaaa aaggccgcgt tgctggcgtt tttccatagg ctccgccccc ctgacgagca    4500
tcacaaaaat cgacgctcaa gtcagaggtg gcgaaacccg acaggactat aaagatacca    4560
ggcgtttccc cctggaagct ccctcgtgcg ctctcctgtt ccgaccctgc cgcttaccgg    4620
atacctgtcc gcctttctcc cttcgggaag cgtggcgctt tctcatagct cacgctgtag    4680
gtatctcagt tcggtgtagg tcgttcgctc caagctgggc tgtgtgcacg aaccccccgt    4740
tcagcccgac cgctgcgcct tatccggtaa ctatcgtctt gagtccaacc cggtaagaca    4800
cgacttatcg ccactggcag cagccactgg taacaggatt agcagagcga ggtatgtagg    4860
cggtgctaca gagttcttga agtggtggcc taactacggc tacactagaa ggacagtatt    4920
tggtatctgc gctctgctga agccagttac cttcggaaaa agagttggta gctcttgatc    4980
cggcaaacaa accaccgctg gtagcggtgg tttttttgtt tgcaagcagc agattacgcg    5040
cagaaaaaaa ggatctcaag aagatccttt gatcttttct acggggtctg acgctcagtg    5100
gaacgaaaac tcacgttaag ggattttggt catgagatta tcaaaaagga tcttcaccta    5160
gatcctttta aattaaaaat gaagttttaa atcaatctaa agtatatatg agtaaacttg    5220
gtctgacagt taccaatgct taatcagtga ggcacctatc tcagcgatct gtctatttcg    5280
ttcatccata gttgcctgac tccccgtcgt gtagataact acgatacggg agggcttacc    5340
atctggcccc agtgctgcaa tgataccgcg agacccacgc tcaccggctc cagatttatc    5400
agcaataaac cagccagccg gaagggccga gcgcagaagt ggtcctgcaa ctttatccgc    5460
ctccatccag tctattaatt gttgccggga agctagagta agtagttcgc cagttaatag    5520
tttgcgcaac gttgttgcca ttgctacagg catcgtggtg tcacgctcgt cgtttggtat    5580
ggcttcattc agctccggtt cccaacgatc aaggcgagtt acatgatccc ccatgttgtg    5640
```

| | |
|---|---|
| caaaaaagcg gttagctcct tcggtcctcc gatcgttgtc agaagtaagt tggccgcagt | 5700 |
| gttatcactc atggttatgg cagcactgca taattctctt actgtcatgc catccgtaag | 5760 |
| atgcttttct gtgactggtg agtactcaac caagtcattc tgagaatagt gtatgcggcg | 5820 |
| accgagttgc tcttgcccgg cgtcaatacg ggataatacc gcgccacata gcagaacttt | 5880 |
| aaaagtgctc atcattggaa aacgttcttc ggggcgaaaa ctctcaagga tcttaccgct | 5940 |
| gttgagatcc agttcgatgt aacccactcg tgcacccaac tgatcttcag catcttttac | 6000 |
| tttcaccagc gtttctgggt gagcaaaaac aggaaggcaa aatgccgcaa aaagggaat | 6060 |
| aagggcgaca cggaaatgtt gaatactcat actcttcctt tttcaatatt attgaagcat | 6120 |
| ttatcagggt tattgtctca tgagcggata catatttgaa tgtatttaga aaaataaaca | 6180 |
| aataggggtt ccgcgcacat ttccccgaaa agtgccacct gacgtctaag aaaccattat | 6240 |
| tatcatgaca ttaacctata aaaataggcg tatcacgagg ccctttcgtc | 6290 |

<210> SEQ ID NO 3
<211> LENGTH: 7250
<212> TYPE: DNA
<213> ORGANISM: Artificial Sequence
<220> FEATURE:
<223> OTHER INFORMATION: Sequence of pG177.

<400> SEQUENCE: 3

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatatg cggtgtgaaa taccgcacag atgcgtaagg agaaaatacc gcatcaggcg | 240 |
| ccatgaaaca gtatttagaa ctgatgcaaa aagtgctcga cgaaggcaca cagaaaaacg | 300 |
| accgtaccgg aaccggaacg ctttccattt ttggtcatca gatgcgtttt aacctgcaag | 360 |
| atggattccc gctggtgaca actaaacgtt gccacctgcg ttccatcatc catgaactgc | 420 |
| tgtggtttct gcagggcgac actaacattg cttatctaca cgaaaacaat gtcaccatct | 480 |
| gggacgaatg ggccgatgaa aacggcgacc tcgggccagt gtatggtaaa cagtggcgcg | 540 |
| cctggccaac gccagatggt cgtcatattg accagatcac tacggtactg aaccagctga | 600 |
| aaaacgaccc ggattcgcgc cgcattattg tttcagcgtg aacgtaggc gaactggata | 660 |
| aaatggcgct ggcaccgtgc catgcattct tccagttcta tgtggcagac ggcaaactct | 720 |
| cttgccagct ttatcagcgc tcctgtacg tcttcctcgg cctgccgttc aacattgcca | 780 |
| gctacgcgtt attggtgcat atgatggcgc agcagtgcga tctggaagtg ggtgattttg | 840 |
| tctggaccgg tggcgacacg catctgtaca gcaaccatat ggatcaaact catctgcaat | 900 |
| taagccgcga accgcgtccg ctgccgaagt tgattatcaa acgtaaaccc gaatccatct | 960 |
| tcgactaccg tttcgaagac tttgagattg aaggctacga tccgcatccg gcattaaag | 1020 |
| cgccggtggc tatctaaggc gccattcgcc attcaggctg cgcaactgtt gggaagggcg | 1080 |
| atcggtgcgg gcctcttcgc tattacgcca gctggcgaaa gggggatgtg ctgcaaggcg | 1140 |
| attaagttgg gtaacgccag gttttccca gtcacgacgt tgtaaaacga cggccagtgc | 1200 |
| caagctttct ttaatgaagc agggcatcag gacggtatct ttgtggagaa agcagagtaa | 1260 |
| tcttattcag cctgactggt gggaaaccac cagtcagaat gtgttagcgc atgttgacaa | 1320 |
| aaataccatt agtcacatta ccgtcagtc ggacgacatg gtagataacc tgtttattat | 1380 |
| gcgttttgat cttacgttta atattacctt tatgcgatga acggtcttg gctttgatat | 1440 |

| | |
|---|---|
| tcatttggtc agagatttga atggttccct gacctgccat ccacattcgc aacatactcg | 1500 |
| attcggttcg gctcaatgat aacgtcggca tatttaaaaa cgaggttatc gttgtctctt | 1560 |
| ttttcagaat atcgccaagg atatcgtcga gagattccgg tttaatcgat ttagaactga | 1620 |
| tcaataaatt ttttctgacc aatagatatt catcaaaatg aacattggca attgccataa | 1680 |
| aaacgataaa taacgtattg ggatgttgat taatgatgag cttgatacgc tgactgttag | 1740 |
| aagcatcgtg gatgaaacag tcctcattaa taaacaccac tgaagggcgc tgtgaatcac | 1800 |
| aagctatggc aaggtcatca acggtttcaa tgtcgttgat ttctcttttt ttaacccctc | 1860 |
| tactcaacag atacccggtt aaacctagtc gggtgtaact acataaatcc ataataatcg | 1920 |
| ttgacatggc atacccctcac tcaatgcgta acgataattc cccttacctg aatatttcat | 1980 |
| catgactaaa cggaacaaca tgggtcacct aatgcgccac tctcgcgatt tttcaggcgg | 2040 |
| acttactatc ccgtaaagtg ttgtataatt tgcctggaat tgtcttaaag taaagtaaat | 2100 |
| gttgcgatat gtgagtgagc ttaaaacaaa tatttcgctg caggagtatc ctggaagatg | 2160 |
| ttcgtagaag cttactgctc acaagaaaaa aggcacgtca tctgacgtgc cttttttatt | 2220 |
| tgtactaccc tgtacgatta ctgcagctcg agttaattca atcttcttc agaaatcaat | 2280 |
| ttttgttcag cgttatactt ttgggatttt acctcaaaat gggattctat tttcacccac | 2340 |
| tccttacaaa ggatattctc atgcccaaaa agccagtgtt tggggccaat aatgattttt | 2400 |
| tctggatttt ctatcaaata ggccgcccac cagctataag tgctattagc gataatgcca | 2460 |
| tgctgacaag attgcatgag cagcatgtcc aatacgcct cttcttcttt atccctagtg | 2520 |
| gtcatgtcca taaagggta gccaagatca agattttgcg tgaattctaa gtcttcgcaa | 2580 |
| aacacaaaaa gctccatgtt tggcacgcgc tttgccatat actcaagcgc cttttttga | 2640 |
| tagtcaatac caagctgaca gccaatcccc acataatccc ctcttcttat atgcacaaac | 2700 |
| acgctgtttt tagcggctaa aatcaaagaa agcttgcact gatattcttc ctcttttta | 2760 |
| ttattattct tattattttc gggtggtggt ggtagagtga aggtttgctt gattaaaggg | 2820 |
| gatatagcat caaagtatcg tggatcttgg aaatagccaa aaaaataagt caagcggctt | 2880 |
| ggctttagca atttaggctc gtattcaaaa acgatttctt gactcaccct atcaaatccc | 2940 |
| atgcatttga gcgcgtctct tactagcttg gggaggtgtt gcattttagc tatagcgatt | 3000 |
| tctttcgcgc tcgcatagg caaatcaata gggaaaagtt ctaattgcat tttcctatcg | 3060 |
| ctccaatcaa aagaagtgat atctaacagc acaggcgtat tagagtgttt ttgcaaactt | 3120 |
| ttagcgaaag cgtattgaaa catttgattc ccaagccctc cgcaaatttg caccaccta | 3180 |
| aaagccatat gtatatctcc ttcttgctcg agttaattca atcttcttc agaaatcaat | 3240 |
| ttttgttcca aacccaattt tttaaccaac tttctcaccg cgcgcaacaa aggcaaggat | 3300 |
| ttttgataag ctttgcgata gatttttaaaa gtggtgtttt gagagagttc taataaaggc | 3360 |
| gaagcgtttt gtaaaagccg gtcataatta accctcaaat catcataatt aaccctcaaa | 3420 |
| tcatcaatgg atactaacgg cttatgcaga tcgtactccc acatgaaaga tgttgagaat | 3480 |
| ttgtgataaa tcgtatcgtt ttctaaaatc gttttaaaaa atctaggat ttttttaaaa | 3540 |
| ctcaaatctt ggtaaaagta agctttccca tcaagggtgt ttaaagggtt tcatagagc | 3600 |
| atgtctaaat aagcgtttgg gtgcgtgtgc aggtatttga tataatcaat cgcttcatca | 3660 |
| aagttgttga aatcatgcac attcacaaaa cttttagggt taaaatcttt cgccacgctg | 3720 |
| ggactccccc aataaatagg aatggtatgg ctaaaatacg catcaaggat ttttttcggtt | 3780 |

```
acatagccat aaccttgcga gttttcaaaa cagagattga acttgtattg gcttaaaaac    3840
tcgcttttgt ttccaacctt atagcctaaa gtgtttctca cacttcctcc cccagtaact    3900
ggctctatgg aatttagagc gtcataaaaa gcgttcctca taggagcgtt agcgttgctc    3960
gctacaaaac tggcaaaccc tcttttaaa agatcgctct catcattcac tactgcgcac     4020
aaattagggt ggttttcttt aaaatgatga gagggttttt ttaaagcata aaggctgttg    4080
tctttgagtt tgtagggcgc agtggtgtca ttaacaagct cggctttata gtgcaaatgg    4140
gcataataca aaggcattct caaataacga tcattaaaat ccaattcatc aaagcctatg    4200
gcgtaatcaa agaggttgaa attaggtgat tcgttttcac cggtgtaaaa cactcgttta    4260
gtgttttgat aagataaaat ctttctagcc gctccaagag gattgctaaa aactagatct    4320
gaaaattcat tggggttttg gtggagggtg attgcgtagc gttggcttag gataaaataa    4380
agaacgctct ttttaaattc tttaatttct tcatctcccc accaattcgc cacagcgatt    4440 tttaggggg ggggggagaa tttagaggcc attttttcaa tggaagcgct ttctataaag     4500
gcgtctaata ggggttggaa catatgtata tctccttctt gaattctaaa aattgattga    4560
atgtatgcaa ataaatgcat acaccatagg tgtggtttaa tttgatgccc ttttcaggg     4620 ctggaatgtg taagagcggg gttatttatg ctgttgtttt tttgttactc gggaagggct    4680
ttacctcttc cgcataaacg cttccatcag cgtttatagt taaaaaaatc tttcggaact    4740
ggttttgcgc ttaccccaac caacagggga tttgctgctt tccattgagc ctgtttctct    4800
gcgcgacgtt cgcggcggcg tgtttgtgca tccatctgga ttctcctgtc agttagcttt    4860
ggtggtgtgt ggcagttgta gtcctgaacg aaaaccccc gcgattggca cattggcagc     4920
taatccggaa tcgcacttac ggccaatgct tcgtttcgta tcacacaccc caaagccttc    4980
tgctttgaat gctgcccttc ttcagggctt aattttaag agcgtcacct tcatggtggt     5040
cagtgcgtcc tgctgatgtg ctcagtatca ccgccagtgg tatttatgtc aacaccgcca    5100
gagataattt atcaccgcag atggttatct gtatgttttt tatatgaatt tattttttgc    5160 agggggcat tgtttggtag gtgagagatc aattctgcat taatgaatcg ccaacgcgc     5220 ggggagaggc ggtttgcgta ttgggcgctc ttccgcttcc tcgctcactg actcgctgcg    5280
ctcggtcgtt cggctgcggc gagcggtatc agctcactca aaggcggtaa tacggttatc    5340
cacagaatca ggggataacg caggaaagaa catgtgagca aaaggccagc aaaaggccag    5400
gaaccgtaaa aaggccgcgt tgctggcgtt tttccatagg ctccgccccc ctgacgagca    5460
tcacaaaaat cgacgctcaa gtcagaggtg gcgaaacccg acaggactat aaagatacca    5520
ggcgtttccc cctggaagct ccctcgtgcg ctctcctgtt ccgaccctgc cgcttaccgg    5580
atacctgtcc gcctttctcc cttcgggaag cgtggcgctt tctcatagct cacgctgtag    5640
gtatctcagt tcggtgtagg tcgttcgctc caagctgggc tgtgtgcacg aaccccccgt    5700
tcagcccgac cgctgcgcct tatccggtaa ctatcgtctt gagtccaacc cggtaagaca    5760
cgacttatcg ccactggcag cagccactgg taacaggatt agcagagcga ggtatgtagg    5820
cggtgctaca gagttcttga agtggtggcc taactacggc tacactagaa ggacagtatt    5880
tggtatctgc gctctgctga agccagttac cttcggaaaa agagttggta gctcttgatc    5940
cggcaaacaa accaccgctg gtagcggtgg ttttttgtt tgcaagcagc agattacgcg     6000
cagaaaaaaa ggatctcaag aagatccttt gatcttttct acggggtctg acgctcagtg    6060
gaacgaaaac tcacgttaag ggattttggt catgagatta tcaaaaagga tcttcaccta    6120
gatcctttta aattaaaaat gaagttttaa atcaatctaa agtatatatg agtaaacttg    6180
```

```
gtctgacagt taccaatgct taatcagtga ggcacctatc tcagcgatct gtctatttcg      6240
ttcatccata gttgcctgac tccccgtcgt gtagataact acgatacggg agggcttacc      6300
atctggcccc agtgctgcaa tgataccgcg agacccacgc tcaccggctc cagatttatc      6360
agcaataaac cagccagccg gaagggccga gcgcagaagt ggtcctgcaa ctttatccgc      6420
ctccatccag tctattaatt gttgccggga agctagagta agtagttcgc cagttaatag      6480
tttgcgcaac gttgttgcca ttgctacagg catcgtggtg tcacgctcgt cgtttggtat      6540
ggcttcattc agctccggtt cccaacgatc aaggcgagtt acatgatccc ccatgttgtg      6600
caaaaaagcg gttagctcct tcggtcctcc gatcgttgtc agaagtaagt tggccgcagt      6660
gttatcactc atggttatgg cagcactgca taattctctt actgtcatgc catccgtaag      6720
atgcttttct gtgactggtg agtactcaac caagtcattc tgagaatagt gtatgcggcg      6780
accgagttgc tcttgcccgg cgtcaatacg ggataatacc gcgccacata gcagaacttt      6840
aaaagtgctc atcattggaa aacgttcttc ggggcgaaaa ctctcaagga tcttaccgct      6900
gttgagatcc agttcgatgt aacccactcg tgcacccaac tgatcttcag catctttac      6960 tttcaccagc gtttctgggt gagcaaaaac aggaaggcaa aatgccgcaa aaagggaat      7020 aagggcgaca cggaaatgtt gaatactcat actcttcctt tttcaatatt attgaagcat      7080
ttatcagggt tattgtctca tgagcggata catatttgaa tgtatttaga aaataaaca      7140 aatagggatt ccgcgcacat ttccccgaaa agtgccacct gacgtctaag aaaccattat      7200
tatcatgaca ttaacctata aaaataggcg tatcacgagg ccctttcgtc                7250
```

```
<210> SEQ ID NO 4
<211> LENGTH: 870
<212> TYPE: DNA
<213> ORGANISM: Bacteroides fragilis

<400> SEQUENCE: 4
atgattgtat catctttgcg aggaggattg gggaatcaaa tgtttattta cgctatggtg        60
aaggccatgg cattaagaaa caatgtacca ttcgctttta atttgactac tgattttgca       120
aatgatgaag tttataaaag gaaacttta ttatcatatt ttgcattaga cttgcctgaa        180
aataaaaaat taacatttga tttttcatat gggaattatt atagaaggct aagtcgtaat       240
ttaggttgtc atatacttca tccatcatat cgttatattt gcgaagagcg ccctccccac       300
tttgaatcaa ggttaattag ttctaagatt acaaatgctt ttctggaagg atattggcag       360
tcagaaaaat attttcttga ttataaacaa gagataaaag aggactttgt aatacaaaaa       420
aaattagaat acacatcgta tttggaattg aagaaataa aattgctaga taagaatgcc       480
ataatgattg gggttagacg gtatcaggaa agtgatgtag ctcctggtgg agtgttagaa       540
gatgattact ataaatgtgc tatggatatt atggcatcaa agttacttc tcctgttttc       600 ttttgttttt cacaagattt agaatgggtt gaaaaacatc tagcgggaaa atatcctgtt       660
cgtttgataa gtaaaaagga ggatgatagt ggtactatag atgatatgtt tctaatgatg       720
cattttcgta attatataat atcgaatagc tcttttttact ggtggggagc atggcttcg       780 aaatatgatg ataagctggt gattgctcca ggtaattta taaataagga ttctgtacca       840
gaatcttggt ttaaattgaa tgtaagataa                                         870
```

```
<210> SEQ ID NO 5
<211> LENGTH: 6244
<212> TYPE: DNA
```

<213> ORGANISM: Artificial Sequence
<220> FEATURE:
<223> OTHER INFORMATION: Sequence of pG171.

<400> SEQUENCE: 5

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
gattggttac ggcgcgtttc gcatcattgt tgagtttttc cgccagcccg acgcgcagtt     360
taccggtgcc tgggtgcagt acatcagcat ggggcaaatt ctttccatcc cgatgattgt     420
cgcgggtgtg atcatgatgg tctgggcata tcgtcgcagc ccacagcaac acgtttcctg     480
aggaaccatg aaacagtatt tagaactgat gcaaaaagtg ctcgacgaag gcacacagaa     540
aaacgaccgt accggaaccg gaacgctttc cattttggt catcagatgc gttttaacct      600
gcaagatgga ttcccgctgg tgacaactaa acgttgccac ctgcgttcca tcatccatga     660
actgctgtgt tttctgcagg gcgacactaa cattgcttat ctacacgaaa acaatgtcac     720
catctgggac gaatgggccg atgaaaacgg cgacctcggg ccagtgtatg gtaaacagtg     780
gcgcgcctgg ccaacgccag atggtcgtca tattgaccag atcactacgg tactgaacca     840
gctgaaaaac gacccggatt cgcgccgcat tattgtttca gcgtggaacg taggcgaact     900
ggataaaatg gcgctggcac cgtgccatgc attcttccag ttctatgtgg cagacggcaa     960
actctcttgc cagctttatc agcgctcctg tgacgtcttc ctcggcctgc cgttcaacat    1020
tgccagctac gcgttattgg tgcatatgat ggcgcagcag tgcgatctgg aagtgggtga    1080
ttttgtctgg accggtggcg acacgcatct gtacagcaac catatggatc aaactcatct    1140
gcaattaagc cgcgaaccgc gtccgctgcc gaagttgatt atcaaacgta aacccgaatc    1200
catcttcgac taccgtttcg aagactttga gattgaaggc tacgatccgc atccgggcat    1260
taaagcgccg gtggctatct aattacgaaa catcctgcca gagccgacgc cagtgtgcgt    1320
cggttttttt accctccgtt aaattcttcg agacgccttc ccgaaggcgc cattcgccat    1380
tcaggctgcg caactgttgg gaagggcgat cggtgcgggc ctcttcgcta ttacgccagc    1440
tggcgaaagg gggatgtgct gcaaggcgat taagttgggt aacgccaggg ttttcccagt    1500
cacgacgttg taaaacgacg gccagtgcca gctttctttt aatgaagcag ggcatcagga    1560
cggtatcttt gtggagaaag cagagtaatc ttattcagcc tgactggtgg gaaaccacca    1620
gtcagaatgt gttagcgcat gttgacaaaa ataccattag tcacattatc cgtcagtcgg    1680
acgacatggt agataacctg tttattatgc gttttgatct tacgtttaat attacccttta   1740
tgcgatgaaa cggtcttggc tttgatattc atttggtcag agatttgaat ggttccctga    1800
cctgccatcc acattcgcaa catactcgat tcggttcggc tcaatgataa cgtcggcata    1860
tttaaaaacg aggttatcgt tgtctctttt ttcagaatat cgccaaggat atcgtcgaga    1920
gattccggtt taatcgattt agaactgatc aataaatttt ttctgaccaa tagatattca    1980
tcaaaatgaa cattggcaat tgccataaaa acgataaata acgtattggg atgttgatta    2040
atgatgagct tgatacgctg actgttagaa gcatcgtgga tgaaacagtc ctcattaata    2100
aacaccactg aagggcgctg tgaatcacaa gctatgcaa ggtcatcaac ggtttcaatg      2160
tcgttgattt ctctttttt aacccctcta ctcaacagat acccggttaa acctagtcgg     2220
```

```
gtgtaactac ataaatccat aataatcgtt gacatggcat accctcactc aatgcgtaac    2280
gataattccc cttacctgaa tatttcatca tgactaaacg gaacaacatg ggtcacctaa    2340
tgcgccactc tcgcgatttt tcaggcggac ttactatccc gtaaagtgtt gtataatttg    2400
cctggaattg tcttaaagta aagtaaatgt tgcgatatgt gagtgagctt aaaacaaata    2460
tttcgctgca ggagtatcct ggaagatgtt cgtagaagct tactgctcac aagaaaaaag    2520
gcacgtcatc tgacgtgcct ttttatttg tactaccctg tacgattact gcagctcgag    2580
tttaattcaa atcttcttca gaaatcaatt tttgttcagc gttatacttt tgggatttta    2640
cctcaaaatg ggattctatt ttcacccact ccttacaaag gatattctca tgcccaaaaa    2700
gccagtgttt ggggccaata atgatttttt ctggattttc tatcaaatag gccgcccacc    2760
agctataagt gctattagcg ataatgccat gctgacaaga ttgcatgagc agcatgtccc    2820
aatacgcctc ttcttcttta tccctagtgg tcatgtccat aaaagggtag ccaagatcaa    2880 gatttttgcgt gaattctaag tcttcgcaaa acacaaaaag ctccatgttt ggcacgcgct    2940
ttgccatata ctcaagcgcc ttttttgat agtcaatacc aagctgacag ccaatcccca    3000
cataatcccc tcttcttata tgcacaaaca cgctgttttt agcggctaaa atcaaagaaa    3060
gcttgcactg atattcttcc tctttttat tattattctt attattttcg ggtggtggtg    3120
gtagagtgaa ggtttgcttg attaaagggg atatagcatc aaagtatcgt ggatcttgga    3180
aatagccaaa aaataagtc aagcggcttg gctttagcaa tttaggctcg tattcaaaaa    3240
cgatttcttg actcacccta tcaaatccca tgcatttgag cgcgtctctt actagcttgg    3300
ggaggtgttg cattttagct atagcgattt ctttcgcgct cgcatagggc aaatcaatag    3360
ggaaaagttc taattgcatt ttcctatcgc tccaatcaaa agaagtgata tctaacagca    3420
caggcgtatt agagtgtttt tgcaaacttt tagcgaaagc gtattgaaac atttgattcc    3480
caagccctcc gcaaatttgc accaccttaa aagccatatg tatatctcct tcttgaattc    3540
taaaaattga ttgaatgtat gcaaataaat gcatacacca taggtgtggt ttaatttgat    3600
gccctttttc agggctggaa tgtgtaagag cggggttatt tatgctgttg tttttttgtt    3660
actcgggaag ggcttacct cttccgcata aacgcttcca tcagcgttta tagttaaaaa    3720
aatctttcgg aactggtttt gcgcttaccc caaccaacag gggatttgct gctttccatt    3780
gagcctgttt ctctgcgcga cgttcgcggc ggcgtgtttg tgcatccatc tggattctcc    3840
tgtcagttag cttttggtggt gtgtggcagt tgtagtcctg aacgaaaacc ccccgcgatt    3900
ggcacattgg cagctaatcc ggaatcgcac ttacggccaa tgcttcgttt cgtatcacac    3960
accccaaagc cttctgcttt gaatgctgcc cttcttcagg gcttaatttt taagagcgtc    4020
accttcatgt tggtcagtgc gtcctgctga tgtgctcagt atcaccgcca gtggtattta    4080
tgtcaacacc gccagagata atttatcacc gcagatggtt atctgtatgt tttttatatg    4140
aatttatttt ttgcagggg gcattgttg gtaggtgaga gatcaattct gcattaatga    4200
atcggccaac gcgcggggag aggcggtttg cgtattgggc gctcttccgc ttcctcgctc    4260
actgactcgc tgcgctcggt cgttcggctg cggcgagcgg tatcagctca ctcaaaggcg    4320
gtaatacggt tatccacaga atcaggggat aacgcaggaa agaacatgtg agcaaaaggc    4380
cagcaaaagg ccaggaaccg taaaaaggcc gcgttgctgg cgtttttcca taggctccgc    4440 cccccctgacg agcatcacaa aaatcgacgc tcaagtcaga ggtggcgaaa cccgacagga    4500
ctataaagat accaggcgtt tccccctgga agctccctcg tgcgctctcc tgttccgacc    4560
```

```
ctgccgctta ccggatacct gtccgccttt ctcccttcgg gaagcgtggc gctttctcat    4620
agctcacgct gtaggtatct cagttcggtg taggtcgttc gctccaagct gggctgtgtg    4680
cacgaacccc ccgttcagcc cgaccgctgc gccttatccg gtaactatcg tcttgagtcc    4740
aacccggtaa gacacgactt atcgccactg gcagcagcca ctggtaacag gattagcaga    4800
gcgaggtatg taggcggtgc tacagagttc ttgaagtggt ggcctaacta cggctacact    4860
agaaggacag tatttggtat ctgcgctctg ctgaagccag ttaccttcgg aaaaagagtt    4920
ggtagctctt gatccggcaa acaaaccacc gctggtagcg tggtttttt tgtttgcaag    4980 cagcagatta cgcgcagaaa aaaggatct caagaagatc ctttgatctt ttctacgggg    5040
tctgacgctc agtggaacga aaactcacgt taagggattt tggtcatgag attatcaaaa    5100
aggatcttca cctagatcct tttaaattaa aaatgaagtt ttaaatcaat ctaaagtata    5160
tatgagtaaa cttggtctga cagttaccaa tgcttaatca gtgaggcacc tatctcagcg    5220
atctgtctat ttcgttcatc catagttgcc tgactccccg tcgtgtagat aactacgata    5280
cgggagggct taccatctgg ccccagtgct gcaatgatac cgcgagaccc acgctcaccg    5340
gctccagatt tatcagcaat aaaccagcca gccggaaggg ccgagcgcag aagtggtcct    5400
gcaactttat ccgcctccat ccagtctatt aattgttgcc gggaagctag agtaagtagt    5460
tcgccagtta atagtttgcg caacgttgtt gccattgcta caggcatcgt ggtgtcacgc    5520
tcgtcgtttg gtatggcttc attcagctcc ggttcccaac gatcaaggcg agttacatga    5580
tcccccatgt tgtgcaaaaa agcggttagc tccttcggtc ctccgatcgt tgtcagaagt    5640
aagttggccg cagtgttatc actcatggtt atggcagcac tgcataattc tcttactgtc    5700
atgccatccg taagatgctt ttctgtgact ggtgagtact caaccaagtc attctgagaa    5760
tagtgtatgc ggcgaccgag ttgctcttgc ccggcgtcaa tacgggataa taccgcgcca    5820
catagcagaa ctttaaaagt gctcatcatt ggaaaacgtt cttcggggcg aaaactctca    5880
aggatcttac cgctgttgag atccagttcg atgtaaccca ctcgtgcacc caactgatct    5940
tcagcatctt ttactttcac cagcgtttct gggtgagcaa aaacaggaag gcaaaatgcc    6000
gcaaaaaagg gaataagggc gacacggaaa tgttgaatac tcatactctt ccttttcaa    6060 tattattgaa gcatttatca gggttattgt ctcatgagcg gatacatatt tgaatgtatt    6120
tagaaaaata aacaaatagg ggttccgcgc acatttcccc gaaaagtgcc acctgacgtc    6180
taagaaacca ttattatcat gacattaacc tataaaaata ggcgtatcac gaggccttt     6240 cgtc                                                                6244
```

<210> SEQ ID NO 6
<211> LENGTH: 6216
<212> TYPE: DNA
<213> ORGANISM: Artificial Sequence
<220> FEATURE:
<223> OTHER INFORMATION: Sequence of pG180.

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
gattggttac ggcgcgtttc gcatcattgt tgagttttc gccagcccg acgcgcagtt      360
```

-continued

| | | | |
|---|---|---|---|
| taccggtgcc tgggtgcagt acatcagcat ggggcaaatt ctttccatcc cgatgattgt | 420 |
| cgcgggtgtg atcatgatgg tctgggcata tcgtcgcagc ccacagcaac acgtttcctg | 480 |
| aggaaccatg aaacagtatt tagaactgat gcaaaaagtg ctcgacgaag gcacacagaa | 540 |
| aaacgaccgt accggaaccg gaacgctttc cattttggt catcagatgc gttttaacct | 600 |
| gcaagatgga ttcccgctgg tgacaactaa acgttgccac ctgcgttcca tcatccatga | 660 |
| actgctgtgg tttctgcagg cgacactaa cattgcttat ctacacgaaa acaatgtcac | 720 |
| catctgggac gaatgggccg atgaaaacgg cgacctcggg ccagtgtatg gtaaacagtg | 780 |
| gcgcgcctgg ccaacgccag atggtcgtca tattgaccag atcactacgg tactgaacca | 840 |
| gctgaaaaac gacccggatt cgcgccgcat tattgtttca gcgtggaacg taggcgaact | 900 |
| ggataaaatg gcgctggcac cgtgccatgc attcttccag ttctatgtgg cagacggcaa | 960 |
| actctcttgc cagctttatc agcgctcctg tgacgtcttc ctcggcctgc cgttcaacat | 1020 |
| tgccagctac gcgttattgg tgcatatgat ggcgcagcag tgcgatctgg aagtgggtga | 1080 |
| ttttgtctgg accggtggcg acacgcatct gtacagcaac catatggatc aaactcatct | 1140 |
| gcaattaagc cgcgaaccgc gtccgctgcc gaagttgatt atcaaacgta acccgaatc | 1200 |
| catcttcgac taccgtttcg aagactttga gattgaaggc tacgatccgc atccgggcat | 1260 |
| taaagcgccg gtggctatct aattacgaaa catcctgcca gagccgacgc cagtgtgcgt | 1320 |
| cggtttttt accctccgtt aaattcttcg agacgccttc ccgaaggcgc cattcgccat | 1380 |
| tcaggctgcg caactgttgg aagggcgat cggtgcgggc ctcttcgcta ttacgccagc | 1440 |
| tggcgaaagg gggatgtgct gcaaggcgat taagttgggt aacgccaggg ttttcccagt | 1500 |
| cacgacgttg taaaacgacg gccagtgcca agctttcttt aatgaagcag gcatcagga | 1560 |
| cggtatcttt gtggagaaag cagagtaatc ttattcagcc tgactggtgg gaaaccacca | 1620 |
| gtcagaatgt gttagcgcat gttgacaaaa ataccattag tcacattatc cgtcagtcgg | 1680 |
| acgacatggt agataacctg tttattatgc gttttgatct tacgtttaat attaccttta | 1740 |
| tgcgatgaaa cggtcttggc tttgatattc atttggtcag agatttgaat ggttccctga | 1800 |
| cctgccatcc acattcgcaa catactcgat tcggttcggc tcaatgataa cgtcggcata | 1860 |
| tttaaaaacg aggttatcgt tgtctctttt ttcagaatat cgccaaggat atcgtcgaga | 1920 |
| gattccggtt taatcgattt agaactgatc aataaatttt ttctgaccaa tagatattca | 1980 |
| tcaaaatgaa cattggcaat tgccataaaa acgataaata acgtattggg atgttgatta | 2040 |
| atgatgagct tgatacgctg actgttagaa gcatcgtgga tgaaacagtc ctcattaata | 2100 |
| aacaccactg aagggcgctg tgaatcacaa gctatggcaa ggtcatcaac ggtttcaatg | 2160 |
| tcgttgattt ctctttttt aacccctcta ctcaacagat accggttaa acctagtcgg | 2220 |
| gtgtaactac ataaatccat aataatcgtt gacatggcat accctcactc aatgcgtaac | 2280 |
| gataattccc cttacctgaa tatttcatca tgactaaacg gaacaacatg ggtcacctaa | 2340 |
| tgcgccactc tcgcgatttt tcaggcggac ttactatccc gtaaagtgtt gtataatttg | 2400 |
| cctggaattg tcttaaagta aagtaaatgt tgcgatatgt gagtgagctt aaaacaaata | 2460 |
| tttcgctgca ggagtatcct ggaagatgtt cgtagaagct tactgctcac aagaaaaaag | 2520 |
| gcacgtcatc tgacgtgcct ttttatttg tactaccctg tacgattact gcagctcgag | 2580 |
| tttaattcaa atcttcttca gaaatcaatt tttgttctct tacattcaat ttaaaccaag | 2640 |
| attctggtac agaatcctta tttataaaat tacctggagc aatcaccagc ttatcatcat | 2700 |

-continued

```
atttcgaaag ccatgctccc caccagtaaa aagagctatt cgatattata taattacgaa    2760
aatgcatcat tagaaacata tcatctatag taccactatc atcctccttt ttacttatca    2820
aacgaacagg atattttccc gctagatgtt tttcaaccca ttctaaatct tgtgaaaaac    2880
aaaagaaaac aggagaagta acttttgatg ccatatatc catagcacat ttatagtaat     2940
catcttctaa cactccacca ggagctacat cactttcctg ataccgtcta accccaatca    3000
ttatggcatt cttatctagc aattttattt cttccaattc caaatacgat gtgtattcta    3060
attttttttg tattacaaag tcctcttta tctcttgttt ataatcaaga aaatatttt      3120 ctgactgcca atatccttcc agaaaagcat ttgtaatctt agaactaatt aaccttgatt    3180
caaagtgggg agggcgctct tcgcaaatat aacgatatga tggatgaagt atatgacaac    3240
ctaaattacg acttagcctt ctataataat tcccatatga aaatcaaat gttaattttt     3300 tattttcagg caagtctaat gcaaaatatg ataataaaag tttccttta taaacttcat     3360 catttgcaaa atcagtagtc aaattaaaag cgaatggtac attgtttctt aatgccatgg    3420
ccttcaccat agcgtaaata aacatttgat tccccaatcc tcctcgcaaa gatgatacaa    3480
tcatatgtat atctccttct tgtctagaat tctaaaaatt gattgaatgt atgcaaataa    3540
atgcatacac cataggtgtg gtttaatttg atgccctttt tcagggctgg aatgtgtaag    3600
agcggggtta tttatgctgt tgttttttg ttactcggga agggctttac ctcttccgca     3660
taaacgcttc catcagcgtt tatagttaaa aaatctttc ggaactggtt ttgcgcttac     3720
cccaaccaac aggggatttg ctgctttcca ttgagcctgt ttctctgcgc gacgttcgcg    3780
gcggcgtgtt tgtgcatcca tctggattct cctgtcagtt agctttggtg gtgtgtggca    3840
gttgtagtcc tgaacgaaaa ccccccgcga ttggcacatt ggcagctaat ccggaatcgc    3900
acttacggcc aatgcttcgt ttcgtatcac acaccccaaa gccttctgct ttgaatgctg    3960
cccttcttca gggcttaatt tttaagagcg tcaccttcat ggtggtcagt gcgtcctgct    4020
gatgtgctca gtatcaccgc cagtggtatt tatgtcaaca ccgccagaga taatttatca    4080
ccgcagatgg ttatctgtat gttttttata tgaatttatt ttttgcaggg gggcattgtt    4140
tggtaggtga gagatcaatt ctgcattaat gaatcggcca acgcgcgggg agaggcggtt    4200
tgcgtattgg gcgctcttcc gcttcctcgc tcactgactc gctgcgctcg tcgttcggc     4260 tgcggcgagc ggtatcagct cactcaaagg cggtaatacg ttatccaca gaatcagggg     4320 ataacgcagg aaagaacatg tgagcaaaag gccagcaaaa ggccaggaac cgtaaaaagg    4380
ccgcgttgct ggcgtttttc cataggctcc gcccccctga cgagcatcac aaaaatcgac    4440
gctcaagtca gaggtggcga aacccgacag gactataaag ataccaggcg tttccccctg    4500
gaagctccct cgtgcgctct cctgttccga ccctgccgct taccggatac ctgtccgcct    4560
ttctcccttc gggaagcgtg gcgctttctc atagctcacg ctgtaggtat ctcagttcgg    4620
tgtaggtcgt tcgctccaag ctgggctgtg tgcacgaacc ccccgttcag cccgaccgct    4680
gcgccttatc cggtaactat cgtcttgagt ccaacccggt aagacacgac ttatcgccac    4740
tggcagcagc cactggtaac aggattagca gagcgaggta tgtaggcggt gctacagagt    4800
tcttgaagtg gtggcctaac tacggctaca ctagaaggac agtatttggt atctgcgctc    4860
tgctgaagcc agttaccttc ggaaaaagag ttggtagctc ttgatccggc aaacaaacca    4920
ccgctggtag cggtggtttt tttgtttgca agcagcagat tacgcgcaga aaaaaggat    4980 ctcaagaaga tcctttgatc ttttctacgg ggtctgacgc tcagtggaac gaaaactcac    5040
gttaagggat tttggtcatg agattatcaa aaaggatctt cacctagatc cttttaaatt    5100
```

| | | | | |
|---|---|---|---|---|
| aaaaatgaag | ttttaaatca | atctaaagta | tatatgagta | aacttggtct gacagttacc | 5160 |
| aatgcttaat | cagtgaggca | cctatctcag | cgatctgtct | atttcgttca tccatagttg | 5220 |
| cctgactccc | cgtcgtgtag | ataactacga | tacgggaggg | cttaccatct ggccccagtg | 5280 |
| ctgcaatgat | accgcgagac | ccacgctcac | cggctccaga | tttatcagca ataaaccagc | 5340 |
| cagccggaag | ggccgagcgc | agaagtggtc | ctgcaacttt | atccgcctcc atccagtcta | 5400 |
| ttaattgttg | ccgggaagct | agagtaagta | gttcgccagt | taatagtttg cgcaacgttg | 5460 |
| ttgccattgc | tacaggcatc | gtggtgtcac | gctcgtcgtt | tggtatggct tcattcagct | 5520 |
| ccggttccca | acgatcaagg | cgagttacat | gatcccccat | gttgtgcaaa aaagcggtta | 5580 |
| gctccttcgg | tcctccgatc | gttgtcagaa | gtaagttggc | cgcagtgtta tcactcatgg | 5640 |
| ttatggcagc | actgcataat | tctcttactg | tcatgccatc | cgtaagatgc ttttctgtga | 5700 |
| ctggtgagta | ctcaaccaag | tcattctgag | aatagtgtat | gcggcgaccg agttgctctt | 5760 |
| gcccggcgtc | aatacgggat | aataccgcgc | cacatagcag | aactttaaaa gtgctcatca | 5820 |
| ttggaaaacg | ttcttcgggg | cgaaaactct | caaggatctt | accgctgttg agatccagtt | 5880 |
| cgatgtaacc | cactcgtgca | cccaactgat | cttcagcatc | ttttactttc accagcgttt | 5940 |
| ctgggtgagc | aaaaacagga | aggcaaaatg | ccgcaaaaaa | gggaataagg gcgacacgga | 6000 |
| aatgttgaat | actcatactc | ttcctttttc | aatattattg | aagcatttat cagggttatt | 6060 |
| gtctcatgag | cggatacata | tttgaatgta | tttagaaaaa | taaacaaata ggggttccgc | 6120 |
| gcacatttcc | ccgaaaagtg | ccacctgacg | tctaagaaac | cattattatc atgacattaa | 6180 |
| cctataaaaa | taggcgtatc | acgaggccct | ttcgtc | | 6216 |

<210> SEQ ID NO 7
<211> LENGTH: 5049
<212> TYPE: DNA
<213> ORGANISM: Escherichia coli

<400> SEQUENCE: 7

| | | | | |
|---|---|---|---|---|
| gtccatggaa | gacgtcgaaa | aagtggttat | cgacgagtcg | gtaattgatg gtcaaagcaa | 60 |
| accgttgctg | atttatggca | agccggaagc | gcaacaggca | tctggtgaat aattaaccat | 120 |
| tcccatacaa | ttagttaacc | aaaaaggggg | gattttatct | cccctttaat ttttcctcta | 180 |
| ttctcggcgt | tgaatgtggg | ggaaacatcc | ccatatactg | acgtacatgt taatagatgg | 240 |
| cgtgaagcac | agtcgtgtca | tctgattacc | tggcggaaat | taaactaaga gagagctcta | 300 |
| tgattccggg | gatccgtcga | cctgcagttc | gaagttccta | ttctctagaa agtataggaa | 360 |
| cttcagagcg | cttttgaagc | tcacgctgcc | gcaagcactc | agggcgcaag gctgctaaa | 420 |
| ggaagcggaa | cacgtagaaa | gccagtccgc | agaaacggtg | ctgaccccgg atgaatgtca | 480 |
| gctactgggc | tatctggaca | agggaaaacg | caagcgcaaa | gagaaagcag gtagcttgca | 540 |
| gtgggcttac | atggcgatag | ctagactggg | cggttttatg | gacagcaagc gaaccggaat | 600 |
| tgccagctgg | ggcgccctct | ggtaaggttg | gaagccctg | caaagtaaac tggatggctt | 660 |
| tcttgccgcc | aaggatctga | tggcgcaggg | gatcaagatc | tgatcaagag acaggatgag | 720 |
| gatcgtttcg | catgattgaa | caagatggat | tgcacgcagg | ttctccggcc gcttgggtgg | 780 |
| agaggctatt | cggctatgac | tgggcacaac | agacaatcgg | ctgctctgat gccgccgtgt | 840 |
| tccgctgtc | agcgcagggg | cgcccggttc | ttttgtcaa | gaccgacctg tccggtgccc | 900 |
| tgaatgaact | gcaggacgag | gcagcgcggc | tatcgtggct | ggccacgacg ggcgttcctt | 960 |

```
gcgcagctgt gctcgacgtt gtcactgaag cgggaaggga ctggctgcta ttgggcgaag    1020
tgccggggca ggatctcctg tcatctcacc ttgctcctgc cgagaaagta tccatcatgg    1080
ctgatgcaat gcggcggctg catacgcttg atccggctac ctgcccattc gaccaccaag    1140
cgaaacatcg catcgagcga gcacgtactc ggatggaagc cggtcttgtc gatcaggatg    1200
atctggacga agagcatcag gggctcgcgc cagccgaact gttcgccagg ctcaaggcgc    1260
gcatgcccga cggcgaggat ctcgtcgtga cccatggcga tgcctgcttg ccgaatatca    1320
tggtggaaaa tggccgcttt tctggattca tcgactgtgg ccggctgggt gtggcggacc    1380
gctatcagga catagcgttg gctacccgtg atattgctga agagcttggc ggcgaatggg    1440
ctgaccgctt cctcgtgctt tacggtatcg ccgctcccga ttcgcagcgc atcgccttct    1500
atcgccttct tgacgagttc ttctaataag gggatcttga agttcctatt ccgaagttcc    1560
tattctctag aaagtatagg aacttcgaag cagctccagc ctacataaag cggccgctta    1620
tttttgacac cagaccaact ggtaatggta gcgaccggcg ctcagctgga attccgccga    1680
tactgacggg ctccaggagt cgtcgccacc aatccccata tggaaaccgt cgatattcag    1740
ccatgtgcct tcttccgcgt gcagcagatg gcgatggctg gtttccatca gttgctgttg    1800
actgtagcgg ctgatgttga actggaagtc gccgcgccac tggtgtgggc cataattcaa    1860
ttcgcgcgtc ccgcagcgca gaccgttttc gctcgggaag acgtacgggg tatacatgtc    1920
tgacaatggc agatcccagc ggtcaaaaca ggcggcagta aggcggtcgg gatagttttc    1980
ttgcggccct aatccgagcc agtttacccg ctctgctacc tgcgccagct ggcagttcag    2040
gccaatccgc gccggatgcg tgtatcgct cgccacttca acatcaacgg taatcgccat    2100
ttgaccacta ccatcaatcc ggtaggtttt ccggctgata aataaggttt tccctgatg    2160 ctgccacgcg tgagcggtcg taatcagcac cgcatcagca agtgtatctg ccgtgcactg    2220
caacaacgct gcttcggcct ggtaatggcc cgccgccttc cagcgttcga cccaggcgtt    2280
agggtcaatg cgggtcgctt cacttacgcc aatgtcgtta tccagcggtg cacgggtgaa    2340
ctgatcgcgc agcggcgtca gcagttgttt tttatcgcca atccacatct gtgaaagaaa    2400
gcctgactgg cggttaaatt gccaacgctt attacccagc tcgatgcaaa aatccatttc    2460
gctggtggtc agatgcggga tggcgtggga cgcggcgggg agcgtcacac tgaggttttc    2520
cgccagacgc cactgctgcc aggcgctgat gtgcccggct tctgaccatg cggtcgcgtt    2580
cggttgcact acgcgtactg tgagccagag ttgcccggcg ctctccggct gcggtagttc    2640
aggcagttca atcaactgtt taccttgtgg agcgacatcc agaggcactt caccgcttgc    2700
cagcggctta ccatccagcg ccaccatcca gtgcaggagc tcgttatcgc tatgacggaa    2760
caggtattcg ctggtcactt cgatggtttg cccggataaa cggaactgga aaaactgctg    2820
ctggtgtttt gcttccgtca gcgctggatg cggcgtgcgg tcggcaaaga ccagaccgtt    2880
catacagaac tggcgatcgt tcggcgtatc gccaaaatca ccgccgtaag ccgaccacgg    2940
gttgccgttt tcatcatatt taatcagcga ctgatccacc cagtcccaga cgaagccgcc    3000
ctgtaaacgg ggatactgac gaaacgcctg ccagtattta gcgaaaccgc caagactgtt    3060
acccatcgcg tgggcgtatt cgcaaaggat cagcgggcgc gtctctccag gtagcgaaag    3120 ccatttttg atggaccatt tcggcacagc cgggaagggc tggtcttcat ccacgcgcgc    3180
gtacatcggg caaataatat cggtggccgt ggtgtcggct ccgccgcctt catactgcac    3240
cgggcgggaa ggatcgacag atttgatcca gcgatacagc gcgtcgtgat tagcgccgtg    3300
gcctgattca ttccccagcg accagatgat cacactcggg tgattacgat cgcgctgcac    3360
```

```
cattcgcgtt acgcgttcgc tcatcgccgg tagccagcgc ggatcatcgg tcagacgatt    3420
cattggcacc atgccgtggg tttcaatatt ggcttcatcc accacataca ggccgtagcg    3480
gtcgcacagc gtgtaccaca gcggatggtt cggataatgc gaacagcgca cggcgttaaa    3540
gttgttctgc ttcatcagca ggatatcctg caccatcgtc tgctcatcca tgacctgacc    3600
atgcagagga tgatgctcgt gacggttaac gcctcgaatc agcaacggct gccgttcag     3660 cagcagcaga ccattttcaa tccgcacctc gcggaaaccg acatcgcagg cttctgcttc    3720
aatcagcgtg ccgtcggcgg tgtgcagttc aaccaccgca cgatagagat cgggatttc     3780 ggcgctccac agtttcgggt tttcgacgtt cagacgtagt gtgacgcgat cggcataacc    3840
accacgctca tcgataattt caccgccgaa aggcgcggtg ccgctggcga cctgcgtttc    3900
accctgccat aaagaaactg ttacccgtag gtagtcacgc aactcgccgc acatctgaac    3960
ttcagcctcc agtacagcgc ggctgaaatc atcattaaag cgagtggcaa catggaaatc    4020
gctgatttgt gtagtcggtt tatgcagcaa cgagacgtca cggaaaatgc cgctcatccg    4080
ccacatatcc tgatcttcca gataactgcc gtcactccag cgcagcacca tcaccgcgag    4140
gcggttttct ccggcgcgta aaaatgcgct caggtcaaat tcagacggca aacgactgtc    4200
ctggccgtaa ccgacccagc gcccgttgca ccacagatga aacgccgagt taacgccatc    4260
aaaaataatt cgcgtctggc cttcctgtag ccagctttca tcaacattaa atgtgagcga    4320
gtaacaaccc gtcggattct ccgtgggaac aaacggcgga ttgaccgtaa tgggataggt    4380
cacgttggtg tagatgggcg catcgtaacc gtgcatctgc cagtttgagg ggacgacgac    4440
agtatcggcc tcaggaagat cgcactccag ccagctttcc ggcaccgctt ctggtgccgg    4500
aaaccaggca aagcgccatt cgccattcag gctgcgcaac tgttgggaag ggcgatcggt    4560
gcgggcctct tcgctattac gccagctggc gaaaggggga tgtgctgcaa ggcgattaag    4620
ttgggtaacg ccagggtttt cccagtcacg acgttgtaaa acgacggcca gtgaatccgt    4680
aatcatggtc atagtaggtt tcctcaggtt gtgactgcaa aatagtgacc tcgcgcaaaa    4740
tgcactaata aaaacagggc tggcaggcta attcgggctt gccagccttt ttttgtctcg    4800
ctaagttaga tggcggatcg ggcttgccct tattaagggg tgttgtaagg ggatggctgg    4860
cctgatataa ctgctgcgcg ttcgtacctt gaaggattca agtgcgatat aaattataaa    4920
gaggaagaga agagtgaata atctcaatt gatcgacaag attgctgcag gggctgatat    4980
ctctaaagct gcggctggcc gtgcgttaga tgctattatt gcttccgtaa ctgaatctct    5040
gaaagaagg                                                            5049

<210> SEQ ID NO 8
<211> LENGTH: 6917
<212> TYPE: DNA
<213> ORGANISM: Artificial Sequence
<220> FEATURE:
<223> OTHER INFORMATION: Sequence of pG186.

<400> SEQUENCE: 8
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg      120
ttggcgggtg tcggggctgg cttaactatg cggcatcaga gcagattgta ctgagagtgc     180
accatatatg cggtgtgaaa taccgcacag atgcgtaagg agaaaatacc gcatcaggcg     240
cctcctcaac ctgtatattc gtaaaccacg cccaatggga gctgtctcag gtttgttcct     300
```

```
gattggttac ggcgcgtttc gcatcattgt tgagtttttc cgccagcccg acgcgcagtt       360
taccggtgcc tgggtgcagt acatcagcat ggggcaaatt ctttccatcc cgatgattgt       420
cgcgggtgtg atcatgatgg tctgggcata tcgtcgcagc ccacagcaac acgtttcctg       480
aggaaccatg aaacagtatt tagaactgat gcaaaaagtg ctcgacgaag cacacagaa        540 aaacgaccgt accggaaccg gaacgctttc cattttggt catcagatgc gttttaacct        600
gcaagatgga ttcccgctgg tgacaactaa acgttgccac ctgcgttcca tcatccatga       660
actgctgtgg tttctgcagg gcgacactaa cattgcttat ctacacgaaa acaatgtcac       720
catctgggac gaatgggccg atgaaaacgg cgacctcggg ccagtgtatg gtaaacagtg       780
gcgcgcctgg ccaacgccag atggtcgtca tattgaccag atcactacgg tactgaacca       840
gctgaaaaac gacccggatt cgcgccgcat tattgtttca gcgtggaacg taggcgaact       900
ggataaaatg gcgctggcac cgtgccatgc attcttccag ttctatgtgg cagacggcaa       960
actctcttgc cagctttatc agcgctcctg tgacgtcttc ctcggcctgc cgttcaacat      1020
tgccagctac gcgttattgg tgcatatgat ggcgcagcga tgcgatctgg aagtgggtga      1080
ttttgtctgg accggtggcg acacgcatct gtacagcaac catatggatc aaactcatct      1140
gcaattaagc cgcgaaccgc gtccgctgcc gaagttgatt atcaaacgta aacccgaatc      1200
catcttcgac taccgtttcg aagactttga gattgaaggc tacgatccgc atccgggcat      1260
taaagcgccg gtggctatct aattacgaaa catcctgcca gagccgacgc cagtgtgcgt      1320 cggtttttt ccctccgtt aaattcttcg agacgccttc ccgaaggcgc cattcgccat        1380
tcaggctgcg caactgttgg gaagggcgat cggtgcgggc ctcttcgcta ttacgccagc      1440
tggcgaaagg gggatgtgct gcaaggcgat taagttgggt aacgccaggg ttttcccagt      1500
cacgacgttg taaaacgacg gccagtgcca agctttcttt aatgaagcag ggcatcagga      1560
cggtatcttt gtggagaaag cagagtaatc ttattcagcc tgactggtgg gaaaccacca      1620
gtcagaatgt gttagcgcat gttgacaaaa ataccattag tcacattatc cgtcagtcgg      1680
acgacatggt agataaccctg tttattatgc gttttgatct tacgtttaat attacctta     1740 tgcgatgaaa cggtcttggc tttgatattc atttggtcag agatttgaat ggttccctga      1800
cctgccatcc acattcgcaa catactcgat tcggttcggc tcaatgataa cgtcggcata      1860
tttaaaaacg aggttatcgt tgtctctttt ttcagaatat cgccaaggat atcgtcgaga      1920
gattccggtt taatcgattt agaactgatc aataaatttt ttctgaccaa tagatattca      1980
tcaaaatgaa cattggcaat tgccataaaa acgataaata acgtattggg atgttgatta      2040
atgatgagct tgatacgctg actgttagaa gcatcgtgga tgaaacagtc ctcattaata      2100
aacaccactg aagggcgctg tgaatcacaa gctatggcaa ggtcatcaac ggtttcaatg      2160
tcgttgattt ctctttttt aacccctcta ctcaacagat accggttaa acctagtcgg        2220 gtgtaactac ataatccat aataatcgtt gacatggcat accctcactc aatgcgtaac       2280
gataattccc cttacctgaa tatttcatca tgactaaacg gaacaacatg ggtcacctaa      2340
tgcgccactc tcgcgatttt tcaggcggac ttactatccc gtaaagtgtt gtataattg      2400 cctggaattg tcttaaagta aagtaaatgt tgcgatatgt gagtgagctt aaaacaaata      2460
tttcgctgca ggagtatcct ggaagatgtt cgtagaagct tactgctcac aagaaaaaag      2520
gcacgtcatc tgacgtgcct ttttatttg tactaccctg tacgattact gcagctcgag       2580 ttagtctta tctgccggac ttaaggtcac tgaagagaga taattcagca gggcgatatc       2640
gttctcgaca cccagcttca tcatcgcaga tttcttctgg ctactgatgg ttttaatact      2700
```

```
gcggttcagc tttttagcga tctcggtcac caggaagcct tccgcaaaca ggcgcagaac    2760
ttcactctct tttggcgaga gacgcttgtc accgtaacca ccagcactga ttttttccaa    2820
caggcgagaa acgctttccg gggtaaattt cttcccttt c tgcagcgcgg cgagagcttt    2880
cggcagatcg gtcggtgcac cttgtttcag cacgatccct tcgatatcca gatccaatac    2940
cgcactaaga atcgccgggt tgttgttcat agtcagaaca atgatcgaca ggcttgggaa    3000
atggcgcttg atgtacttga ttaaggtaat gccatcgccg tacttatcgc caggcatgga    3060
gagatcggta atcaacacat gcgcatccag tttcggcagg ttgttgatca gtgctgtaga    3120
gtcttcaaat tcgccgacaa cattcaccca ctcaatttgc tcaagtgatt tgcgaatacc    3180
gaacaagact atcggatggt catcggcaat aattacgttc atattgttca ttgtatatct    3240
ccttcttctc gagtttaatt caaatcttct tcagaaatca atttttgttc agcgttatac    3300
ttttgggatt ttacctcaaa atgggattct attttcaccc actccttaca aaggatattc    3360
tcatgcccaa aaagccagtg tttggggcca ataatgattt tttctggatt ttctatcaaa    3420
taggccgccc accagctata agtgctatta gcgataatgc catgctgaca agattgcatg    3480
agcagcatgt cccaatacgc ctcttcttct ttatccctag tggtcatgtc cataaaaggg    3540
tagccaagat caagattttg cgtgaattct aagtcttcgc aaaacacaaa aagctccatg    3600
tttggcacgc gctttgccat atactcaagc gcctttttt t gatagtcaat accaagctga    3660
cagccaatcc ccacataatc ccctcttctt atatgcacaa acacgctgtt tttagcggct    3720
aaaatcaaag aaagcttgca ctgatattct tcctcttttt tattattatt cttattattt    3780
tcgggtggtg gtggtagagt gaaggtttgc ttgattaaag gggatatagc atcaaagtat    3840
cgtggatctt ggaaatagcc aaaaaaataa gtcaagcggc ttggctttag caatttaggc    3900
tcgtattcaa aaacgatttc ttgactcacc ctatcaaatc ccatgcattt gagcgcgtct    3960
cttactagct tggggaggtg ttgcatttta gctatagcga tttctttcgc gctcgcatag    4020
ggcaaatcaa tagggaaaag ttctaattgc attttcctat cgctccaatc aaaagaagtg    4080
atatctaaca gcacaggcgt attagagtgt ttttgcaaac ttttagcgaa agcgtattga    4140
aacatttgat tcccaagccc tccgcaaatt tgcaccacct taaaagccat atgtatatct    4200
ccttcttgaa ttctaaaaat tgattgaatg tatgcaaata aatgcataca ccataggtgt    4260
ggtttaattt gatgccsttt ttcagggctg aatgtgtaa gagcggggtt atttatgctg    4320 ttgtttttt gttactcggg aagggcttta cctcttccgc ataaacgctt ccatcagcgt    4380
ttatagttaa aaaaatcttt cggaactggt tttgcgctta ccccaaccaa caggggattt    4440
gctgctttcc attgagcctg tttctctgcg cgacgttcgc ggcggcgtgt ttgtgcatcc    4500
atctggattc tcctgtcagt tagctttggt ggtgtgtggc agttgtagtc ctgaacgaaa    4560
accccccgcg attggcacat tggcagctaa tccggaatcg cacttacggc caatgcttcg    4620
tttcgtatca cacaccccaa agccttctgc tttgaatgct gcccttcttc agggcttaat    4680
ttttaagagc gtcaccttca tggtggtcag tgcgtcctgc tgatgtgctc agtatcaccg    4740
ccagtggtat ttatgtcaac accgccagag ataatttatc accgcagatg gttatctgta    4800
tgttttttat atgaatttat ttttttgcagg ggggcattgt ttggtaggtg agagatcaat    4860
tctgcattaa tgaatcggcc aacgcgcggg gagaggcggt ttgcgtattg ggcgctcttc    4920
cgcttcctcg ctcactgact cgctgcgctc ggtcgttcgg ctgcggcgag cggtatcagc    4980
tcactcaaag gcggtaatac ggttatccac agaatcaggg gataacgcag gaaagaacat    5040
```

```
gtgagcaaaa ggccagcaaa aggccaggaa ccgtaaaaag gccgcgttgc tggcgttttt     5100
ccataggctc cgccccctg acgagcatca caaaaatcga cgctcaagtc agaggtggcg      5160
aaacccgaca ggactataaa gataccaggc gtttccccct ggaagctccc tcgtgcgctc     5220
tcctgttccg accctgccgc ttaccggata cctgtccgcc tttctccctt cgggaagcgt     5280
ggcgctttct catagctcac gctgtaggta tctcagttcg gtgtaggtcg ttcgctccaa     5340
gctgggctgt gtgcacgaac cccccgttca gcccgaccgc tgcgccttat ccggtaacta     5400
tcgtcttgag tccaacccgg taagacacga cttatcgcca ctggcagcag ccactggtaa     5460
caggattagc agagcgaggt atgtaggcgg tgctacagag ttcttgaagt ggtggcctaa     5520
ctacggctac actagaagga cagtatttgg tatctgcgct ctgctgaagc cagttacctt     5580
cggaaaaaga gttggtagct cttgatccgg caaacaaacc accgctggta gcggtggttt     5640
ttttgtttgc aagcagcaga ttacgcgcag aaaaaaagga tctcaagaag atcctttgat     5700
cttttctacg gggtctgacg ctcagtggaa cgaaaactca cgttaaggga ttttggtcat     5760
gagattatca aaaaggatct tcacctagat ccttttaaat taaaaatgaa gttttaaatc     5820
aatctaaagt atatatgagt aaacttggtc tgacagttac caatgcttaa tcagtgaggc     5880
acctatctca gcgatctgtc tatttcgttc atccatagtt gcctgactcc ccgtcgtgta     5940
gataactacg atacgggagg gcttaccatc tggccccagt gctgcaatga taccgcgaga     6000
cccacgctca ccggctccag atttatcagc aataaaccag ccagccggaa gggccgagcg     6060
cagaagtggt cctgcaactt tatccgcctc catccagtct attaattgtt gccgggaagc     6120
tagagtaagt agttcgccag ttaatagttt gcgcaacgtt gttgccattg ctacaggcat     6180
cgtggtgtca cgctcgtcgt ttggtatggc ttcattcagc tccggttccc aacgatcaag     6240
gcgagttaca tgatccccca tgttgtgcaa aaaagcggtt agctccttcg gtcctccgat     6300
cgttgtcaga agtaagttgg ccgcagtgtt atcactcatg gttatggcag cactgcataa     6360
ttctcttact gtcatgccat ccgtaagatg cttttctgtg actggtgagt actcaaccaa     6420
gtcattctga gaatagtgta tgcggcgacc gagttgctct tgcccggcgt caatacggga     6480
taataccgcg ccacatagca gaactttaaa agtgctcatc attggaaaac gttcttcggg     6540
gcgaaaactc tcaaggatct taccgctgtt gagatccagt tcgatgtaac ccactcgtgc     6600
acccaactga tcttcagcat cttttacttt caccagcgtt tctgggtgag caaaaacagg     6660
aaggcaaaat gccgcaaaaa agggaataag ggcgacacgg aaatgttgaa tactcatact     6720
cttcctttt caatattatt gaagcattta tcagggttat tgtctcatga gcggatacat     6780
atttgaatgt atttagaaaa ataaacaaat agggggttccg cgcacatttc cccgaaaagt     6840
gccacctgac gtctaagaaa ccattattat catgacatta acctataaaa ataggcgtat     6900
cacgaggccc tttcgtc                                                    6917
```

<210> SEQ ID NO 9
<211> LENGTH: 424
<212> TYPE: PRT
<213> ORGANISM: Escherichia coli

<400> SEQUENCE: 9

Met Thr Asp Lys Arg Lys Asp Gly Ser Gly Lys Leu Leu Tyr Cys Ser
1               5                   10                  15

Phe Cys Gly Lys Ser Gln His Glu Val Arg Lys Leu Ile Ala Gly Pro
            20                  25                  30

Ser Val Tyr Ile Cys Asp Glu Cys Val Asp Leu Cys Asn Asp Ile Ile

```
            35                  40                  45
Arg Glu Glu Ile Lys Glu Val Ala Pro His Arg Glu Arg Ser Ala Leu
 50                  55                  60

Pro Thr Pro His Glu Ile Arg Asn His Leu Asp Asp Tyr Val Ile Gly
 65                  70                  75                  80

Gln Glu Gln Ala Lys Val Leu Ala Val Ala Val Tyr Asn His Tyr
                 85                  90                  95

Lys Arg Leu Arg Asn Gly Asp Thr Ser Asn Gly Val Glu Leu Gly Lys
                100                 105                 110

Ser Asn Ile Leu Leu Ile Gly Pro Thr Gly Ser Gly Lys Thr Leu Leu
                115                 120                 125

Ala Glu Thr Leu Ala Arg Leu Leu Asp Val Pro Phe Thr Met Ala Asp
            130                 135                 140

Ala Thr Thr Leu Thr Glu Ala Gly Tyr Val Gly Glu Asp Val Glu Asn
145                 150                 155                 160

Ile Ile Gln Lys Leu Leu Gln Lys Cys Asp Tyr Asp Val Gln Lys Ala
                165                 170                 175

Gln Arg Gly Ile Val Tyr Ile Asp Glu Ile Asp Lys Ile Ser Arg Lys
            180                 185                 190

Ser Asp Asn Pro Ser Ile Thr Arg Asp Val Ser Gly Glu Gly Val Gln
        195                 200                 205

Gln Ala Leu Leu Lys Leu Ile Glu Gly Thr Val Ala Ala Val Pro Pro
    210                 215                 220

Gln Gly Gly Arg Lys His Pro Gln Gln Glu Phe Leu Gln Val Asp Thr
225                 230                 235                 240

Ser Lys Ile Leu Phe Ile Cys Gly Gly Ala Phe Ala Gly Leu Asp Lys
                245                 250                 255

Val Ile Ser His Arg Val Glu Thr Gly Ser Gly Ile Gly Phe Gly Ala
            260                 265                 270

Thr Val Lys Ala Lys Ser Asp Lys Ala Ser Glu Gly Glu Leu Leu Ala
        275                 280                 285

Gln Val Glu Pro Glu Asp Leu Ile Lys Phe Gly Leu Ile Pro Glu Phe
    290                 295                 300

Ile Gly Arg Leu Pro Val Val Ala Thr Leu Asn Glu Leu Ser Glu Glu
305                 310                 315                 320

Ala Leu Ile Gln Ile Leu Lys Glu Pro Lys Asn Ala Leu Thr Lys Gln
                325                 330                 335

Tyr Gln Ala Leu Phe Asn Leu Gly Val Asp Leu Glu Phe Arg Asp
            340                 345                 350

Glu Ala Leu Asp Ala Ile Ala Lys Lys Ala Met Ala Arg Lys Thr Gly
        355                 360                 365

Ala Arg Gly Leu Arg Ser Ile Val Glu Ala Ala Leu Leu Asp Thr Met
    370                 375                 380

Tyr Asp Leu Pro Ser Met Glu Asp Val Glu Lys Val Val Ile Asp Glu
385                 390                 395                 400

Ser Val Ile Asp Gly Gln Ser Lys Pro Leu Leu Ile Tyr Gly Lys Pro
                405                 410                 415

Glu Ala Gln Gln Ala Ser Gly Glu
            420

<210> SEQ ID NO 10
<211> LENGTH: 784
<212> TYPE: PRT
<213> ORGANISM: Escherichia coli
```

<400> SEQUENCE: 10

```
Met Asn Pro Glu Arg Ser Glu Arg Ile Glu Ile Pro Val Leu Pro Leu
1               5                   10                  15

Arg Asp Val Val Val Tyr Pro His Met Val Ile Pro Leu Phe Val Gly
            20                  25                  30

Arg Glu Lys Ser Ile Arg Cys Leu Glu Ala Ala Met Asp His Asp Lys
        35                  40                  45

Lys Ile Met Leu Val Ala Gln Lys Glu Ala Ser Thr Asp Glu Pro Gly
    50                  55                  60

Val Asn Asp Leu Phe Thr Val Gly Thr Val Ala Ser Ile Leu Gln Met
65                  70                  75                  80

Leu Lys Leu Pro Asp Gly Thr Val Lys Val Leu Val Glu Gly Leu Gln
                85                  90                  95

Arg Ala Arg Ile Ser Ala Leu Ser Asp Asn Gly Glu His Phe Ser Ala
            100                 105                 110

Lys Ala Glu Tyr Leu Glu Ser Pro Thr Ile Asp Glu Arg Glu Gln Glu
        115                 120                 125

Val Leu Val Arg Thr Ala Ile Ser Gln Phe Glu Gly Tyr Ile Lys Leu
    130                 135                 140

Asn Lys Lys Ile Pro Pro Glu Val Leu Thr Ser Leu Asn Ser Ile Asp
145                 150                 155                 160

Asp Pro Ala Arg Leu Ala Asp Thr Ile Ala Ala His Met Pro Leu Lys
                165                 170                 175

Leu Ala Asp Lys Gln Ser Val Leu Glu Met Ser Asp Val Asn Glu Arg
            180                 185                 190

Leu Glu Tyr Leu Met Ala Met Met Glu Ser Glu Ile Asp Leu Leu Gln
        195                 200                 205

Val Glu Lys Arg Ile Arg Asn Arg Val Lys Gln Met Glu Lys Ser
    210                 215                 220

Gln Arg Glu Tyr Tyr Leu Asn Glu Gln Met Lys Ala Ile Gln Lys Glu
225                 230                 235                 240

Leu Gly Glu Met Asp Asp Ala Pro Asp Glu Asn Glu Ala Leu Lys Arg
                245                 250                 255

Lys Ile Asp Ala Ala Lys Met Pro Lys Glu Ala Lys Glu Lys Ala Glu
            260                 265                 270

Ala Glu Leu Gln Lys Leu Lys Met Met Ser Pro Met Ser Ala Glu Ala
        275                 280                 285

Thr Val Val Arg Gly Tyr Ile Asp Trp Met Val Gln Val Pro Trp Asn
    290                 295                 300

Ala Arg Ser Lys Val Lys Lys Asp Leu Arg Gln Ala Gln Glu Ile Leu
305                 310                 315                 320

Asp Thr Asp His Tyr Gly Leu Glu Arg Val Lys Asp Arg Ile Leu Glu
                325                 330                 335

Tyr Leu Ala Val Gln Ser Arg Val Asn Lys Ile Lys Gly Pro Ile Leu
            340                 345                 350

Cys Leu Val Gly Pro Pro Gly Val Gly Lys Thr Ser Leu Gly Gln Ser
        355                 360                 365

Ile Ala Lys Ala Thr Gly Arg Lys Tyr Val Arg Met Ala Leu Gly Gly
    370                 375                 380

Val Arg Asp Glu Ala Glu Ile Arg Gly His Arg Arg Thr Tyr Ile Gly
385                 390                 395                 400

Ser Met Pro Gly Lys Leu Ile Gln Lys Met Ala Lys Val Gly Val Lys
```

```
                    405                 410                 415
Asn Pro Leu Phe Leu Asp Glu Ile Asp Lys Met Ser Ser Asp Met
            420                 425                 430

Arg Gly Asp Pro Ala Ser Ala Leu Leu Glu Val Leu Asp Pro Glu Gln
            435                 440                 445

Asn Val Ala Phe Ser Asp His Tyr Leu Glu Val Asp Tyr Asp Leu Ser
450                 455                 460

Asp Val Met Phe Val Ala Thr Ser Asn Ser Met Asn Ile Pro Ala Pro
465                 470                 475                 480

Leu Leu Asp Arg Met Glu Val Ile Arg Leu Ser Gly Tyr Thr Glu Asp
            485                 490                 495

Glu Lys Leu Asn Ile Ala Lys Arg His Leu Leu Pro Lys Gln Ile Glu
            500                 505                 510

Arg Asn Ala Leu Lys Lys Gly Glu Leu Thr Val Asp Asp Ser Ala Ile
            515                 520                 525

Ile Gly Ile Ile Arg Tyr Tyr Thr Arg Glu Ala Gly Val Arg Gly Leu
            530                 535                 540

Glu Arg Glu Ile Ser Lys Leu Cys Arg Lys Ala Val Lys Gln Leu Leu
545                 550                 555                 560

Leu Asp Lys Ser Leu Lys His Ile Glu Ile Asn Gly Asp Asn Leu His
            565                 570                 575

Asp Tyr Leu Gly Val Gln Arg Phe Asp Tyr Gly Arg Ala Asp Asn Glu
            580                 585                 590

Asn Arg Val Gly Gln Val Thr Gly Leu Ala Trp Thr Glu Val Gly Gly
            595                 600                 605

Asp Leu Leu Thr Ile Glu Thr Ala Cys Val Pro Gly Lys Gly Lys Leu
610                 615                 620

Thr Tyr Thr Gly Ser Leu Gly Glu Val Met Gln Glu Ser Ile Gln Ala
625                 630                 635                 640

Ala Leu Thr Val Val Arg Ala Arg Ala Glu Lys Leu Gly Ile Asn Pro
            645                 650                 655

Asp Phe Tyr Glu Lys Arg Asp Ile His Val His Val Pro Glu Gly Ala
            660                 665                 670

Thr Pro Lys Asp Gly Pro Ser Ala Gly Ile Ala Met Cys Thr Ala Leu
            675                 680                 685

Val Ser Cys Leu Thr Gly Asn Pro Val Arg Ala Asp Val Ala Met Thr
690                 695                 700

Gly Glu Ile Thr Leu Arg Gly Gln Val Leu Pro Ile Gly Gly Leu Lys
705                 710                 715                 720

Glu Lys Leu Leu Ala Ala His Arg Gly Gly Ile Lys Thr Val Leu Ile
            725                 730                 735

Pro Phe Glu Asn Lys Arg Asp Leu Glu Glu Ile Pro Asp Asn Val Ile
            740                 745                 750

Ala Asp Leu Asp Ile His Pro Val Lys Arg Ile Glu Glu Val Leu Thr
            755                 760                 765

Leu Ala Leu Gln Asn Glu Pro Ser Gly Met Gln Val Val Thr Ala Lys
            770                 775                 780

<210> SEQ ID NO 11
<211> LENGTH: 264
<212> TYPE: PRT
<213> ORGANISM: Escherichia coli

<400> SEQUENCE: 11
```

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 12
<211> LENGTH: 1024
<212> TYPE: PRT
<213> ORGANISM: Escherichia coli

<400> SEQUENCE: 12

Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
                20                  25                  30

Pro Phe Ala Ser Trp Arg Asn Ser Glu Glu Ala Arg Thr Asp Arg Pro
            35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Val Pro Ser Asn Trp Gln Met His Gly Tyr
                85                  90                  95

Asp Ala Pro Ile Tyr Thr Asn Val Thr Tyr Pro Ile Thr Val Asn Pro
                100                 105                 110

```
Pro Phe Val Pro Thr Glu Asn Pro Thr Gly Cys Tyr Ser Leu Thr Phe
    115                 120                 125

Asn Val Asp Glu Ser Trp Leu Gln Glu Gly Gln Thr Arg Ile Ile Phe
130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
            195                 200                 205

Ile Phe Arg Asp Val Ser Leu Leu His Lys Pro Thr Thr Gln Ile Ser
        210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
            355                 360                 365

Asp Glu Gln Thr Met Val Gln Asp Ile Leu Leu Met Lys Gln Asn Asn
        370                 375                 380

Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
            420                 425                 430

Trp Leu Pro Ala Met Ser Glu Arg Val Thr Arg Met Val Gln Arg Asp
            435                 440                 445

Arg Asn His Pro Ser Val Ile Ile Trp Ser Leu Gly Asn Glu Ser Gly
        450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Gly Ala Asp Thr Thr Ala
                485                 490                 495

Thr Asp Ile Ile Cys Pro Met Tyr Ala Arg Val Asp Glu Asp Gln Pro
            500                 505                 510

Phe Pro Ala Val Pro Lys Trp Ser Ile Lys Lys Trp Leu Ser Leu Pro
            515                 520                 525
```

Gly Glu Thr Arg Pro Leu Ile Leu Cys Glu Tyr Ala His Ala Met Gly
530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
                565                 570                 575

Ile Lys Tyr Asp Glu Asn Gly Asn Pro Trp Ser Ala Tyr Gly Gly Asp
            580                 585                 590

Phe Gly Asp Thr Pro Asn Asp Arg Gln Phe Cys Met Asn Gly Leu Val
    595                 600                 605

Phe Ala Asp Arg Thr Pro His Pro Ala Leu Thr Glu Ala Lys His Gln
610                 615                 620

Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
                645                 650                 655

Val Ala Leu Asp Gly Lys Pro Leu Ala Ser Gly Glu Val Pro Leu Asp
            660                 665                 670

Val Ala Pro Gln Gly Lys Gln Leu Ile Glu Leu Pro Glu Leu Pro Gln
    675                 680                 685

Pro Glu Ser Ala Gly Gln Leu Trp Leu Thr Val Arg Val Val Gln Pro
690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
                725                 730                 735

Ala Ile Pro His Leu Thr Thr Ser Glu Met Asp Phe Cys Ile Glu Leu
            740                 745                 750

Gly Asn Lys Arg Trp Gln Phe Asn Arg Gln Ser Gly Phe Leu Ser Gln
    755                 760                 765

Met Trp Ile Gly Asp Lys Lys Gln Leu Leu Thr Pro Leu Arg Asp Gln
770                 775                 780

Phe Thr Arg Ala Pro Leu Asp Asn Asp Ile Gly Val Ser Glu Ala Thr
785                 790                 795                 800

Arg Ile Asp Pro Asn Ala Trp Val Glu Arg Trp Lys Ala Ala Gly His
                805                 810                 815

Tyr Gln Ala Glu Ala Ala Leu Leu Gln Cys Thr Ala Asp Thr Leu Ala
            820                 825                 830

Asp Ala Val Leu Ile Thr Thr Ala His Ala Trp Gln His Gln Gly Lys
    835                 840                 845

Thr Leu Phe Ile Ser Arg Lys Thr Tyr Arg Ile Asp Gly Ser Gly Gln
850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
    915                 920                 925

Pro Tyr Val Phe Pro Ser Glu Asn Gly Leu Arg Cys Gly Thr Arg Glu
930                 935                 940

Leu Asn Tyr Gly Pro His Gln Trp Arg Gly Asp Phe Gln Phe Asn Ile

-continued

```
                945                 950                 955                 960
Ser Arg Tyr Ser Gln Gln Gln Leu Met Glu Thr Ser His Arg His Leu
                    965                 970                 975

Leu His Ala Glu Glu Gly Thr Trp Leu Asn Ile Asp Gly Phe His Met
                    980                 985                 990

Gly Ile Gly Gly Asp Asp Ser Trp Ser Pro Ser Val Ser Ala Glu Phe
                    995                 1000                1005

Gln Leu Ser Ala Gly Arg Tyr His Tyr Gln Leu Val Trp Cys Gln
    1010                1015                1020

Lys

<210> SEQ ID NO 13
<211> LENGTH: 784
<212> TYPE: PRT
<213> ORGANISM: Escherichia coli

<400> SEQUENCE: 13

Met Asn Pro Glu Arg Ser Glu Arg Ile Glu Ile Pro Val Leu Pro Leu
1               5                   10                  15

Arg Asp Val Val Tyr Pro His Met Val Ile Pro Leu Phe Val Gly
            20                  25                  30

Arg Glu Lys Ser Ile Arg Cys Leu Glu Ala Ala Met Asp His Asp Lys
        35                  40                  45

Lys Ile Met Leu Val Ala Gln Lys Glu Ala Ser Thr Asp Glu Pro Gly
    50                  55                  60

Val Asn Asp Leu Phe Thr Val Gly Thr Val Ala Ser Ile Leu Gln Met
65                  70                  75                  80

Leu Lys Leu Pro Asp Gly Thr Val Lys Val Leu Val Glu Gly Leu Gln
                85                  90                  95

Arg Ala Arg Ile Ser Ala Leu Ser Asp Asn Gly Glu His Phe Ser Ala
            100                 105                 110

Lys Ala Glu Tyr Leu Glu Ser Pro Thr Ile Asp Glu Arg Glu Gln Glu
        115                 120                 125

Val Leu Val Arg Thr Ala Ile Ser Gln Phe Glu Gly Tyr Ile Lys Leu
    130                 135                 140

Asn Lys Lys Ile Pro Pro Glu Val Leu Thr Ser Leu Asn Ser Ile Asp
145                 150                 155                 160

Asp Pro Ala Arg Leu Ala Asp Thr Ile Ala Ala His Met Pro Leu Lys
                165                 170                 175

Leu Ala Asp Lys Gln Ser Val Leu Glu Met Ser Asp Val Asn Glu Arg
            180                 185                 190

Leu Glu Tyr Leu Met Ala Met Met Glu Ser Glu Ile Asp Leu Leu Gln
        195                 200                 205

Val Glu Lys Arg Ile Arg Asn Arg Val Lys Lys Gln Met Glu Lys Ser
    210                 215                 220

Gln Arg Glu Tyr Tyr Leu Asn Glu Gln Met Lys Ala Ile Gln Lys Glu
225                 230                 235                 240

Leu Gly Glu Met Asp Asp Ala Pro Asp Glu Asn Glu Ala Leu Lys Arg
                245                 250                 255

Lys Ile Asp Ala Ala Lys Met Pro Lys Glu Ala Lys Glu Lys Ala Glu
            260                 265                 270

Ala Glu Leu Gln Lys Leu Lys Met Met Ser Pro Met Ser Ala Glu Ala
        275                 280                 285

Thr Val Val Arg Gly Tyr Ile Asp Trp Met Val Gln Val Pro Trp Asn
```

```
                290                 295                 300
Ala Arg Ser Lys Val Lys Lys Asp Leu Arg Gln Ala Gln Glu Ile Leu
305                 310                 315                 320

Asp Thr Asp His Tyr Gly Leu Glu Arg Val Lys Asp Arg Ile Leu Glu
                325                 330                 335

Tyr Leu Ala Val Gln Ser Arg Val Asn Lys Ile Lys Gly Pro Ile Leu
                340                 345                 350

Cys Leu Val Gly Pro Pro Gly Val Gly Lys Thr Ser Leu Gly Gln Ser
                355                 360                 365

Ile Ala Lys Ala Thr Gly Arg Lys Tyr Val Arg Met Ala Leu Gly Gly
                370                 375                 380

Val Arg Asp Glu Ala Glu Ile Arg Gly His Arg Arg Thr Tyr Ile Gly
385                 390                 395                 400

Ser Met Pro Gly Lys Leu Ile Gln Lys Met Ala Lys Val Gly Val Lys
                405                 410                 415

Asn Pro Leu Phe Leu Leu Asp Glu Ile Asp Lys Met Ser Ser Asp Met
                420                 425                 430

Arg Gly Asp Pro Ala Ser Ala Leu Leu Glu Val Leu Asp Pro Glu Gln
                435                 440                 445

Asn Val Ala Phe Ser Asp His Tyr Leu Glu Val Asp Tyr Asp Leu Ser
                450                 455                 460

Asp Val Met Phe Val Ala Thr Ser Asn Ser Met Asn Ile Pro Ala Pro
465                 470                 475                 480

Leu Leu Asp Arg Met Glu Val Ile Arg Leu Ser Gly Tyr Thr Glu Asp
                485                 490                 495

Glu Lys Leu Asn Ile Ala Lys Arg His Leu Leu Pro Lys Gln Ile Glu
                500                 505                 510

Arg Asn Ala Leu Lys Lys Gly Glu Leu Thr Val Asp Asp Ser Ala Ile
                515                 520                 525

Ile Gly Ile Ile Arg Tyr Tyr Thr Arg Glu Ala Gly Val Arg Gly Leu
                530                 535                 540

Glu Arg Glu Ile Ser Lys Leu Cys Arg Lys Ala Val Lys Gln Leu Leu
545                 550                 555                 560

Leu Asp Lys Ser Leu Lys His Ile Glu Ile Asn Gly Asp Asn Leu His
                565                 570                 575

Asp Tyr Leu Gly Val Gln Arg Phe Asp Tyr Gly Arg Ala Asp Asn Glu
                580                 585                 590

Asn Arg Val Gly Gln Val Thr Gly Leu Ala Trp Thr Glu Val Gly Gly
                595                 600                 605

Asp Leu Leu Thr Ile Glu Thr Ala Cys Val Pro Gly Lys Gly Lys Leu
                610                 615                 620

Thr Tyr Thr Gly Ser Leu Gly Glu Val Met Gln Glu Ser Ile Gln Ala
625                 630                 635                 640

Ala Leu Thr Val Val Arg Ala Arg Ala Glu Lys Leu Gly Ile Asn Pro
                645                 650                 655

Asp Phe Tyr Glu Lys Arg Asp Ile His Val His Val Pro Glu Gly Ala
                660                 665                 670

Thr Pro Lys Asp Gly Pro Ser Ala Gly Ile Ala Met Cys Thr Ala Leu
                675                 680                 685

Val Ser Cys Leu Thr Gly Asn Pro Val Arg Ala Asp Val Ala Met Thr
                690                 695                 700

Gly Glu Ile Thr Leu Arg Gly Gln Val Leu Pro Ile Gly Gly Leu Lys
705                 710                 715                 720
```

Glu Lys Leu Leu Ala Ala His Arg Gly Gly Ile Lys Thr Val Leu Ile
            725                 730                 735

Pro Phe Glu Asn Lys Arg Asp Leu Glu Ile Pro Asp Asn Val Ile
        740                 745                 750

Ala Asp Leu Asp Ile His Pro Val Lys Arg Ile Glu Glu Val Leu Thr
            755                 760                 765

Leu Ala Leu Gln Asn Glu Pro Ser Gly Met Gln Val Val Thr Ala Lys
        770                 775                 780

<210> SEQ ID NO 14
<211> LENGTH: 90
<212> TYPE: PRT
<213> ORGANISM: Escherichia coli

<400> SEQUENCE: 14

Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
            20                  25                  30

Thr Glu Ser Leu Lys Glu Gly Asp Asp Val Ala Leu Val Gly Phe Gly
        35                  40                  45

Thr Phe Ala Val Lys Glu Arg Ala Ala Arg Thr Gly Arg Asn Pro Gln
    50                  55                  60

Thr Gly Lys Glu Ile Thr Ile Ala Ala Lys Val Pro Ser Phe Arg
65                  70                  75                  80

Ala Gly Lys Ala Leu Lys Asp Ala Val Asn
            85                  90

<210> SEQ ID NO 15
<211> LENGTH: 5049
<212> TYPE: DNA
<213> ORGANISM: Escherichia coli

<400> SEQUENCE: 15
gtccatggaa gacgtcgaaa aagtggttat cgacgagtcg gtaattgatg gtcaaagcaa      60
accgttgctg atttatggca agccggaagc gcaacaggca tctggtgaat aattaaccat     120
tcccatacaa ttagttaacc aaaaaggggg gatttatct ccccttaat ttttcctcta      180
ttctcggcgt tgaatgtggg ggaaacatcc ccatatactg acgtacatgt taatagatgg     240
cgtgaagcac agtcgtgtca tctgattacc tggcggaaat taaactaaga gagagctcta     300
tgattccggg gatccgtcga cctgcagttc gaagttccta ttctctagaa agtataggaa     360
cttcagagcg cttttgaagc tcacgctgcc gcaagcactc agggcgcaag ggctgctaaa     420
ggaagcggaa cacgtagaaa gccagtccgc agaaacggtg ctgaccccgg atgaatgtca     480
gctactgggc tatctggaca agggaaaacg caagcgcaaa gagaaagcag gtagcttgca     540
gtgggcttac atggcgatag ctagactggg cggttttatg gacagcaagc gaaccggaat     600
tgccagctgg ggcgccctct ggtaaggttg gaagccctg caaagtaaac tggatggctt     660
tcttgccgcc aaggatctga tggcgcaggg gatcaagatc tgatcaagag acaggatgag     720
gatcgtttcg catgattgaa caagatggat tgcacgcagg ttctccggcc gcttgggtgg     780
agaggctatt cggctatgac tgggcacaac agacaatcgg ctgctctgat gccgccgtgt     840
tccggctgtc agcgcagggg cgcccggttc tttttgtcaa gaccgacctg tccggtgccc     900
tgaatgaact gcaggacgag gcagcgcggc tatcgtggct ggccacgacg ggcgttcctt     960

-continued

```
gcgcagctgt gctcgacgtt gtcactgaag cgggaaggga ctggctgcta ttgggcgaag    1020
tgccggggca ggatctcctg tcatctcacc ttgctcctgc cgagaaagta tccatcatgg    1080
ctgatgcaat gcggcggctg catacgcttg atccggctac ctgcccattc gaccaccaag    1140
cgaaacatcg catcgagcga gcacgtactc ggatggaagc cggtcttgtc gatcaggatg    1200
atctggacga agagcatcag gggctcgcgc cagccgaact gttcgccagg ctcaaggcgc    1260
gcatgcccga cggcgaggat ctcgtcgtga cccatggcga tgcctgcttg ccgaatatca    1320
tggtggaaaa tggccgcttt tctggattca tcgactgtgg ccggctgggt gtggcggacc    1380
gctatcagga catagcgttg gctacccgtg atattgctga agagcttggc ggcgaatggg    1440
ctgaccgctt cctcgtgctt tacggtatcg ccgctcccga ttcgcagcgc atcgccttct    1500
atcgccttct tgacgagttc ttctaataag gggatcttga agttcctatt ccgaagttcc    1560
tattctctag aaagtatagg aacttcgaag cagctccagc ctacataaag cggccgctta    1620
tttttgacac cagaccaact ggtaatggta gcgaccggcg ctcagctgga attccgccga    1680
tactgacggg ctccaggagt cgtcgccacc aatccccata tggaaaccgt cgatattcag    1740
ccatgtgcct tcttccgcgt gcagcagatg gcgatggctg gtttccatca gttgctgttg    1800
actgtagcgg ctgatgttga actggaagtc gccgcgccac tggtgtgggc cataattcaa    1860
ttcgcgcgtc ccgcagcgca gaccgttttc gctcgggaag acgtacgggg tatacatgtc    1920
tgacaatggc agatcccagc ggtcaaaaca ggcggcagta aggcggtcgg atagttttc    1980 ttgcggccct aatccgagcc agtttacccg ctctgctacc tgcgccagct ggcagttcag    2040
gccaatccgc gccggatgcg gtgtatcgct cgccacttca acatcaacgg taatcgccat    2100
ttgaccacta ccatcaatcc ggtaggtttt ccggctgata ataaggtttt cccctgatg    2160 ctgccacgcg tgagcggtcg taatcagcac cgcatcagca agtgtatctg ccgtgcactg    2220
caacaacgct gcttcggcct ggtaatggcc cgccgccttc cagcgttcga cccaggcgtt    2280
agggtcaatg cgggtcgctt cacttacgcc aatgtcgtta ccagcggtg cacgggtgaa    2340 ctgatcgcgc agcggcgtca gcagttgttt tttatcgcca atccacatct gtgaaagaaa    2400
gcctgactgg cggttaaatt gccaacgctt attacccagc tcgatgcaaa aatccatttc    2460
gctggtggtc agatgcggga tggcgtggga cgcggcgggg agcgtcacac tgaggttttc    2520
cgccagacgc cactgctgcc aggcgctgat gtgcccggct tctgaccatg cggtcgcgtt    2580
cggttgcact acgcgtactg tgagccagag ttgcccggcg ctctccggct gcggtagttc    2640
aggcagttca atcaactgtt taccttgtgg agcgacatcc agaggcactt caccgcttgc    2700
cagcggctta ccatccagcg ccaccatcca gtgcaggagc tcgttatcgc tatgacggaa    2760
caggtattcg ctggtcactt cgatggtttg cccggataaa cggaactgga aaaactgctg    2820
ctggtgtttt gcttccgtca gcgctggatg cggcgtgcgg tcggcaaaga ccagaccgtt    2880
catacagaac tggcgatcgt tcggcgtatc gccaaaatca ccgccgtaag ccgaccacgg    2940
gttgccgttt tcatcatatt taatcagcga ctgatccacc cagtcccaga cgaagccgcc    3000
ctgtaaacgg ggatactgac gaaacgcctg ccagtattta gcgaaaccgc caagactgtt    3060
acccatcgcg tgggcgtatt cgcaaaggat cagcgggcgc gtctctccag gtagcgaaag    3120
ccattttttg atggaccatt tcggcacagc cgggaagggc tggtcttcat ccacgcgcgc    3180
gtacatcggg caaataatat cggtggccgt ggtgtcggct ccgccgcctt catactgcac    3240
cgggcgggaa ggatcgacag atttgatcca gcgatacagc gcgtcgtgat tagcgccgtg    3300
gcctgattca ttccccagcg accagatgat cacactcggg tgattacgat cgcgctgcac    3360
```

-continued

```
cattcgcgtt acgcgttcgc tcatcgccgg tagccagcgc ggatcatcgg tcagacgatt    3420
cattggcacc atgccgtggg tttcaatatt ggcttcatcc accacataca ggccgtagcg    3480
gtcgcacagc gtgtaccaca gcggatggtt cggataatgc gaacagcgca cggcgttaaa    3540
gttgttctgc ttcatcagca ggatatcctg caccatcgtc tgctcatcca tgacctgacc    3600
atgcagagga tgatgctcgt gacggttaac gcctcgaatc agcaacggct tgccgttcag    3660
cagcagcaga ccattttcaa tccgcacctc gcggaaaccg acatcgcagg cttctgcttc    3720
aatcagcgtg ccgtcggcgg tgtgcagttc aaccaccgca cgatagagat tcgggatttc    3780
ggcgctccac agtttcgggt tttcgacgtt cagacgtagt gtgacgcgat cggcataacc    3840
accacgctca tcgataattt caccgccgaa aggcgcggtg ccgctggcga cctgcgtttc    3900
accctgccat aaagaaactg ttaccgctag gtagtcacgc aactcgccgc acatctgaac    3960
ttcagcctcc agtacagcgc ggctgaaatc atcattaaag cgagtggcaa catggaaatc    4020
gctgatttgt gtagtcggtt tatgcagcaa cgagacgtca cggaaaatgc cgctcatccg    4080
ccacatatcc tgatcttcca gataactgcc gtcactccag cgcagcacca tcaccgcgag    4140
gcggttttct ccggcgcgta aaaatgcgct caggtcaaat tcagacggca aacgactgtc    4200
ctggccgtaa ccgacccagc gcccgttgca ccacagatga aacgccgagt taacgccatc    4260
aaaaataatt cgcgtctggc cttcctgtag ccagctttca tcaacattaa atgtgagcga    4320
gtaacaaccc gtcggattct ccgtgggaac aaacggcgga ttgaccgtaa tgggataggt    4380
cacgttggtg tagatgggcg catcgtaacc gtgcatctgc cagtttgagg ggacgacgac    4440
agtatcggcc tcaggaagat cgcactccag ccagctttcc ggcaccgctt ctggtgccgg    4500
aaaccaggca aagcgccatt cgccattcag gctgcgcaac tgttgggaag ggcgatcggt    4560
gcgggcctct tcgctattac gccagctggc gaaaggggga tgtgctgcaa ggcgattaag    4620
ttgggtaacg ccaggttttt cccagtcacg acgttgtaaa acgacggcca gtgaatccgt    4680
aatcatggtc atagtaggtt tcctcaggtt gtgactgcaa aatagtgacc tcgcgcaaaa    4740
tgcactaata aaaacagggc tggcaggcta attcgggctt gccagccttt ttttgtctcg    4800
ctaagttaga tggcggatcg ggcttgccct tattaagggg tgttgtaagg ggatggctgg    4860
cctgatataa ctgctgcgcg ttcgtacctt gaaggattca agtgcgatat aaattataaa    4920
gaggaagaga agagtgaata aatctcaatt gatcgacaag attgctgcag gggctgatat    4980
ctctaaagct gcggctggcc gtgcgttaga tgctattatt gcttccgtaa ctgaatctct    5040
gaaagaagg                                                            5049
```

UNITED STATES PATENT AND TRADEMARK OFFICE
CERTIFICATE OF CORRECTION

PATENT NO. : 11,028,419 B2
APPLICATION NO. : 15/442127
DATED : June 8, 2021
INVENTOR(S) : Merighi et al.

It is certified that error appears in the above-identified patent and that said Letters Patent is hereby corrected as shown below:

In the Claims

Column 120, Line 55 Claim 4, change "The method of claim 1," to "The method of claim 3,"

Signed and Sealed this
Twenty-first Day of June, 2022

Katherine Kelly Vidal
*Director of the United States Patent and Trademark Office*